(12) United States Patent
Kondo et al.

(10) Patent No.: US 11,447,525 B2
(45) Date of Patent: Sep. 20, 2022

(54) PEPTIDE AND USE THEREFOR

(71) Applicant: NIIGATA UNIVERSITY, Niigata (JP)

(72) Inventors: Eisaku Kondo, Niigata (JP); Ken Saito, Niigata (JP)

(73) Assignee: NIIGATA UNIVERSITY, Niigata (JP)

( * ) Notice: Subject to any disclaimer, the term of this patent is extended or adjusted under 35 U.S.C. 154(b) by 0 days.

(21) Appl. No.: 17/044,972

(22) PCT Filed: Apr. 25, 2019

(86) PCT No.: PCT/JP2019/017629
§ 371 (c)(1),
(2) Date: Oct. 2, 2020

(87) PCT Pub. No.: WO2019/212031
PCT Pub. Date: Nov. 7, 2019

(65) Prior Publication Data
US 2021/0163537 A1 Jun. 3, 2021

(30) Foreign Application Priority Data
May 2, 2018 (JP) .............................. JP2018-088811

(51) Int. Cl.
| C07K 7/08 | (2006.01) |
| A61K 47/64 | (2017.01) |
| A61P 35/00 | (2006.01) |
| A61K 49/00 | (2006.01) |
| C07K 7/06 | (2006.01) |

(52) U.S. Cl.
CPC .............. C07K 7/08 (2013.01); A61K 47/64 (2017.08); A61K 49/0056 (2013.01); A61P 35/00 (2018.01); C07K 7/06 (2013.01)

(58) Field of Classification Search
CPC .................................. C07K 7/08; A61K 47/64
See application file for complete search history.

(56) References Cited

U.S. PATENT DOCUMENTS

| 10,668,125 B2 * | 6/2020 | Kondo .................. A61K 47/42 |
| 2015/0297742 A1 | 10/2015 | Strieker et al. |
| 2018/0360903 A1 | 12/2018 | Kondo et al. |

FOREIGN PATENT DOCUMENTS

| JP | A-2015-504073 | 2/2015 |
| JP | B-5721140 | 5/2015 |
| KR | 10-2015-0130249 | 11/2015 |
| WO | WO 2013/106273 | 7/2013 |
| WO | WO 2014/164684 | 10/2014 |
| WO | WO 2017/086090 | 5/2017 |

OTHER PUBLICATIONS

PCT International Search Report in International Appln. No. PCT/JP2019/017629, dated Jul. 30, 2019, 4 pages (with English Translation).
Vivès et al., "A Truncated HIV-1 Tat Protein Basic Domain Rapidly Translocates through the Plasma Membrane and Accumulates in the Cell Nucleus," J. Biol. Chem., 1997, 272(25):16010-16017.
Erazo-Oliveras et al., "Improving the endosomal escape of cell-penetrating peptides and their cargos: strategies and challenges," Pharmaceuticals, Nov. 2012, 5(12):1177-1209.
Extended Search Report in European Appln. No. 19796420.8, dated Jan. 27, 2022, 10 pages.
Nakase et al., "Accumulation of arginine-rich cell-penetrating peptides in tumors and the potential for anticancer drug delivery in vivo," Journal of Controlled Release, Jan. 2012, 159(2):181-188.
Srinivasan et al., "Conjugation to the cell-penetrating peptide TAT potentiates the photodynamic effect of carboxytetramethylrhodamine," PLOS ONE, Mar. 2011, 6(3):e17732.

* cited by examiner

*Primary Examiner* — Amber D Steele
(74) *Attorney, Agent, or Firm* — Fish & Richardson P.C.

(57) ABSTRACT

This peptide is composed of an amino acid sequence represented by general formula (I), and has a high degree of accumulation in cancer cells or cancer tissue in a digestive system. In general formula (I), $X^{11}$ is a peptide residue composed of an amino acid sequence of (a) or (b) below: (a) an amino acid sequence represented by any of SEQ ID NOs: 1 to 3, (b) an amino acid sequence including a sequence in which one or two amino acids have been deleted, substituted or added in an amino acid sequence represented by any of SEQ ID NOs: 1 to 3; $Y^{11}$ is a peptide linker composed of an amino acid residue of at least 1 but not more than 10 amino acids, wherein each amino acid residue is independently a glycine residue, a proline residue, a serine residue, a cysteine residue or a lysine residue; $X^{12}$ is either a peptide residue composed of an amino acid sequence of (a) or (b) above, or a retro-inverso peptide residue thereof; and n11 represents an integer of at least 1 but not more than 9.

$$X^{11}-(Y^{11}-X^{12})_{n11} \qquad \text{General formula (I):}$$

19 Claims, 32 Drawing Sheets
Specification includes a Sequence Listing.

PEPTIDE AND USE THEREFOR

SEQUENCE LISTING

The instant application contains a Sequence Listing which has been submitted electronically in ASCII format and is hereby incorporated by reference in its entirety. Said ASCII copy, created on Jan. 25, 2022, is named Sequence_Listing.txt and is 13 kilobytes in size.

TECHNICAL FIELD

The present invention relates to a peptide and use of that peptide. Specifically, the present invention relates to a peptide having a high degree of accumulation in cancer cells or cancer tissue in the digestive system, a nucleic acid that encodes the peptide, a peptide-drug conjugate containing the peptide, a pharmaceutical composition containing the peptide-drug conjugate, a labeled peptide containing the peptide, an imaging composition containing the labeled peptide, and a vector, a peptide-drug conjugate expression vector and a labeled peptide expression vector each having the above nucleic acid. Priority is claimed on Japanese Patent Application No. 2018-088811, filed May 2, 2018, the content of which is incorporated herein by reference.

BACKGROUND ART

Pancreatic cancer (invasive pancreatic ductal adenocarcinoma) has a mean survival time of about 6 months following diagnosis, and is among the most intractable malignancies. According to demographic statistics published by the Ministry of Health, Labor and Welfare, annual deaths due to pancreatic cancer continue to increase each year, and the 2016 statistics record 33,475 deaths. Further, deaths due to pancreatic cancer represent 9% of all cancer deaths, the fourth highest percentage following lung cancer, colon cancer and stomach cancer. According to an investigative report on nationwide pancreatic cancer registrations (2007), the number of resectable cases of pancreatic cancer represented approximately 40% of all cases, with the three-year survival rate for the resectable cases being a low 23.2%.

One reason for the difficulty in treating pancreatic cancer is that subjective symptoms are limited, making early detection difficult, and in the majority of cases, at the time of detection the cancer has already reached an advanced state, meaning surgical intervention is either impossible or limited to palliative operations. Further, other reasons that make treatment difficult include the fact that the tissue construct of invasive pancreatic ductal adenocarcinoma is a hard cancer (scirrhous carcinoma) that is accompanied by severe background fibrosis, the fact that pancreatic cancer cells themselves have a growth capacity and are biologically highly aggressive with high drug resistance, and the fact that pancreatic cancer has a propensity to readily invade or metastasize from an early stage. The characteristic stroma in pancreatic cancer with severe fibrosis act as a barrier that inhibits effective penetration of anticancer drugs to the cancer cells, which in combination with the various issues outlined above, means there are currently no effective anticancer drugs capable of significantly improving this type of situation, leaving future development the current hope.

Incidentally, among trends in the pharmaceutical field for the utilization of peptides as biomaterials, cell membrane-permeable (bioabsorbable) peptides such as Tat, Penetratin and poly-arginin are attracting much attention. However, these peptides are absorbed extensively and non-selectively, with no distinction between normal cells or normal tissue and tumor cells or tumor tissue. Accordingly, application of these peptides to medical treatment DDS (drug delivery system) tools for patient malignant tumors including solid carcinomas, which requires target-selective drug delivery, is problematic due to the severe side-effects. In particular, cell membrane-permeable (bioabsorbable) peptides such as Tat that have been widely used in experimental systems around the world are known to cause accumulation in the liver (for example, see non-Patent Document 1).

In contrast, cyclic RGD is the only medicated peptide. Cyclic RGD targets the αvβ3 integrin that has been reported to be expressed highly in new blood vessels or vascular endothelial cells that constitute existing blood vessels (and in some tumor cells), acts through vascular hyperpermeability, and is expected to offer a drug transport effect by enhancement of an EPR (enhanced permeability and retention) effect (a substance diffusion effect via blood vessels). Accordingly, cyclic RGD is not used alone, but is rather used simultaneously in combination with another drug as an imaging agent or DDS agent (for example, see Patent Document 1). However, the permeability and action of cyclic RGD relative to cancer cells themselves is extremely poor, with the cyclic RGD system effectively offering mainly a drug diffusion effect via the blood vessels that is largely dependent on the structure (development and distribution of blood vessels) of the tumor tissue. For these reasons, a satisfactory effect cannot be expected in those cases where an anticancer treatment based on direct elimination of the cancer cells themselves is being targeted.

In order to address the types of issues outlined above, the inventors of the present invention have been developing peptides which act directly on pancreatic cancer cells or pancreatic cancer tissue, and act directly on (are incorporated into) tumors via highly shifted absorption (for example, see Patent Document 2).

Generally, oligopeptides composed of several to about 20 amino acids are known to be prone to rapid degradation, metabolism and excretion in vivo as a result of a large variety of proteases that exist within human blood plasma and cells, with elimination from the administered body typically occurring within a period of several minutes to several tens of minutes, and this ready decomposability is a significant problem when peptides are used in vivo as practical drugs. In actuality, although the peptide disclosed in Patent Document 2 exhibits a high degree of accumulation in pancreatic cancer cells or pancreatic cancer tissue, degradation of the constituent amino acids starts within several minutes of administration in the presence of blood plasma, with complete denaturation occurring within about 20 minutes, and therefore from a practicality viewpoint, there remains room for improvement from the perspective of in vivo degradation resistance.

PRIOR ART LITERATURE

Patent Documents

Patent Document 1: Japanese Patent (Granted) Publication No. 5721140
Patent Document 2: International Patent Publication No. 2017/086090

Non-Patent Document

Non-Patent Document 1: Vives E., et al., A Truncated HIV-1 Tat Protein Basic Domain Rapidly Translocates through the Plasma Membrane and Accumulates in the Cell Nucleus, J. Biol. Chem., 272, 16010-16017, 1997.

DISCLOSURE OF INVENTION

Problems to be Solved by the Invention

The present invention has been developed in light of the above serious current issues associated with practical application in the medical field, and provides a novel peptide having a high degree of accumulation in cancer cells or cancer tissue in the digestive system including pancreatic cancer, and also having excellent degradation resistance in vivo, and also provides a nucleic acid that encodes the peptide, a peptide-drug conjugate containing the peptide, a pharmaceutical composition containing the peptide-drug conjugate, a labeled peptide containing the peptide, an imaging composition containing the labeled peptide, and a vector, a peptide-drug conjugate expression vector and a labeled peptide expression vector each containing the above nucleic acid.

Means for Solving the Problems

As a result of intensive research aimed at achieving the objects described above, the inventors of the present invention discovered that a novel peptide having an optimized amino acid sequence and an optimized peptide design based on that amino acid sequence maintained a high degree of accumulation not only in pancreatic cancer cells or pancreatic cancer tissue, but also in cancer cells or cancer tissue of the digestive system, while also having outstanding degradation resistance and persistence of action in vivo, and they were thus able to complete the present invention.

In other words, the present invention includes the following aspects.

A peptide according to a first aspect of the present invention is composed of an amino acid sequence represented by general formula (I) shown below, and has a high degree of accumulation in cancer cells or cancer tissue in the digestive system.

[Formula 1]

$$X^{11}-(Y^{11}-X^{12})_{n11} \quad (I)$$

(In general formula (I), $X^{11}$ is a peptide residue composed of an amino acid sequence of (a) or (b) below:

(a) an amino acid sequence represented by any of SEQ ID NOs: 1 to 3, (b) an amino acid sequence including a sequence in which one or two amino acids have been deleted, substituted or added in an amino acid sequence represented by any of SEQ ID NOs: 1 to 3;

$Y^{11}$ is a peptide linker composed of an amino acid residue of at least 1 but not more than 10 amino acids, wherein each amino acid residue is independently a glycine residue, a proline residue, a serine residue, a cysteine residue or a lysine residue;

$X^{12}$ is either a peptide residue composed of an amino acid sequence of (a) or (b) above, or a retro-inverso peptide residue thereof. Further, n11 represents an integer of at least 1 but not more than 9.)

In the peptide according to the first aspect described above, $Y^{11}$ may be a peptide linker of at least 1 but not more than 10 amino acids, wherein each amino acid residue is independently a glycine residue, a cysteine residue or a lysine residue.

In the peptide according to the first aspect described above, n11 may be an integer of at least 1 but not more than 4.

In the peptide according to the first aspect described above, $X^{11}$ and $X^{12}$ may be peptide residues composed of the same amino acid sequence, or $X^{12}$ may be a retro-inverso peptide residue of $X^{11}$.

The peptide according to the first aspect described above may be composed of an amino acid sequence represented by any of SEQ ID NOs: 15 to 31.

A nucleic acid according to a second aspect of the present invention encodes the peptide according to the first aspect described above.

A peptide-drug-conjugate according to a third aspect of the present invention comprises the peptide according to the first aspect described above and a biologically active substance.

A pharmaceutical composition according to a fourth aspect of the present invention comprises the peptide-drug-conjugate according to the third aspect described above.

The pharmaceutical composition according to the fourth aspect may be used for treatment of cancer of the digestive system.

The pharmaceutical composition according to the fourth aspect may be used for pancreatic cancer treatment.

The above biologically active substance may be an anti-cancer drug.

A labeled peptide according to a fifth aspect of the present invention comprises the peptide according to the first aspect described above and a labeling substance.

The labeling substance may be a stable isotope, a radioisotope, or a fluorescent substance.

An imaging composition according to a sixth aspect of the present invention comprises the labeled peptide according to the fifth aspect described above.

The imaging composition according to the sixth aspect may be used for cancer of the digestive system.

The imaging composition according to the sixth aspect may be used for pancreatic cancer diagnosis.

A vector according to a seventh aspect of the present invention has the nucleic acid according to the second aspect described above.

A peptide-drug-conjugate expression vector according to an eighth aspect of the present invention has the nucleic acid according to the second aspect described above and a nucleic acid that encodes a biologically active substance.

A labeled peptide expression vector according to a ninth aspect of the present invention has the nucleic acid according to the second aspect described above and a nucleic acid that encodes a labeling substance.

Effects of the Invention

The peptide of the aspect described above has a high degree of accumulation in cancer cells or cancer tissue in the digestive system (and particularly in pancreatic cancer cells or pancreatic cancer tissue), and exhibits excellent in vivo degradation resistance.

EMBODIMENTS FOR CARRYING OUT THE INVENTION

Figure 1:
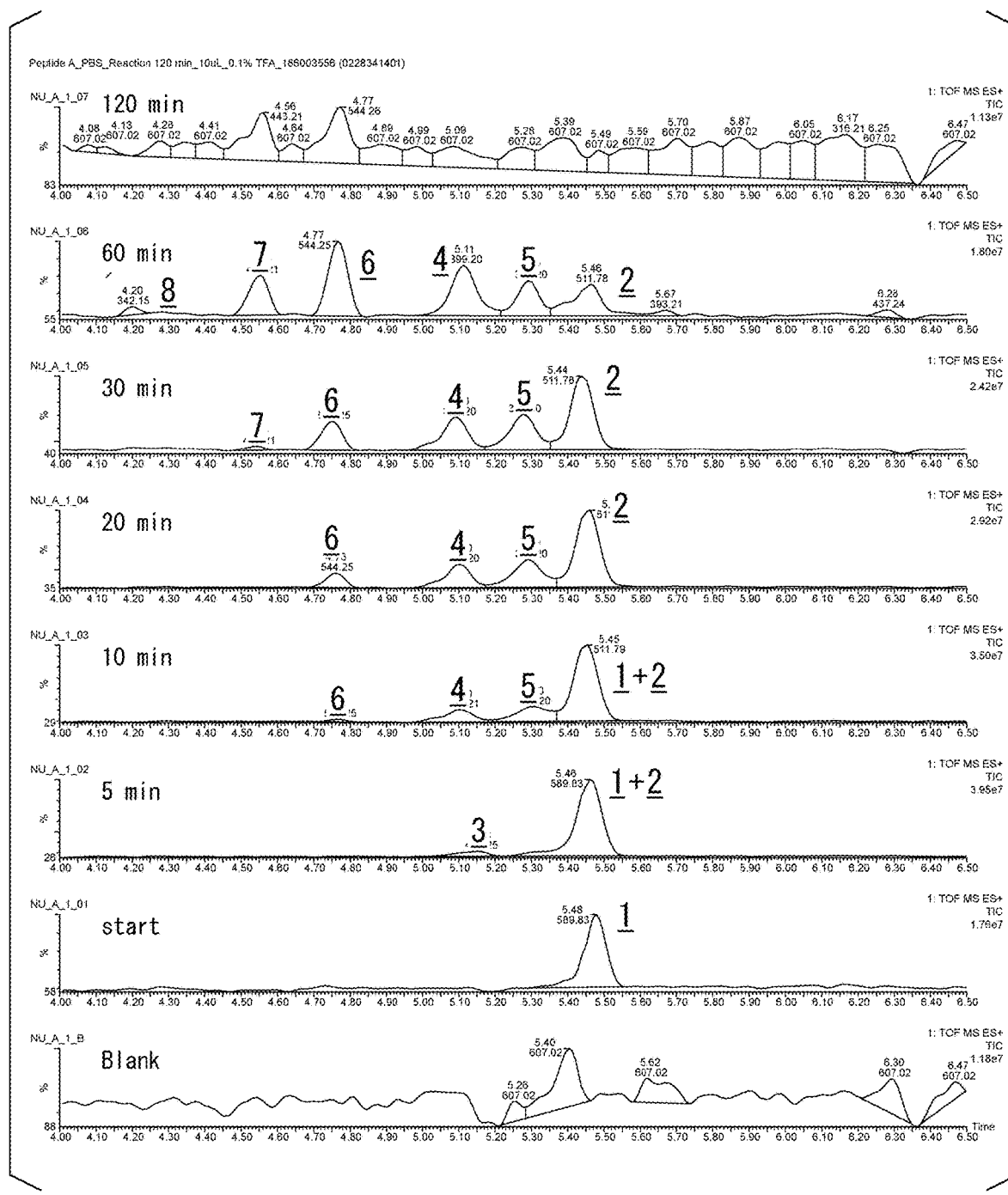
FIG. 1 is a graph illustrating the MALDI-TOFMS analysis results of degradation tests by human blood plasma using PCPP11 in Reference Example 1.

<<Peptide Having High Degree of Accumulation in Cancer Cells and Cancer Tissue in the Digestive System>>

A peptide of this embodiment is composed of an amino acid sequence represented by general formula (I) shown below, and has a high degree of accumulation in cancer cells or cancer tissue in the digestive system.

[Formula 2]

$$X^{11}-(Y^{11}-X^{12})_{n11} \qquad (I)$$

(In general formula (I), $X^{11}$ is a peptide residue composed of an amino acid sequence of (a) or (b) below:

(a) an amino acid sequence represented by any of SEQ ID NOs: 1 to 3, (b) an amino acid sequence including a sequence in which one or two amino acids have been deleted, substituted or added in an amino acid sequence represented by any of SEQ ID NOs: 1 to 3;

$Y^{11}$ is a peptide linker composed of an amino acid residue of at least 1 but not more than 10 amino acids, wherein each amino acid residue is independently a glycine residue, a proline residue, a serine residue, a cysteine residue or a lysine residue;

$X^{12}$ is either a peptide residue composed of an amino acid sequence of (a) or (b) above, or a retro-inverso peptide residue thereof. Further, n11 represents an integer of at least 1 but not more than 9.)

The PCPP11 peptide previously developed by the inventors of the present invention (for example, see International Patent Publication No. 2017/086090) (hereafter sometimes abbreviated as simply "PCPP11") exhibits accumulation shifted to a high degree toward pancreatic cancer cells and pancreatic cancer tissue compared with normal tissue and normal cells, but has issues in terms of in vivo stability (degradation resistance) when actually used. In order to address this issue, as outlined in the examples described below, by analyzing the degradation products obtained in degradation tests conducted on PCPP11, the inventors were able to optimize the amino acid sequence and the peptide design based on that amino acid sequence, and discovered a novel peptide which maintained a high degree of accumulation in cancer cells or cancer tissue of the digestive system, including pancreatic cancer cells or pancreatic cancer tissue, while also having outstanding degradation resistance and persistence of action in vivo, thus enabling them to complete the present invention.

In this description, a "cancer of the digestive system" means a malignancy that has developed from a digestive organ.

Specific examples of cancers of the digestive system include esophageal cancer, biliary tract cancer, liver cell cancer, pancreatic cancer, stomach cancer and colon cancer.

Further, "biliary tract cancer" includes cancers composed of bile duct cancer, gallbladder cancer, and duodenal papilla cancer. Moreover, bile duct cancer means malignant tumors that develop from the bile duct epithelium, and depending on the region of the bile duct in which the tumor is generated, the cancer may be differentiated into hepatic hilar bile duct cancer and perihilar bile duct cancer, which are extrahepatic bile duct cancers, and intrahepatic bile duct cancer (bile duct carcinoma). Gallbladder cancer means malignant tumors that develop from the gallbladder and the cystic duct. The duodenal papilla are composed of the papillary bile duct, the papillary pancreatic duct, the common bile duct and the major duodenal papilla, and duodenal papilla cancer means cancer that develops in these regions. Further, in terms of histopathological classification, these cancers can be designated as adenocarcinoma, adenosquamous carcinoma and intrahepatic cholangiocarcinoma.

Furthermore, "pancreatic cancer" means tumors that develop from the pancreas, and is also referred to as pancreatic carcinoma.

The pancreas is composed of acini that produce pancreatic juice, a pancreatic duct that transports the pancreatic juice, and the islets of Langerhans which are endocrine glands, and although cancer can develop in any of these tissues, the resulting tumors have completely different characteristics. Examples of the various types of pancreatic cancer (pancreatic carcinoma) include invasive pancreatic ductal carcinoma (invasive ductal carcinoma), intraductal papillary mucinous neoplasm (IPMN), intraductal tubulopapillary neoplasm (ITPN), pancreatic endocrine tumors, intraductal papillary mucinous neoplasm, mucinous cystic neoplasm, acinic cell carcinoma, serous cystadenocarcinoma, and metastatic pancreatic cancer. Among these, invasive pancreatic ductal carcinoma accounts for 80 to 90% of all tumor lesions formed in the pancreas.

Further, among the various pancreatic cancers, it is known that the mechanisms for the formation and progression of invasive pancreatic ductal carcinoma and the aforementioned biliary tract cancer are similar.

Among the various cancers of the digestive system described above, the peptide of an embodiment of the present invention has a particularly high degree of accumulation in the cells or tissue of stomach cancer, pancreatic cancer and biliary tract cancer. Further, the inventors of the present invention have also confirmed a similar high degree of accumulation in the cells or tissue of prostate cancer. Accordingly, it is surmised that the peptide of the present embodiment is targeting a specific receptor that is common on the cell surfaces of these cancers. Moreover, as illustrated in the examples described below, the peptide of the present embodiment is ideal for application to pancreatic cancer, and particularly to pancreatic cancer cells or pancreatic cancer tissue excluding pancreatic endocrine tumors and metastatic pancreatic cancer. Consequently, as described below, by using the peptide of the present embodiment as a delivery agent, the cancer cells or cancer tissue within almost all cases of patients suffering from cancer of the digestive system (and particularly pancreatic cancer patients) can be detected selectively and with high sensitivity. Moreover, these cancers of the digestive system (and particularly pancreatic cancer) can be treated. Furthermore, because it represents the most frequent tumor lesion formed in the pancreas, the peptide of the present embodiment is most preferably used for the treatment of invasive pancreatic ductal carcinoma.

In this description, the expression "high degree of accumulation in cancer cells or cancer tissue in the digestive system" means a property wherein a substance is absorbed and accumulates in the cancer cells or cancer tissue in the digestive system (and particularly in pancreatic cancer cells and pancreatic cancer tissue) to a high degree compared with the accumulation observed in normal tissue and malignant tumor cells within other systems.

<Amino Acid Sequence (I)>

The peptide of an embodiment of the present invention is composed of an amino acid sequence represented by general formula (I) shown below (hereafter sometimes referred to as "amino acid sequence (I)").

[Formula 3]

$$X^{11}-(Y^{11}-X^{12})_{n11} \quad (I)$$

[$X^{11}$]

In general formula (I), $X^{11}$ is a peptide residue composed of an amino acid sequence of (a) or (b) below:

(a) an amino acid sequence represented by any of SEQ ID NOs: 1 to 3, (b) an amino acid sequence including a sequence in which one or two amino acids have been deleted, substituted or added in an amino acid sequence represented by any of SEQ ID NOs: 1 to 3.

The amino acid sequences represented by SEQ ID NO: 1, 2 or 3 in (a) above are the amino acid sequences shown below.

```
                                         (SEQ ID NO: 1)
             RXPTTWHKP (SEQ ID NO: 2)
             AXXYTWIRA (SEQ ID NO: 3)
             RXWRQCRWR
```

X in SEQ ID NO: 1 is either R (an arginine residue) or mR (a methylated arginine residue). In other words, the amino acid sequence represented by SEQ ID NO: 1 includes the following amino acid sequences.

```
                                         (SEQ ID NO: 4)
             RRPTTWHKP (SEQ ID NO: 5)
             RmRPTTWHKP
```

X in SEQ ID NO: 2 is either R (an arginine residue) or mR (a methylated arginine residue). In other words, the amino acid sequence represented by SEQ ID NO: 2 includes the following amino acid sequences.

```
                                         (SEQ ID NO: 6)
             ARRYTWIRA (SEQ ID NO: 7)
             AmRRYTWIRA (SEQ ID NO: 8)
             ARmRYTWIRA (SEQ ID NO: 9)
             AmRmRYTWIRA
```

X in SEQ ID NO: 3 is either A (an alanine residue) or mA (a methylated alanine residue). In other words, the amino acid sequence represented by SEQ ID NO: 3 includes the following amino acid sequences.

```
                                         (SEQ ID NO: 10)
             RAWRQCRWR (SEQ ID NO: 11)
             RmAWRQCRWR
```

In general formula (I), $X^{11}$ may be a peptide residue composed of an amino acid sequence of (b) described below, which represents a peptide residue that is functionally equivalent to the peptide residue composed of an amino acid sequence of (a) described above.

(b) An amino acid sequence including a sequence in which one or two amino acids have been deleted, substituted or added in an amino acid sequence represented by any of SEQ ID NOs: 1 to 3.

In this description, the term "substituted" means substitution with another amino acid residue having a chemically similar side chain. Groups of amino acid residues having chemically similar amino acid side chains are well known in the technical field to which polypeptides obtained using the production method of an embodiment of the present invention belong. For example, among acidic amino acids (aspartic acid and glutamic acid), basic amino acids (lysine, arginine and histidine) and neutral amino acids, classification can be made into amino acids having a hydrocarbon chain (glycine, alanine, valine, leucine, isoleucine and proline), amino acids having a hydroxyl group (serine and threonine), amino acids containing sulfur (cysteine and methionine), amino acids having an amide group (asparagine and glutamine), amino acids having an imino group (proline), and amino acids having an aromatic group (phenylalanine, tyrosine and tryptophan) and the like. The most commonly occurring amino acid substitutions include, for example, alanine/serine, valine/isoleucine, aspartic acid/glutamic acid, threonine/serine, alanine/glycine, alanine/threonine, serine/asparagine, alanine/valine, serine/glycine, tyrosine/phenylalanine, alanine/proline, lysine/arginine, aspartic acid/asparagine, leucine/isoleucine, leucine/valine, alanine/glutamic acid, and aspartic acid/glycine.

Moreover specifically, in the amino acid sequences represented by SEQ ID NO: 1 or 4, possible substitutions that can be envisaged include substitution of the arginine first from the N-terminus with glycine, alanine, lysine, serine, threonine or histidine, substitution of the lysine second from the C-terminus with glycine, alanine, arginine, histidine, serine or threonine, and substitution of the proline first from the C-terminus with glycine, alanine, serine, threonine, valine, leucine or isoleucine.

Specific examples of peptide residues composed of an amino acid sequence of (b) described above include peptide residues composed of amino acid sequences represented by SEQ ID NO: 13 and SEQ ID NO: 14. As illustrated in the examples described below, in the amino acid sequence represented by SEQ ID NO: 4, the amino acid residue composed of R-P-T-T-W-H (SEQ ID NO: 12) is essential for achieving a high degree of accumulation in cancer cells or cancer tissue in the digestive system. Consequently, by ensuring that $X^{11}$ is a peptide residue composed of an amino acid sequence represented by SEQ ID NO: 13 or SEQ ID NO: 14, a high degree of accumulation in cancer cells or cancer tissue in the digestive system can be achieved.

(SEQ ID NO: 13)
RPTTWHKP (SEQ ID NO: 14)
RRPTTWH

Further, the peptide residue composed of an amino acid sequence of (a) or (b) above may be composed of L-amino acids, D-amino acids, or a combination thereof. Among the various possibilities, $X^{11}$ is preferably a peptide residue composed of L-amino acids.

L-amino acids are amino acids that exist in nature, whereas a D-amino acid is an amino acid in which the chirality of an L-amino acid residue has been reversed. Further, in order to enhance the high degree of accumulation in cancer cells or cancer tissue in the digestive system, or in order to optimize other physical properties, the amino acid residues that constitute the peptide residue composed of an amino acid sequence of (a) or (b) above may be subjected to chemical modification such as methylation.

[$X^{12}$]

In general formula (I), $X^{12}$ is either a peptide residue composed of an amino acid sequence of (a) or (b) above, or a retro-inverso peptide residue thereof.

In this description, a "retro-inverso peptide residue" means a peptide residue in which the amino acid sequence is reversed, and substituted with optical isomer amino acid residues.

Among the various possibilities, from the viewpoint of further enhancing the high degree of accumulation in cancer cells or cancer tissue in the digestive system, $X^{12}$ is preferably a peptide residue having the same amino acid sequence as $X^{11}$. Further, from the viewpoint of achieving superior degradation resistance in vivo, $X^{12}$ is preferably a retro-inverso peptide residue of $X^{11}$.

[$Y^{11}$]

In general formula (I), $Y^{11}$ is a peptide linker composed of an amino acid residue of at least 1 but not more than 10 amino acids. Each amino acid residue that constitutes $Y^{11}$ is independently a glycine residue, a proline residue, a serine residue, a cysteine residue or a lysine residue. The number of amino acids in $Y^{11}$ is preferably at least 1 but not more than 5, more preferably at least 1 but not more than 3, and even preferably 1.

Among the various possibilities, $Y^{11}$ is preferably a peptide linker composed of an amino acid residue of at least 1 but not more than 10 amino acids, wherein each amino acid residue is independently a glycine residue, a cysteine residue or a lysine residue, and is more preferably a peptide linker composed of an amino acid residue having one amino acid, wherein the amino acid residue is a glycine residue, a cysteine residue or a lysine residue. In those cases where the amino acid residue that constitutes $Y^{11}$ is a cysteine residue or a lysine residue, a target substance described below can be bonded covalently to the peptide of the present embodiment via the thiol group (—SH) of the cysteine residue or the side chain of the lysine residue.

[n11]

In general formula (I), n11 represents an integer of at least 1 but not more than 9, and is preferably an integer of at least 1 but not more than 8, more preferably an integer of at least 1 but not more than 6, even more preferably an integer of at least 1 but not more than 4, particularly preferably an integer of at least 1 but not more than 3, and most preferably an integer of at least 1 but not more than 2.

In the peptide of the present embodiment, specific examples of preferred forms of the amino acid sequence (I) include the amino acid sequences shown below in Table 1. It should be noted that these amino acid sequences are merely examples of preferred forms of the amino acid sequence (I), and preferred forms of the amino acid sequence (I) are not limited to these particular sequences. In the amino acid sequences represented by SEQ ID NO: 18, SEQ ID NO: 19, SEQ ID NO: 25, SEQ ID NO: 26, SEQ ID NO: 27 and SEQ ID NO: 28 in Table 1, the "mR" second from the N-terminus indicates a methylated arginine residue.

TABLE 1

| Amino acid sequence | SEQ ID NO |
|---|---|
| RRPTTWHKP-G-RRPTTWHKP | 15 |
| RRPTTWHKP-G-RRPTTWHKP-G-RRPTTWHKP | 16 |
| RRPTTWHKP-G-pkhwttprr | 17 |
| R-mR-PTTWHKP-G-RRPTTWHKP | 18 |
| R-mR-PTTWHKP-G-pkhwttprr | 19 |
| RPTTWHKP-G-RPTTWHKP | 20 |
| RPTTWHKP-G-RRPTTWHKP | 21 |
| RRPTTWH-G-RRPTTWH | 22 |
| RRPTTWH-G-RRPTTWHKP | 23 |
| RRPTTWHKP-G-RRPTTWH | 24 |
| R-mR-PTTWHKP-G-RRPTTWH | 25 |
| R-mR-PTTWH-G-RRPTTWHKP | 26 |
| R-mR-PTTWHKP-C-RRPTTWHKP | 27 |
| R-mR-PTTWHKP-C-RRPTTWHKP-G-RRPTTWHKP | 28 |
| RPTTWHKP-G-RRPTTWHKP-C-RRPTTWHKP | 29 |
| RPTTWHKP-C-RRPTTWHKP-C-RRPTTWHKP | 30 |
| RPTTWHKP-G-RRPTTWHKP-K-RRPTTWHKP | 31 |

The peptide of the present embodiment can be used favorably as a delivery agent for simply, efficiently and continuously delivering a target material that is either internally incorporated within the peptide or bonded to the peptide to cancer cells or cancer tissue in the digestive system in a stable manner in vivo (in a state where in vivo degradation resistance is maintained for about 12 hours).

<Method for Producing Peptide>

The peptide of an embodiment of the present invention may be produced using chemical synthesis methods, or may be produced using biological methods. Examples of the chemical methods include peptide solid-phase synthesis methods (such as the Boc solid-phase synthesis method and Fmoc solid-phase synthesis method). Examples of biological methods include methods using cell-free peptide synthesis systems or living cell peptide synthesis systems that employ an expression vector having a nucleic acid that encodes the peptide. Details regarding cell-free peptide synthesis systems and living cell peptide synthesis systems are described below.

<Nucleic Acid>

A nucleic acid of an embodiment of the present invention is a nucleic acid that encodes the peptide according to the embodiment described above.

By using the nucleic acid according to this embodiment, a peptide having a high degree of accumulation in cancer cells or cancer tissue in the digestive system, and excellent degradation resistance in vivo can be obtained.

Examples of the nucleic acid that encodes the peptide described above include nucleic acids composed of a base sequence represented by any of SEQ ID NOs: 32 to 34, or nucleic acids having any base sequence that is at least 80% identical, for example at least 85% identical, at least 90% identical or at least 95% identical, with a base sequence represented by any of SEQ ID NOs: 32 to 34, and has a combination that encodes each of the amino acids that function as constituent components of a peptide having a high degree of accumulation in cancer cells or cancer tissue in the digestive system, and excellent in vivo degradation resistance. The base sequence represented by SEQ ID NO: 32 is the base sequence of a nucleic acid that encodes a peptide composed of an amino acid sequence represented by the above SEQ ID NO: 15. The base sequence represented by SEQ ID NO: 33 is the base sequence of a nucleic acid that encodes a peptide composed of an amino acid sequence represented by the above SEQ ID NO: 16. The base sequence represented by SEQ ID NO: 34 is the base sequence of a nucleic acid that encodes a peptide composed of an amino acid sequence represented by the above SEQ ID NO: 17.

The sequence identity of the target base sequence relative to the reference base sequence can be determined, for example, in the following manner. First, the reference base sequence and the target base sequence are aligned. Here, each base sequence may include gaps so as to maximize the sequence identity. Subsequently, in the reference base sequence and the target base sequence, the number of matching bases is calculated, and the sequence identity can then be determined using the formula shown below.

Sequence identity (%)=[number of matching bases]/ [total number of bases in target base sequence]× 100

The nucleic acid of the present embodiment may be incorporated within a vector. The vector is preferably a protein expression vector. There are no particular limitations on the expression vector, and examples of expression vectors that may be used include plasmids derived from *E. coli*, plasmids derived from *Bacillus subtilis*, plasmids derived from yeast, bacteriophages, virus vectors, and modified vectors thereof. Examples of the plasmids derived from *E. coli* include pBR322, pBR325, pUC12 and pUC13. Examples of the plasmids derived from *Bacillus subtilis* include pUB110, pTP5, and pC194. Examples of the plasmids derived from yeast include pSH19 and pSH15. Examples of the bacteriophages include λ phage. Examples of viruses that yield virus vectors include adenovirus, adeno-associated virus, lentivirus, vaccinia virus, baculovirus, retrovirus and hepatitis virus.

In the above expression vector, there are no particular limitations on the promoter for the peptide expression, which may be an expression promoter that uses animal cells as a host, an expression promoter that uses plant cells as a host, or an expression promoter that uses insect cells as a host. Examples of expression promoters that use animal cells as a host include an EF1α promoter, SRα promoter, SV40 promoter, LTR promoter, CMV (cytomegalovirus) promoter, HSV-tk promoter and CAG promoter. Examples of expression promoters that use plant cells as a host include a cauliflower mosaic virus (CaMV) 35S promoter and an REF (rubber elongation factor) promoter. Examples of expression promoters that use insect cells as a host include a polyhedrin promoter and p10 promoter. These promoters may be selected appropriately in accordance with the type of host used for expressing the peptide.

The expression vector described above may further have a multicloning site, an enhancer, a splicing signal, a poly A addition signal, a selection marker, or a replication origin or the like.

The expression vector preferably has an added nucleic acid or separate target gene that encodes a stuffer protein such as green fluorescent protein (GFP) or glutathione-S- transferase (GST) (wherein the protein itself has low toxicity and exhibits no inherent function) either upstream or downstream from the nucleic acid that encodes the above peptide. This enables more efficient production of a fusion protein in which the above peptide is fused to the stuffer protein. Further, in the case of incorporation within an expression vector having an extracellular protein secretion signal, a fusion protein having the added amino acid sequence of the peptide can be produced in the culture solution and collected. Furthermore, even in the case of an intracellular expression vector, the same peptide-added fusion protein can still be produced.

By using an expression vector having a nucleic acid according to the present embodiment and suitable host cells, the peptide described above can be expressed.

<Modulator>

The peptide of an embodiment of the present invention may be modified with a modulator separately from the target substance described below. Examples of the modulator include sugar chains and polyethylene glycol (PEG). Further, liposomes, viruses, dendrimers, antibodies (immunoglobulins), exosomes, and polymer micelles and the like may also be used as modulators. In other words, the peptide of an embodiment of the present invention can be used in a form bonded to the expression of a liposome, virus, exosome or polymer micelle, a form in which either one, or a plurality of two or more of the peptides are bonded to the side-chain portion of a dendrimer, or a form in which an antibody (immunoglobulin) and the peptide are bonded together.

Examples of the dendrimer include poly(amidoamine) (PAMAM) dendrimers, polypropyleneimine dendrimers, polylysine dendrimers, polyphenyl ether dendrimers, and polyphenylene dendrimers. By using these dendrimers, from several tens of molecules through to one hundred and several tens of molecules of the peptide can be delivered simultaneously to cancer cells or cancer tissue in the digestive system.

Further, by modifying the peptide of an embodiment of the present invention with a modulator described above, a target substance (for example, a biologically active substance or labeling substance) can be absorbed more easily and more efficiently in cancer cells or cancer tissue in the digestive system. The peptide that has been modified with the modulator (hereafter sometimes abbreviated as a "modified peptide") can be prepared, for example, by physically or chemically bonding the modulator and the peptide, either directly or via a linker. Specific examples of the bonding method include coordination bonding, covalent bonding, hydrogen bonding, hydrophobic interactions and physical adsorption, and any conventional bonding, linkers or bonding methods may be employed. Further, the modulator bonding position may be either the N-terminus or the C-terminus of the peptide. Furthermore, in those cases where the peptide contains a lysine residue, the modulator may also be bonded to a side-chain site on the lysine residue.

<Target Substance>

The target substance may be selected appropriately in accordance with the intended application, and for example, in the case of use for imaging cancer cells or cancer tissue in the digestive system, a labeling substance may be used as the target substance, in the manner described below. Further, for example, in the case of use in an application for the treatment of a disease (for example, cancer) of the digestive system, a biologically active substance (and in particular an anticancer drug) may be used as the target substance, in the manner described below. The peptide of an embodiment of the present invention can be used to deliver a single type of these target substances, or may be used to deliver a combination of two or more types of target substances.

The target substance may be bonded physically or chemically to the peptide, either directly or via a linker. Specific examples of the bonding method include coordination bonding, covalent bonding, hydrogen bonding, hydrophobic interactions and physical adsorption, and any conventional bonding, linkers or bonding methods may be employed. Further, the bonding position between the target substance and the peptide of an embodiment of the present invention may be selected appropriately according to need. Moreover, even in those cases where there is no physical or chemical bonding, a state in which the steric structure causes one of the molecules to restrict movement of the other molecule so that the two move together is included within the definition of a bonded state in this embodiment.

In those cases where the target substance is a protein, a fusion protein containing the target substance and the peptide can be produced, for example, in the following manner. First, an expression vector containing a nucleic acid that encodes the fusion protein is used to transform a host. Subsequently, the host is cultured to express the fusion protein. Conditions such as the composition of the culture medium, the culture temperature, the time, and the addition of an inducer and the like may be determined by those skilled in the art based on conventional methods so that the transformant grows and the fusion protein is produced efficiently. For example, when an antibiotic-resistant gene is incorporated into the expression vector as a selection marker, the transformant can be selected by adding an antibiotic to the medium. Subsequently, by purifying the fusion protein expressed by the host using an appropriate method, the fusion protein can be obtained.

There are no particular limitations on the host, provided it is composed of living cells capable of expressing an expression vector containing a nucleic acid that encodes the fusion protein. Examples of the host include mammalian cell lines such as Chinese hamster ovary (CHO) cells, viruses (for example, viruses such as adenovirus, adeno-associated virus, lentivirus, vaccinia virus, baculovirus, retrovirus and hepatitis virus), microorganisms such as bacteria (for example, *E. coli*), and living cells such as yeast cells, insect cells and plant cells.

Next, a peptide-drug conjugate (PDC), a pharmaceutical composition, a labeled peptide and an imaging composition each containing the peptide of an embodiment of the present invention are described below in detail.

<<Peptide-Drug Conjugate (PDC)>>

A PDC of an embodiment of the present invention contains the peptide described above and a biologically active substance.

The PDC of this embodiment can selectively treat cancer of the digestive system (and particularly invasive pancreatic ductal adenocarcinoma).

In this description, there are no particular limitations on the "biologically active substance", provided it is effective in treating human cancer, and examples include drugs such as anticancer drugs, nucleic acids, proteins having a cell growth inhibiting effect or a cytotoxic effect, antibodies or antibody fragments thereof that bind specifically to cancer cells (and particularly pancreatic cancer cells) (and particularly antibodies or antibody fragments thereof or the like that target the antigens that exist on the cell membranes of pancreatic cancer cells), and aptamers.

For example, an antibody or antibody fragment thereof mentioned above may be bonded to the N-terminus or C-terminus of the peptide described above via a mediator such as a linker or via an amino acid sequence used as a spacer, or the peptide described above may be bonded to any site or a plurality of sites in the Fc domain of the antibody or antibody fragment thereof, thus forming an antibody-peptide conjugate. Because this antibody-peptide conjugate can bind not only to cell membrane surface antigens recognized by the antibody, but can simultaneously bind to cell membrane surface receptors recognized by the peptide, the delivery function to the targeted cells (pancreatic cancer cells in the present embodiment) can be enhanced. Furthermore, in those cases where the antibody or antibody fragment thereof is a single-chain antibody (ScFv) capable of reacting with an intracellular antigen, by preparing an expression vector having a sequence that encodes the above peptide added to a nucleic acid that encodes the ScFv, a single-chain antibody having a delivery function to the target cells (pancreatic cancer cells in the present embodiment) can be produced.

The "biologically active substance" is preferably a cytotoxic drug or molecular targeted drug that functions as an anticancer drug. Because the peptide described above exhibits absorption shifted to a high degree toward cancer cells or cancer tissue in the digestive system (and particularly pancreatic cancer cells or pancreatic cancer tissue) compared with normal cells and normal tissue, when the peptide is conjugated to form a PDC with a cytotoxic drug used as a conventional anticancer drug as the biologically active substance, that cytotoxic drug can be delivered efficiently to the cancer cells or cancer tissue.

The biologically active substance and the peptide are preferably bonded together to form a conjugate. Here, the term "conjugate" describes a state where two or more substances are able to move together, and includes cases where the substances are boned together by covalent boding, cases where the substances are electrostatically bonded by ionic bonding, and cases in which even if no bonding exists, the steric structure causes one of the substances to restrict movement of another substance so that the substances can move together. For example, cases in which the biologically active substance is enclosed within a liposome, virus, exosome, or polymer micelle or the like that has been used to modify the surface of the peptide are also included in cases of "conjugate" formation. Among the various possibilities, in order to inhibit dissociation of the biologically active substance prior to reaching the target site, the bonding between the biologically active substance and the peptide is preferably composed of covalent bonding.

Specific examples of methods for forming covalent bonding between the biologically active substance and the peptide include methods that employ coupling reactions, either directly or via a linker, of the biologically active substance with an arbitrary site on the peptide having a functional group or with an introduced functional group such as —OH, —SH, —$CO_2H$, —$NH_2$, —$SO_3H$ or $PO_2H$. In a more specific example, an SH group (thiol group) is introduced into the peptide and a maleimide group is introduced into the biologically active substance, and the SH group of the peptide and the maleimide group of the biologically active substance are then bonded together, thereby bonding the peptide and the biologically active substance.

There are no particular limitations on the linker, provided it enables the functions of the biologically active substance and the peptide to be maintained, and is capable of passing through the cell membrane with the peptide. Specific examples of the linker include peptide chains having a length that is typically at least 1 residue but not more than 5 residues, and preferably at least 1 but not more than about 3 residues, and polyethylene glycol (PEG) chains of the same length.

The amino acid residue(s) that constitute the peptide linker used in conjugating the peptide and the biologically active substance are preferably residues that have no charge and a small molecular size, such as a glycine residue. Further, a residue that imparts freedom of rotation of the two bonded domains (the biologically active substance and the peptide) is preferably provided at the terminus, and preferably at both termini, of the linker sequence. Specifically, in order to impart freedom of rotation, a sequence containing glycine (G) and containing proline (P) as a linker is preferred, and more specifically, a sequence compose solely of glycine residues and a proline residue, for example, glycine (G)-proline (P)-glycine (G), is particularly preferred. By using such a configuration, the functions of both domains can be realized. Alternatively, in terms of facilitating formation of covalent bonds, the termini of the linker sequence preferably include cysteine (C) or lysine (K). The biologically active substance can then be bonded to the peptide via the thiol group (—SH) of the cysteine residue or the side chain of the lysine residue.

In those cases where the biologically active substance is a protein, when the biologically active substance and the peptide are conjugated, the conjugate may be prepared as a fusion protein. Although there are no particular limitations on the position at which the peptide is provided, it is preferable that the peptide is presented outside the protein and has little effect on the activity and functionality of the fusion protein, and is preferably fused at the N-terminus or the C-terminus of the protein that represents the biologically active substance. Although there are no particular limitations on the type of protein that is fused, because drugs that have a molecular weight that is too large are inhibited in terms of passage through the cell membrane, the molecular weight is typically not more than about 500,000, and may be restricted to not more than about 30,000.

The protein used as the biologically active substance may be an antibody. Such antibodies can be prepared, for example, by immunizing a rodent animal such as a mouse with a peptide or the like derived from a cancer of the digestive system as an antigen. Further, antibodies may also be prepared by screening of a phage library. The antibody may be an antibody fragment, and examples of such antibody fragments include Fv, Fab, and scFv and the like.

Examples of nucleic acids that may be used as the biologically active substance include siRNA, miRNA, antisense, or artificial nucleic acids or the like that compensate for these functions.

Aptamers that may be used as the biologically active substance are substances having a specific binding ability to cancer cells or cancer tissue of the digestive system. Examples of aptamers include nucleic acid aptamers and peptide aptamers. Nucleic acid aptamers having a specific binding ability to cancer cells or cancer tissue of the digestive system can be selected, for example, by the systematic evolution of ligand by exponential enrichment (SELEX) method. Peptide aptamers having a specific binding ability to cancer cells or cancer tissue of the digestive system can be selected, for example, by the two-hybrid method using yeast.

In the PDC of the present embodiment, the peptide may be modified using a modulator in the manner described above, and may also incorporate a labeling substance.

<<Pharmaceutical Composition>>

A pharmaceutical composition of an embodiment of the present invention contains the PDC described above.

The pharmaceutical composition of this embodiment can be used for treatment of cancer of the digestive system, or for treatment of diseases associated with cancer of the digestive system. Examples of diseases associated with cancer of the digestive system include metastatic cancer (lymph node metastasis or peritoneal metastasis (disseminated)) in which the primary lesion is a cancer of the digestive system.

<Composition Components>

The pharmaceutical composition of the present embodiment contains a therapeutically effective amount of the above PDC, and a pharmaceutically acceptable carrier or diluent. Pharmaceutically acceptable carriers or diluents include excipients, extenders, disintegrants, stabilizers, preservatives, buffers, emulsifiers, fragrances, colorants, sweeteners, thickeners, flavoring agents, and solubilizers and the like. By using one or more of these carriers or diluents, pharmaceutical compositions in the form of injections, solutions, capsules, suspensions, emulsions, and syrups and the like can be prepared.

Further, a colloidal dispersion system can also be used as the carrier. Colloidal dispersion systems can be expected to have an effect in enhancing the in vivo stability of the peptide or the PDC, and an effect in enhancing the transferability of the peptide or the PDC into cancer cells or cancer tissue in the digestive system. Examples of colloidal dispersion systems include polyethylene glycol, polymer composites, polymer aggregates, nanocapsules, microspheres, beads, oil-in-water emulsifiers, micelles, mixed micelles, and lipids containing liposomes, and among these, liposomes and artificial membrane vesicles, which are effective in efficiently transporting the peptide or the PDC, are preferred.

Examples of the formulation for the pharmaceutical composition of the present embodiment include oral formulations such as tablets which may be sugar-coated as necessary, capsules, elixirs, and microcapsules.

Other examples include parenteral formulations in the form of sterile solutions with either water or another pharmaceutically acceptable liquid, or injectable suspensions.

Moreover, formulations may also be prepared by appropriate combination with a pharmacologically acceptable carrier or diluent, specifically a vehicle (such as sterilized water, physiological saline or vegetable oil), or an emulsifier, suspension, surfactant, stabilizer, flavoring agent, excipient, preservative or binder or the like, and then mixing with a unit dosage form typically required in pharmaceutical practice.

Examples of carriers or diluents that may be mixed into tablets or capsules include binders, excipients, swelling agents, lubricants, sweeteners and flavoring agents. Examples of the binders include gelatin, corn starch, tragacanth gum and gum arabic. Examples of the excipients include crystalline cellulose and the like. Examples of the swelling agents include corn starch, gelatin and alginic acid. Examples of the lubricants include magnesium stearate and the like. Examples of the sweeteners include sucrose, lactose and saccharin. Examples of the flavoring agents include peppermint refined oil, oil of *Gaultheria adenothrix* and cherry flavoring. When the dispensed unit form is a capsule, the above material may further contain a liquid carrier such as an oil or fat.

Sterile compositions for injection can be formulated according to normal pharmaceutical practice using a vehicle such as distilled water for injection.

Examples of aqueous solution vehicles for injection include isotonic solutions containing physiological saline, glucose and other adjuvants, and suitable solubilizers and nonionic surfactants and the like may also be added. Examples of the other adjuvants include D-sorbitol, D-mannose, D-mannitol and sodium chloride. Examples of the solubilizers include alcohols. Specific examples of the alcohols include ethanol and polyalcohols. Examples of these polyalcohols include propylene glycol and polyethylene glycol. Examples of the nonionic surfactants include Polysorbate 80 (a registered trademark) and HCO-50.

Examples of vehicles for non-aqueous solutions for injection include sesame oil and soybean oil, which may be used in combination with benzyl benzoate or benzyl alcohol as a solubilizer. Further, buffering agents, soothing agents, stabilizers, and antioxidants and the like may also be blended into the oil-based solution for injection. Examples of the buffering agents include a phosphate buffer and a sodium acetate buffer. Examples of the soothing agents include procaine hydrochloride and the like. Examples of the stabilizers include benzyl alcohol and phenol. The prepared injection solution is typically loaded into a suitable ampoule.

In the case of an injection, the injection may be prepared as an aforementioned aqueous or non-aqueous solution, suspension or emulsion. Sterilization of these types of injections can be performed by filtration sterilization using a filter, or by the addition of an antimicrobial agent or the like. Injections can be produced in forms that are prepared at the time of use. In other words, the formulation can be stored as a sterile solid composition by freeze drying or the like, and then dissolved in distilled water for injection or another vehicle prior to use.

<Dosage>

The pharmaceutical composition of the present embodiment is prepared appropriately with due consideration of the type of biologically active substance included in the PDC, and factors such as the age, gender, weight, symptoms, treatment method, administration method and treatment time of the test subject (any of various mammals including humans and non-human animals, but preferably a human).

For example, when the pharmaceutical composition of the present embodiment is injected intravenously (i.v.), at least 0.1 mg but not more than about 1,000 mg of the PDC may be administered in a single administration per 1 kg of body weight of the test subject (preferably a human).

Examples of the dosage form include intraarterial injections, intravenous injections, subcutaneous injections, as well as administration by intranasal, intraperitoneal, transbronchial, intramuscular, transdermal or oral methods known to those skilled in the art. Intravenous injection or intraperitoneal administration is preferred.

<Treatment Method>

In one embodiment, the present invention provides a pharmaceutical composition containing the PDC described above, which is used for the treatment or prevention of cancer of the digestive system (and particularly pancreatic cancer).

Further, in one embodiment, the present invention provides a pharmaceutical composition containing a therapeutically effective amount of the above PDC and a pharmaceutically acceptable carrier or diluent.

Furthermore, in one embodiment, the present invention provides use of the PDC described above for producing a pharmaceutical composition for the treatment or prevention of cancer of the digestive system (and particularly pancreatic cancer).

Furthermore, in one embodiment, the present invention provides a treatment method or prevention method for cancer of the digestive system (and particularly pancreatic cancer) that includes administering an effective amount of the PDC described above to a patient requiring treatment.

<<Labeled Peptide>>

A labeled peptide of an embodiment of the present invention contains the peptide described above and a labeling substance.

<Labeling Substance>

Examples of the labeling substance include stable isotopes, radioisotopes, fluorescent substances, positron emission tomography (PET) nuclides, single photon emission computed tomography (SPECT) nuclides, magnetic resonance imaging (MRI) contrast agents, computed tomography (CT) contrast agents, and magnetic substances. Further, in those cases where the labeling substance is a protein, a fusion protein of the labeling substance and the peptide may be used. Among the various options, a stable isotope, radioisotope or fluorescent substance is preferred. By including the labeling substance, a determination as to whether or not the labeled peptide has been delivered to the cancer cells or cancer tissue in the digestive system can be made simply and with high sensitivity.

Examples of stable isotopes include $^{13}$C (carbon 13), $^{15}$N (nitrogen 15), $^{2}$H (hydrogen 2), $^{17}$O (oxygen 17) and $^{18}$O (oxygen 18). Examples of radioisotopes include $^{3}$H (hydrogen 3), $^{14}$C (carbon 14), $^{13}$N (nitrogen 13), $^{18}$F (fluorine 18), $^{32}$P (phosphorus 32), $^{33}$P (phosphorus 33), $^{35}$S (sulfur 35), $^{67}$Cu (copper 67), $^{99m}$Tc (technetium 99m), $^{123}$I (iodine 123), $^{131}$I (iodine 131), $^{133}$Xe (xenon 133), $^{201}$Tl (thallium 201), and $^{67}$Ga (gallium 67).

In those cases where the labeling substance is a stable isotope or a radioisotope, the labeled peptide may be prepared using a stable isotope-labeled amino acid or a radioisotope-labeled amino acid. In other words, in the labeled peptide of the present embodiment, the expression "contains the peptide described above and a labeling substance" includes the case of a peptide produced using a stable isotope-labeled amino acid or a radioisotope-labeled amino acid.

There are 20 types of amino acids that may be labeled with a stable isotope or a radioisotope (alanine, arginine, aspartic acid, glutamic acid, glycine, histidine, isoleucine, leucine, lysine, methionine, phenylalanine, proline, serine, threonine, tyrosine, valine, tryptophan, cysteine, asparagine and glutamine), and any of the amino acids included in the peptide may be labeled without any particular limitations. Further, the amino acid may be an L-form or a D-form, any may be selected appropriately as required.

The labeled peptide of the present embodiment produced using a stable isotope-labeled amino acid or a radioisotope-labeled amino acid can be prepared by expressing a vector containing the nucleic acid that encodes the peptide in a system in which a stable isotope-labeled amino acid or a radioisotope-labeled amino acid is present. Examples of systems in which a stable isotope-labeled amino acid or a radioisotope-labeled amino acid is present include cell-free peptide synthesis systems and living cell peptide synthesis systems in which a stable isotope-labeled amino acid or a radioisotope-labeled amino acid is present. In other words, by synthesizing the peptide in a cell-free peptide synthesis system using a stable isotope-labeled amino acid or a radioisotope-labeled amino acid as well as the stable isotope-unlabeled amino acid(s) or radioisotope-unlabeled amino acid(s), or in the case of a living cell peptide synthesis system, by culturing cells that have been transformed by a vector containing a nucleic acid that encodes the peptide in the presence of a stable isotope-labeled amino acid or a radioisotope-labeled amino acid, a peptide that has been labeled with the stable isotope or the radioisotope can be prepared from the vector containing the nucleic acid that encodes the peptide.

Expression of the peptide that has been labeled with a stable isotope or a radioisotope using a cell-free peptide synthesis system can be conducted using, besides the vector containing a nucleic acid that encodes the peptide and the aforementioned stable isotope-labeled amino acid or radioisotope-labeled amino acid, any stable isotope-unlabeled amino acids or radioisotope-unlabeled amino acids required for the synthesis of the peptide labeled with a stable isotope or a radioisotope, a cell extract for cell-free peptide synthesis, and an energy source (a high-energy phosphate bond-containing material such as ATP, GTP or creatine phosphate). The reaction conditions such as the temperature and time may be selected as appropriate, and for example, the temperature may be set to at least 20° C. but not more than 40° C., and preferably at least 23° C. but not more than 37° C. Further, the reaction time may be set to at least 1 hour but not more than 24 hours, and is preferably at least 10 hours but not more than 20 hours.

In this description, the term "cell extract for cell-free peptide synthesis" means an extract from plant cells, animal cells, fungal cells or bacterial cells that contains components required for a translation system, or a transcription system and translation system, that participates in the synthesis of proteins such as ribosomes or tRNA. Specific examples include cell extracts of *E. coli*, wheat germ, rabbit reticulocytes, mouse L-cells, Ehrlich ascites tumor cells, HeLa cells, CHO cells, and budding yeast. Preparation of these cell extracts may be performed, for example, in accordance with the method described in Pratt, J M. et al., Transcription and Translation-A Practical Approach (1984), pp. 179 to 209, by disrupting the above cells using a French press, glass beads, or an ultrasonic disruptor or the like, adding a buffer containing several types of salts to solubilize the protein components and ribosomes, homogenizing the resulting mixture, and then precipitating the insoluble components by centrifugal separation.

Furthermore, expression of the aforementioned peptide that has been labeled with a stable isotope or a radioisotope using a cell-free peptide synthesis system may also be conducted by appropriate use of a commercially available kit such as a Premium Expression Kit with a wheat germ extract (manufactured by CellFree Sciences Co., Ltd.), an RTS 100, an *E. coli* HY Kit with an *E. coli* extract (manufactured by Roche Applied Science, Inc.), or a cell-free Quick (manufactured by Taiyo Nippon Sanso Corporation). In those cases where the expressed stable isotope-labeled or radioisotope-labeled peptide is insoluble, the peptide may be solubilized appropriately using a protein denaturant such as guanidine hydrochloride or urea. The stable isotope-labeled or radioisotope-labeled peptide may be further purified by a fractionation treatment using a fractional centrifugation method or sucrose density gradient centrifugation method or the like, or by affinity column purification or ion exchange chromatography.

Expression of the aforementioned peptide that has been labeled with a stable isotope or a radioisotope using a living cell peptide synthesis system can be conducted by introducing a vector containing a nucleic acid that encodes the peptide into the living cells, and then culturing the living cells in a culture solution containing nutrients and an antibiotic and the like, as well as the aforementioned stable isotope-labeled amino acid or radioisotope-labeled amino acid, and any stable isotope-unlabeled amino acids or radioisotope-unlabeled amino acids required for the synthesis of the stable isotope-labeled peptide or radioisotope-labeled peptide. There are no particular limitations on the living cells, provided they are living cells capable of expressing the vector containing the nucleic acid that encodes the peptide, and examples include mammalian cell lines such as Chinese hamster ovary (CHO) cells, E. coli, yeast cells, insect cells and plant cells, and if consideration is given to simplicity and cost effectiveness, then E. coli is preferred. Expression of the vector containing the nucleic acid that encodes the above peptide can be performed by using gene recombination technology to assemble an expression vector designed to be capable of expression in the selected living cells, and then introducing that expression vector into the living cells. Further, the introduction into living cells of the vector containing the nucleic acid that encodes the peptide may be conducted using a method suited to the living cells being used, such as an electroporation method, heat shock method, calcium phosphate method, lipofection method, DEAE dextran method, microinjection method, particle gun method, a method using a virus, or a method using a commercially available transfection reagent such as FuGENE (a registered trademark) 6 Transfection Reagent (manufactured by Roche Holding AG), Lipofectamine 2000 Reagent (manufactured by Invitrogen Corporation), Lipofectamine LTX Regent (manufactured by Invitrogen Corporation), or Lipofectamine 3000 Reagent (manufactured by Invitrogen Corporation).

The stable isotope-labeled or radioisotope-labeled peptide described above expressed by a living cell peptide synthesis system can be prepared by disruption and extraction of the living cells containing the stable isotope-labeled or radioisotope-labeled peptide. Examples of the disruption treatment include physical disruption treatments using a freeze-thaw method, a French press, glass beads, a homogenizer, or an ultrasonic disruptor or the like. Further, examples of the extraction treatment include extraction treatments using a protein denaturant such as guanidine hydrochloride or urea. The stable isotope-labeled or radioisotope-labeled peptide may be further purified by a fractionation treatment using a fractional centrifugation method or sucrose density gradient centrifugation method or the like, or by affinity column purification or ion exchange chromatography.

Examples of the fluorescent substance include conventional quantum dots, indocyanine green, 5-aminolevulinic acid (5-ALA; metabolite protoporphyrin IX (PP IX)), near-infrared (NIR) fluorescent dyes (such as Cy5.5, Cy7, and AlexaFluoro), and other known fluorescent dyes (such as GFP, FITC (Fluorescein), FAM and TAMRA). In those cases where the fluorescent substance is a protein, the fluorescent substance-labeled peptide described above may be obtained by preparing an expression vector containing a nucleic acid that encodes the fluorescent substance and a nucleic acid that encodes the peptide in either an aforementioned cell-free peptide synthesis system or a living cell peptide synthesis system without using a stable isotope-labeled amino acid or radioisotope-labeled amino acid.

Examples of preferred PET nuclides and SPECT nuclides include $^{11}C$, $^{13}N$, $^{15}O$, $^{18}F$, $^{66}Ga$, $^{67}Ga$, $^{68}Ga$, $^{60}Cu$, $^{61}Cu$, $^{62}Cu$, $^{67}Cu$, $^{64}Cu$, $^{48}V$, Tc-99m, $^{241}Am$, $^{55}Co$, $^{57}Co$, $^{153}Gd$, $^{111}In$, $^{133}Ba$, $^{82}Rb$, $^{139}Ce$, Te-123m, $^{137}Cs$, $^{86}Y$, $^{90}Y$, $^{185/187}Re$, $^{186/188}Re$, $^{125}I$, as well as complexes thereof and combinations thereof. The peptide described above labelled with either a PET nuclide or a SPECT nuclide can be prepared by physically or chemically bonding the peptide and the PET nuclide or SPECT nuclide, either directly or via a linker. Specific examples of the bonding method include coordination bonding, covalent bonding, hydrogen bonding, hydrophobic interactions and physical adsorption, and any conventional bonding, linkers or bonding methods may be employed.

Examples of the MRI contrast agent, CT contrast agents and magnetic substances include gadolinium, Gd-DTPA, Gd-DTPA-BMA, Gd-HP-DO3A, iodine, iron, iron oxide, chromium, manganese, or a complex thereof, or chelate complex thereof. The peptide labeled with an MRI contrast agent, CT contrast agent or magnetic substance may be prepared by physically or chemically bonding the MRI contrast agent, CT contrast agent or magnetic substance and the peptide, either directly or via a linker. Specific examples of the bonding method include coordination bonding, covalent bonding, hydrogen bonding, hydrophobic interactions and physical adsorption, and any conventional bonding, linkers or bonding methods may be employed.

<Method and Imaging Composition for Imaging Cancer of the Digestive System>

A method according to one embodiment of the present invention is a method for imaging cancer cells or cancer tissue in the digestive system, and uses the labeled peptide described above.

Further, an imaging composition of an embodiment of the present invention contains the labeled peptide described above.

By using the method and the imaging composition of these embodiments, cancer cells or cancer tissue in the digestive system can be detected simply, with high sensitivity and selectivity.

<Composition Components>

The imaging composition of an embodiment of the present invention contains the labeled peptide described above, and may also contain a pharmaceutically acceptable carrier or diluent as required. Examples of the pharmaceutically acceptable carrier or diluent include conventional components typically used in imaging compositions among those components exemplified above for the aforementioned pharmaceutical composition.

For example, in those cases where the labeled peptide described above is added to cancer cells of the digestive system, the amount added of the labeled peptide is preferably at least 1 μM but not more than 10 μM within the culture solution. Further, an evaluation as to whether or not the labeled peptide has been absorbed and accumulated in the cancer cells of the digestive system may be conducted at least 15 minutes but not more than 3 hours after the addition of the peptide.

Further, in those cases where the labeled peptide containing a fluorescent substance as the labeling substance is injected intravenously (i.v.) with an injection, the labeled peptide may be administered, for example, in an amount of at least 0.1 mg but not more than about 1,000 mg in a single administration per 1 kg of body weight of the test subject (preferably a human), and the labeled peptide is preferably administered in an amount of at least 3 mg, more preferably an amount of at least 3 mg but not more than 20 mg, and even more preferably an amount of at least 5 mg but not more than 15 mg.

Furthermore, in those cases where the labeled peptide containing a stable isotope, a PET nuclide or a SPECT nuclide as the labeling substance is injected intravenously (i.v.) with an injection, the administered dosage may be determined from the radiation dose in accordance with the stable isotope, PET nuclide or SPECT nuclide that is used.

In the method of an embodiment of the present invention, examples of the method used for detecting the labeled peptide include PET, SPECT, CT, MRI, detection by endoscope, and detection using a fluorescence detector.

The imaging composition of an embodiment of the present invention can be used for diagnosis of cancer of the digestive system, analysis of the efficacy of treatment for cancer of the digestive system, pathological analysis, or for diagnosis, pathological analysis or analysis of treatment efficacy for diseases associated with cancer of the digestive system.

EXAMPLES

The present invention is described below using a series of examples, but the present invention is not limited by the following examples.

[Reference Example 1] Degradation Test by Human Blood Plasma Using PCPP11

Using the peptide disclosed in International Patent Publication No. 2017/086090, a degradation test was conducted with human blood plasma, and details relating to the peptide and the denaturation pattern over time were analyzed.

Specifically, a peptide composed of the amino acid sequence represented by SEQ ID NO: 1 (hereafter sometimes referred to as "PCPP11") was added to human blood plasma having a concentration of 50% by mass, the mixture was sampled immediately after starting the degradation test (after 0 minutes), and then after 5 minutes, after 10 minutes, after 20 minutes, after 30 minutes, after 60 minutes and after 120 minutes, and the samples were analyzed by MALDI-TOFMS (Matrix Assisted Laser Desorption/Ionization-Time Of Flight Mass Spectrometry). The results are shown in FIG. 1 and Table 2 below. In Table 2, "UK" is an abbreviation for "unknown". Further, the No. shown for each peptide in Table 2 corresponds with the numerical value recorded on the peaks of the graphs shown in FIG. 1.

Based on FIG. 1 and Table 2, it was evident that the persistence time (the time of stable existence) for PCPP11 was less than 20 minutes. Based on these results, it was surmised that, following in vivo administration, PCPP11 would undergo complete degradation in less than 20 minutes.

[Test Example 1] Degradation Tests by Human Blood Plasma Using Peptides Designed with Various Forms of Degradation Resistance Based on PCPP11

Subsequently, in light of the results from Reference Example 1, the amino acid sequence of PCPP11 was modified in an attempt to develop peptides having excellent in vivo degradation resistance while maintaining a high degree of accumulation in pancreatic cancer cells or pancreatic cancer tissue.

Specifically, the six peptides shown below in Table 3 were designed. In Table 3, "FAM-L" is PCPP11 which is labeled with the fluorescent substance FAM at the peptide N-terminus, thereby protecting the N-terminus. Further, "LL" is a tandem peptide in which the amino acid sequence of PCPP11 is repeated with a glycine spacer therebetween. Furthermore, "LLL" is a triplet peptide in which the amino acid sequence of PCPP11 is repeated three times with glycine spacers therebetween. Moreover, "Ld" is an L-D chimeric peptide in which an L-amino acid is used for the amino acid sequence of the first half, and a retro-inverso sequence is then linked thereto using an optical isomer as the amino acid sequence of the latter half.

Furthermore, based on the results of the degradation test of Reference Example 1, it was surmised that the peptide bond between the two arginines first and second from the N-terminus was prone to cleavage. Accordingly, "NmLL" is a peptide in which the arginine second from the N-terminus in the above LL peptide has been substituted with a methyl group-modified arginine in order to impart the peptide bond between the two arginines first and second from the N-terminus with degradation resistance. Further, "NmLd" is an L-D chimeric peptide in which the arginine second from the N-terminus in the above Ld peptide has been substituted with a methyl group-modified arginine in order to impart the peptide bond between the two arginines first and second from the N-terminus with degradation resistance.

TABLE 2

| | Peptide No. | | | | | | | |
|---|---|---|---|---|---|---|---|---|
| | 1 | 2 | 3 | 4 | 5 | 6 | 7 | 8 |
| | Amino acid sequence | | | | | | | |
| | RRPTTWHKP | RPTTWHKP | RRPTTWH | RPTTWH | TTWHKP | TTWH | TWH | WH |
| | SEQ ID NO: | | | | | | | |
| | 4 | 13 | 14 | 12 | 35 | 36 | 37 | 38 |
| 120 min | UK | UK | UK | UK | UK | UK | UK | UK |
| 60 min | — | 16.9% | — | 23.2% | 13.9% | 25.8% | 13.9% | 2.1% |
| 30 min | — | 41.0% | — | 20.4% | 22.8% | 14.1% | 1.8% | — |
| 20 min | — | 52.2% | — | 15.9% | 23.3% | 7.6% | — | — |
| 10 min | 67.2% | — | — | 13.3% | 18.1% | 1.4% | — | — |
| 5 min | 92.9% | — | — | 7.1% | — | — | — | — |
| Start | 100% | — | — | — | — | — | — | — |

TABLE 3

| No. | | Amino acid sequence | SEQ ID NO: |
|---|---|---|---|
| 9 | LL | RRPTTWHKP-G-RRPTTWHKP | 14 |
| 12 | LLL | RRPTTWHKP-G-RRPTTWHKP-G-RRPTTWHKP | 15 |
| 13 | FAM-L | [FAM]-RRPTTWHKP | 4 |
| 15 | Ld | RRPTTWHKP-G-pkhwttprr | 16 |
| 18 | NmLL | R-mR-PTTWHKP-G-RRPTTWHKP | 18 |
| 19 | NmLd | R-mR-PTTWHKP-G-pkhwttprr | 19 |

Each of the peptides described above was added to human blood plasma having a concentration of 50% by mass, the resulting mixture was sampled immediately after starting the degradation test (after 0 minutes), and then after 5 minutes, after 10 minutes, after 20 minutes, after 30 minutes, after 60 minutes and after 120 minutes, and the samples were analyzed by MALDI-TOFMS. The results are shown in FIGS. 2 to 6 and Tables 4 to 6 shown below. Furthermore, the data for the degradation test by human blood plasma using PCPP11 from Reference Example 1 and the degradation tests by human blood plasma using each of the above peptides are collated in FIG. 7 and Table 7. The SEQ ID NO listed for the FAM-labeled peptide represents the SEQ ID NO of the peptide portion. Further, the No. shown for each peptide in Tables 4 to 6 corresponds with the numerical value recorded on the peaks of the graphs shown in FIGS. 2 to 6. In each table, in those cases where the numerical values are shown separated into an upper row and a lower row, the upper row value indicates the proportion (%) of peak area for two or more peptides relative to the total peak area in the MALDI-TOFMS analysis. On the other hand, the lower row value indicates the proportion (%) of each peptide when the peak area for the two or more peptides is deemed to be 100%. Moreover, for example, for the peptide No. 9 shown in Table 4, the left-side "70.0%" indicates the proportion (%) of the peptide No. 9 when the total peak area for the peptides No. 9 to 11 is deemed to be 100%, whereas the right-side "65%" indicates the proportion (%) of the peptide No. 9 relative to the total peak area in the MALDI-TOFMS analysis. This system is also used in the following tables.

Furthermore, in Table 5, No. 13 and No. 13', and No. 14 and No. 14' represent peptides which although composed of the same amino acid sequence, were attributed to different peaks in the MALDI-TOFMS analysis.

TABLE 4

| Peptide | No. | 9 | 10 | 11 |
|---|---|---|---|---|
| | Amino acid sequence | RRPTTWHKP-G-RRPTTWHKP | RPTTWHKP-G-RRPTTWHKP | TTWHKP-G-RRPTTWHKP |
| | SEQ ID NO: | 15 | 21 | 39 |
| 120 min | | | 93.9% | |
| | | (70.0%, 65%) | (18.9%) | (11.1%) |
| 60 min | | | 95.9% | |
| | | (82.1%, 79%) | (10.0%) | (7.9%) |
| 30 min | | | 100% | — |
| | | (92.1%) | (8.8%) | |
| 20 min | | | 96.7% | — |
| | | (92.1%, 89%) | (7.9%) | |
| 10 min | | | 88.6% | — |
| 5 min | | | 100% | — |
| Start | | | 100% | — |

TABLE 5

| | Peptide No. | | | |
|---|---|---|---|---|
| | 13 | 13' | 14 | 14' |
| | Amino acid sequence | | | |
| | [FAM]-RRPTTWHKP | [FAM]-RRPTTWHKP | [FAM]-RRPTTWH | [FAM]-RRPTTWH |
| | SEQ ID NO: | | | |
| | 4 | 4 | 14 | 14 |
| 120 min | 13.5% | 54.6% | | 22.1% |
| | | (28.6%) | (71.4%) | |
| 60 min | 37.4% | 56.8% | | 8.5% |
| | | (61.9%) | (38.1%) | |
| 30 min | 43.6% | 54.0% | | 2.4% |
| | | (81.2%) | (18.8%) | |
| 20 min | 45.6% | 52.9% | | 1.4% |
| | | (88.5%) | (11.5%) | |
| 10 min | 43.2% | 50.2% | | — |
| | | (93.2%) | (6.8%) | |
| 5 min | 47.2% | — | | — |
| Start | 47.6% | — | | — |

TABLE 6

| | Peptide No. | | |
|---|---|---|---|
| | 15 | 16 | 17 |
| | Amino acid sequence | | |
| | RRPTTWHKP-G-pkhwttprr | RPTTWHKP-G-pkhwttprr | TTWHKP-G-pkhwttprr |
| | SEQ ID NO: | | |
| | 17 | 40 | 41 |
| 120 min | | 94.5% | |
| | (24.6%) | (21.6%) | (53.8%) |
| 60 min | | 97.7% | |
| | (43.0%) | (25.6%) | (31.4%) |
| 30 min | | 97.8% | |
| | (62.3%) | (22.7%) | (15.0%) |
| 20 min | | 94.9% | |
| | (71.9%) | (19.3%) | (8.8%) |
| 10 min | | 94.2% | |
| | (82.2%) | (13.9%) | (3.8%) |
| 5 min | | 93.2% | |
| | (89.0%) | (9.2%) | (1.8%) |
| Start | | 87.8% | |
| | (96.9%) | (2.8%) | (0.4%) |

TABLE 7

| | No. | | | | | | |
|---|---|---|---|---|---|---|---|
| | 1 | 13 | 9 | 15 | 18 | 19 | 12 |
| | Type | | | | | | |
| | single PCPP11 | FAM-PCPP11 | tandem PCPP11 [LL form] | tandem PCPP11 [Ld form] | tandem PCPP11 [N-methylArg-LL] | tandem PCPP11 [N-methylArg-Ld] | triplet PCPP11 [LLL form] |
| | SEQ ID NO: | | | | | | |
| Peptide | 4 | 4 | 15 | 17 | 18 | 19 | 16 |
| 120 min | — | 29% | 65% | 32% | 100% | 100% | 100% |
| 60 min | — | 73% | 79% | 58% | 100% | 100% | 100% |
| 30 min | — | 87% | 91% | 84% | 100% | 100% | 100% |
| 20 min | — | 92% | 89% | 94% | 100% | 100% | 100% |
| 10 min | 67% | 90% | 84% | 100% | 100% | 100% | 100% |
| 5 min | 93% | 100% | 100% | 100% | 100% | 100% | 100% |
| Start | 100% | 100% | 100% | 100% | 100% | 100% | 100% |

Figure 2:
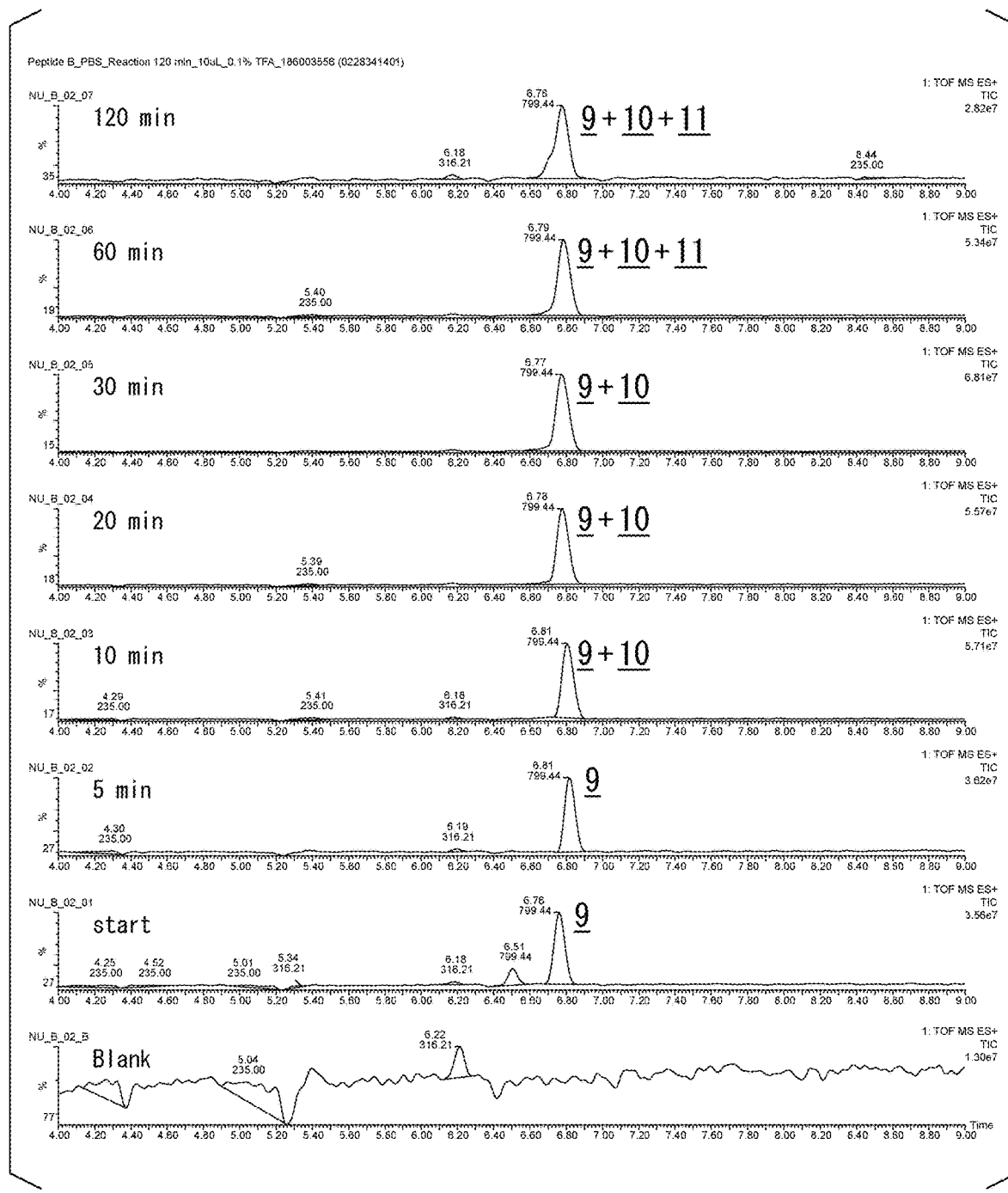
FIG. 2 is a graph illustrating the MALDI-TOFMS analysis results of degradation tests by human blood plasma using an LL peptide in Test Example 1.

Based on FIG. 2 and Table 4, it is evident that the degradation resistance of the LL peptide 120 minutes after starting the test was 65%. This "degradation resistance" represents the mass proportion of the peptide retained without degradation after 120 minutes from the start of the test relative to the mass (100%) of the peptide at the start of the test.

Figure 3:
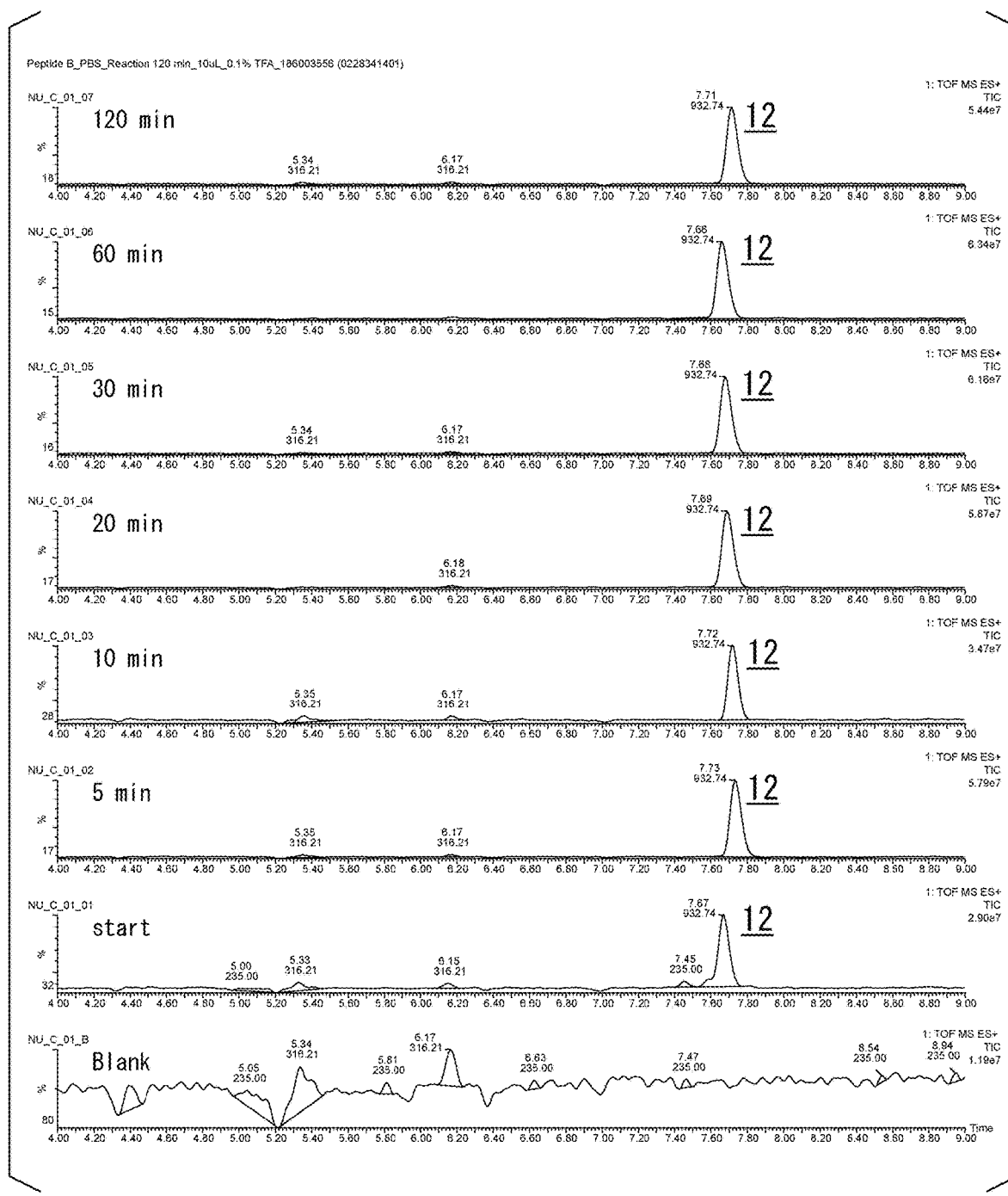
FIG. 3 is a graph illustrating the MALDI-TOFMS analysis results of degradation tests by human blood plasma using an LLL peptide in Test Example 1.

Further, based on FIG. 3, it is clear that with the peptide LLL, no degradation products were observed within 120 minutes of starting the test.

Figure 4:
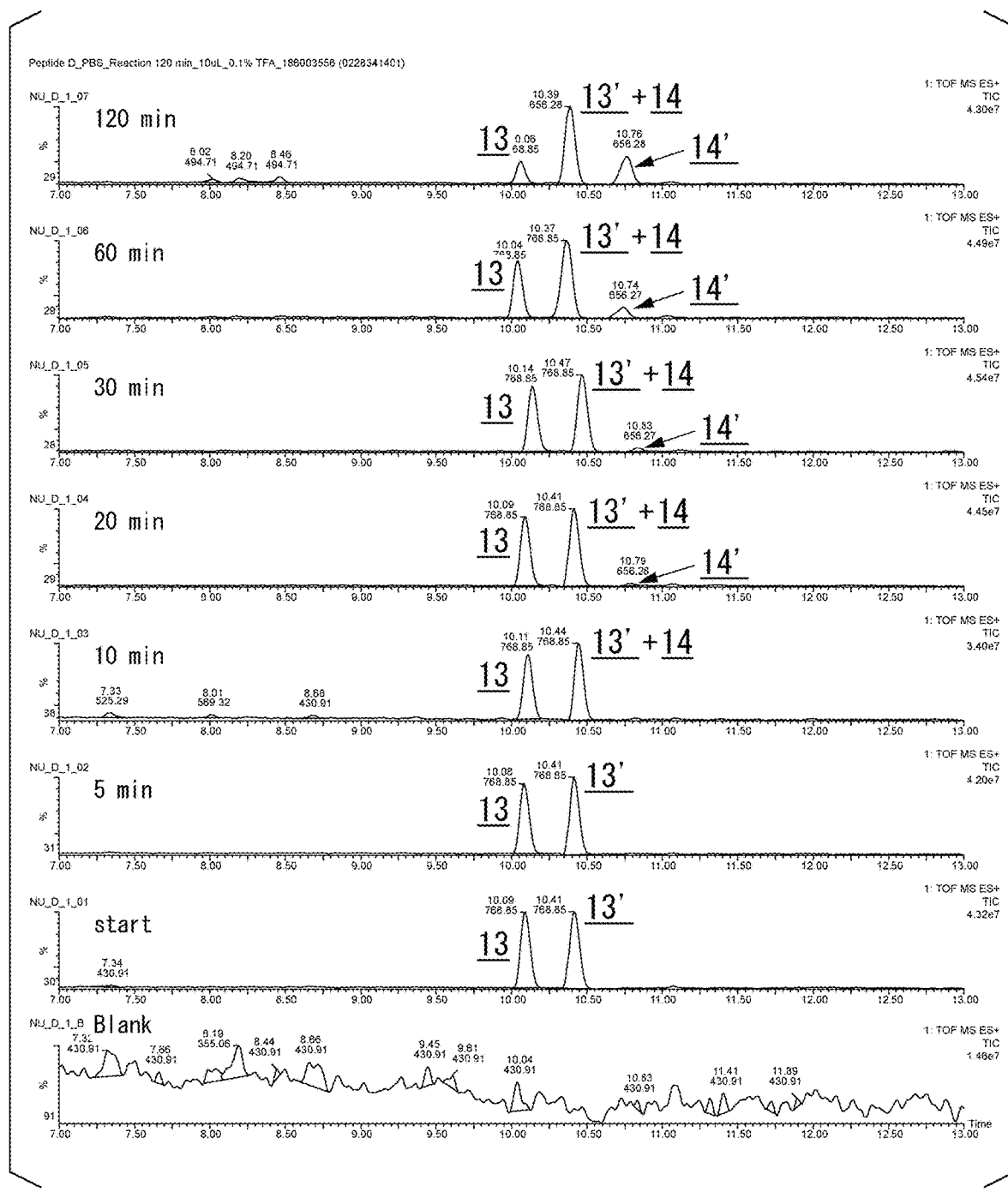
FIG. 4 is a graph illustrating the MALDI-TOFMS analysis results of degradation tests by human blood plasma using an FAM-L peptide in Test Example 1.

Further, FIG. 4 and Table 5 reveal that the degradation resistance of the PCPP11 that was FAM-labeled at the N-terminus 120 minutes after starting the test was 29%.

Figure 5:
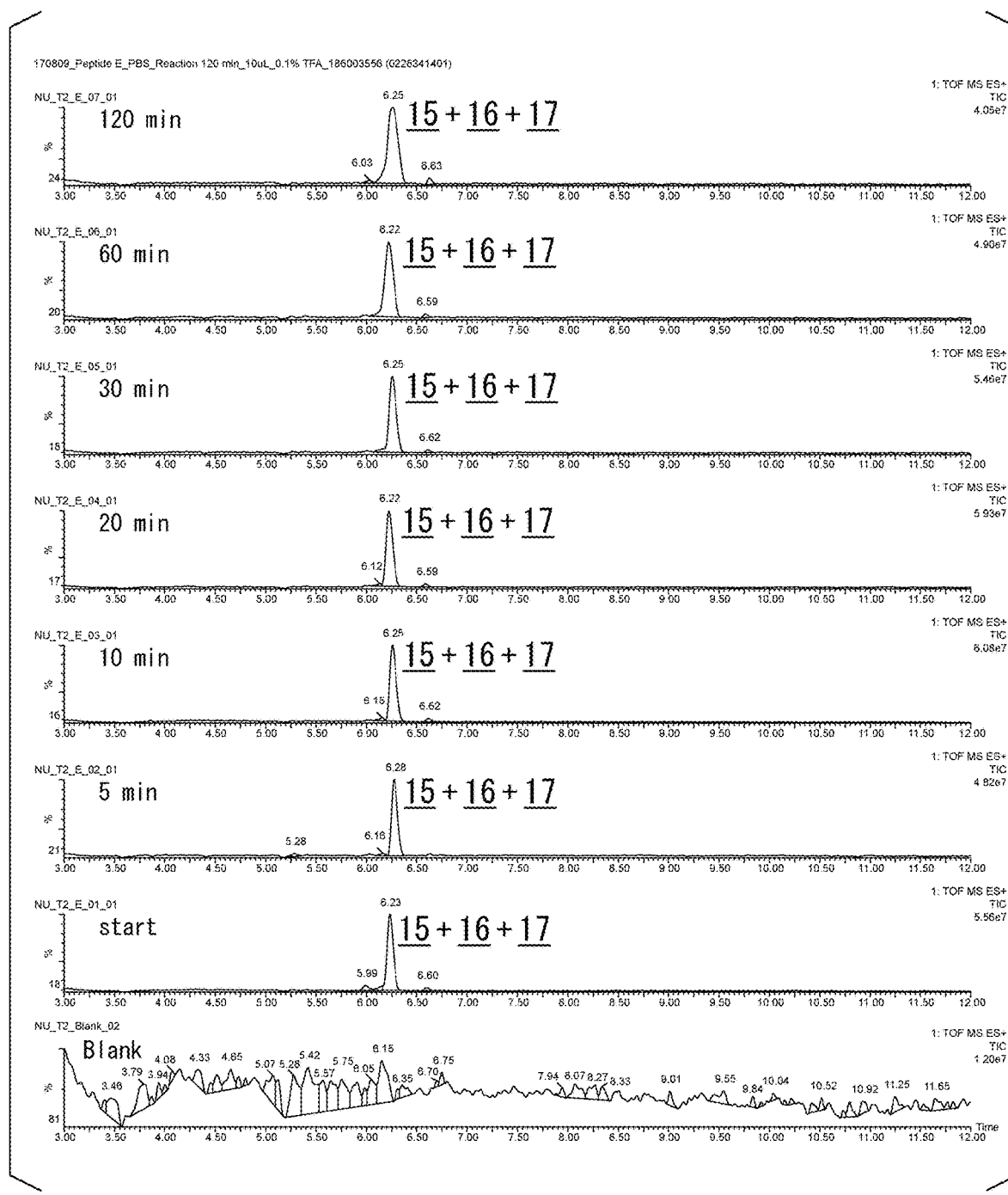
FIG. 5 is a graph illustrating the MALDI-TOFMS analysis results of degradation tests by human blood plasma using an Ld peptide in Test Example 1.

Furthermore, FIG. 5 and Table 6 reveal that the degradation resistance of the Ld peptide 120 minutes after starting the test was 32%.

Figure 6:
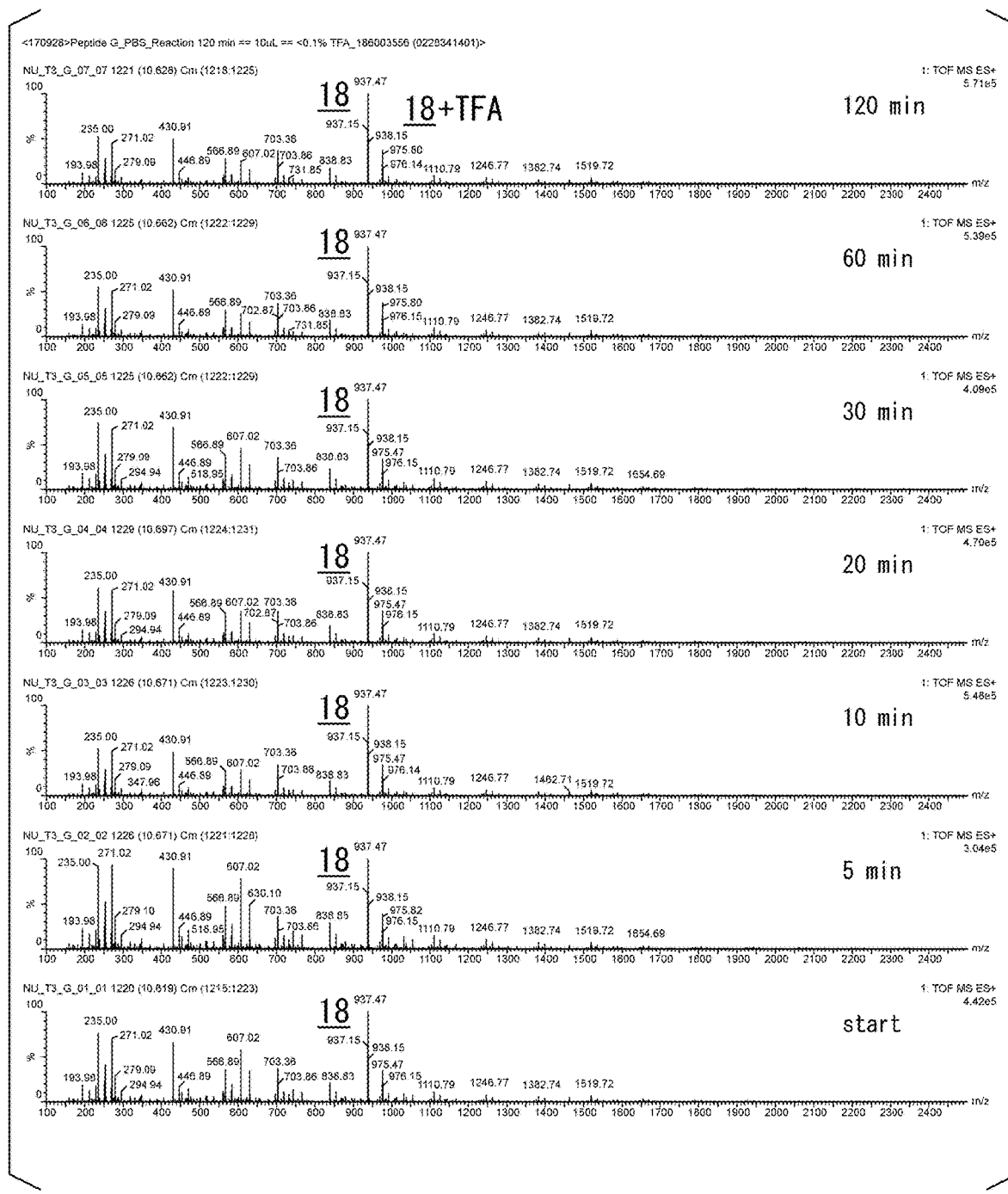
FIG. 6 is a graph illustrating the MALDI-TOFMS analysis results of degradation tests by human blood plasma using an NmLd peptide in Test Example 1.

Further, based on FIG. 6, it is clear that with the peptide NmLd, no degradation products were observed within 120 minutes of starting the test.

Figure 7:
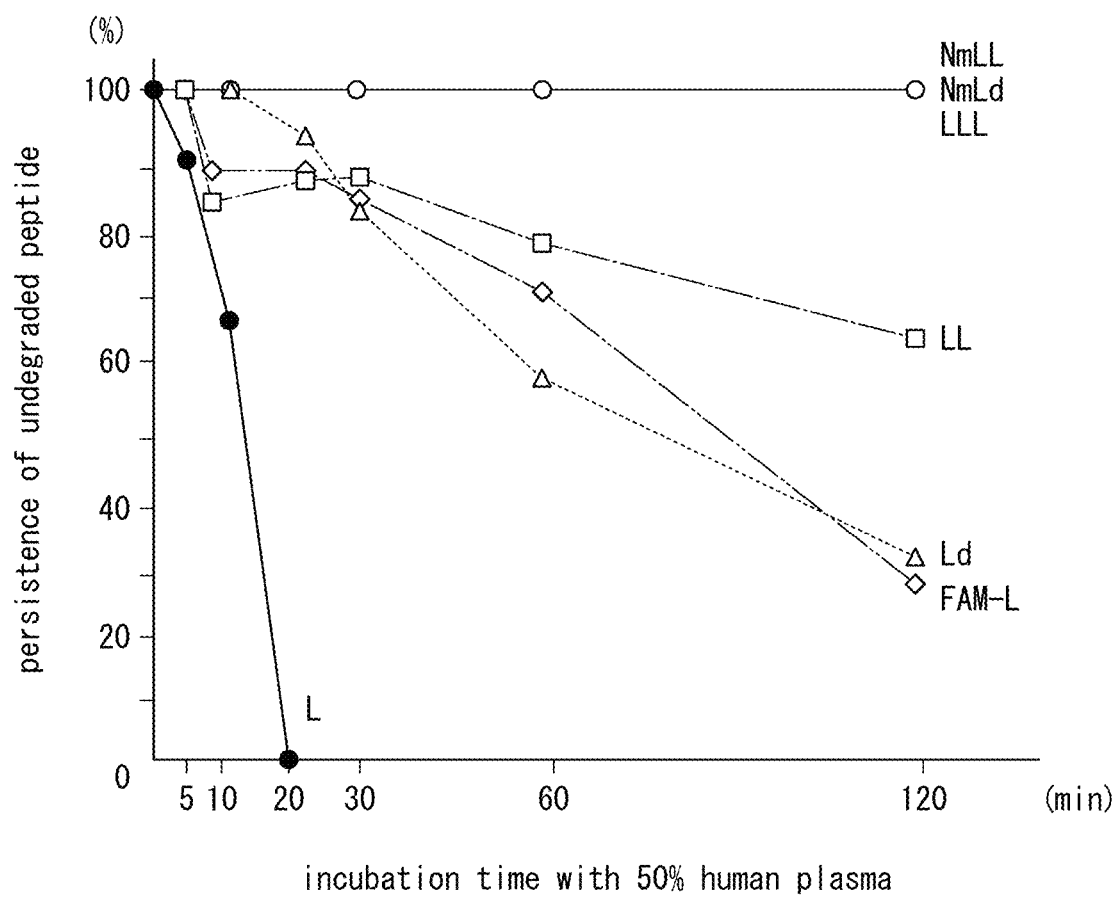
FIG. 7 is a graph comparing the degradation resistance of each of the peptides in Test Example 1.

Moreover, FIG. 7 and Table 7 confirm that the LL peptide, the Ld peptide, the NmLL peptide, the NmLd peptide and the LLL peptide all have superior degradation resistance compared with the stand-alone PCPP11 and the FAM-PCPP11.

In particular, for the NmLL peptide, the NmLd peptide and the LLL peptide, a degradation resistance was maintained at 100% after 120 minutes of testing, clearly indicating particularly superior degradation resistance.

[Test Example 2] Confirmation Test of Accumulation of Each Peptide in Pancreatic Cancer Cells and Other Cancer Cells Tests were conducted to confirm the accumulation of each peptide in each of the cells shown below in Table 8. Further, among the peptides shown below in Table 9, the FAM-PCPP11 used in Test Example 1, the LL peptide in which the N-terminus had been FAM-labeled (FAM-LL), and the Ld peptide in which the N-terminus had been FAM-labeled (FAM-Ld) were used.

TABLE 8

| Cell type | Cell name | Derivation |
|---|---|---|
| Pancreatic cancer cells | BxPC3 | Cell line derived from human pancreatic ductal adenocarcinoma (PDAC) |
| | PK-8 | Cell line derived from human PDAC |
| | MIA-Paca2 | Cell line derived from human PDAC |
| Lung cancer cells | H2110 | Adenocarcinoma cell line from human non-small-cell lung cancer system |
| Stomach cancer cells | SCH | Human stomach cancer cell line |
| Ovarian cancer cells | OVCAR3 | Cell line derived from patients with progressive human ovarian adenocarcinoma |
| Endometrial cancer cells | HEC59 | Cell line derived from human endometrial carcinoma |

TABLE 9

| Type | Amino acid sequence | SEQ ID NO: |
|---|---|---|
| FAM-PCPP11 | [FAM]-RRPTTWHKP | 4 |
| FAM-LL | [FAM]-RRPTTWHKP-G-RRPTTWHKP | 15 |
| FAM-LLL | [FAM]-RRPTTWHKP-G-RRPTTWHKP-G-RRPTTWHKP | 16 |
| FAM-Ld | [FAM]-RRPTTWHKP-G-pkhwttprr | 17 |
| FAM-NmLL | [FAM]-R-mR-PTTWHKP-G-RRPTTWHKP | 18 |
| NmLd-FAM | R-mR-PTTWHKP-G-pkhwttprr-$(CH_2)_2$-[FAM] | 19 |
| FAM-NmLd | [FAM]-R-mR-PTTWHKP-G-pkhwttprr | 19 |

Figure 8A:
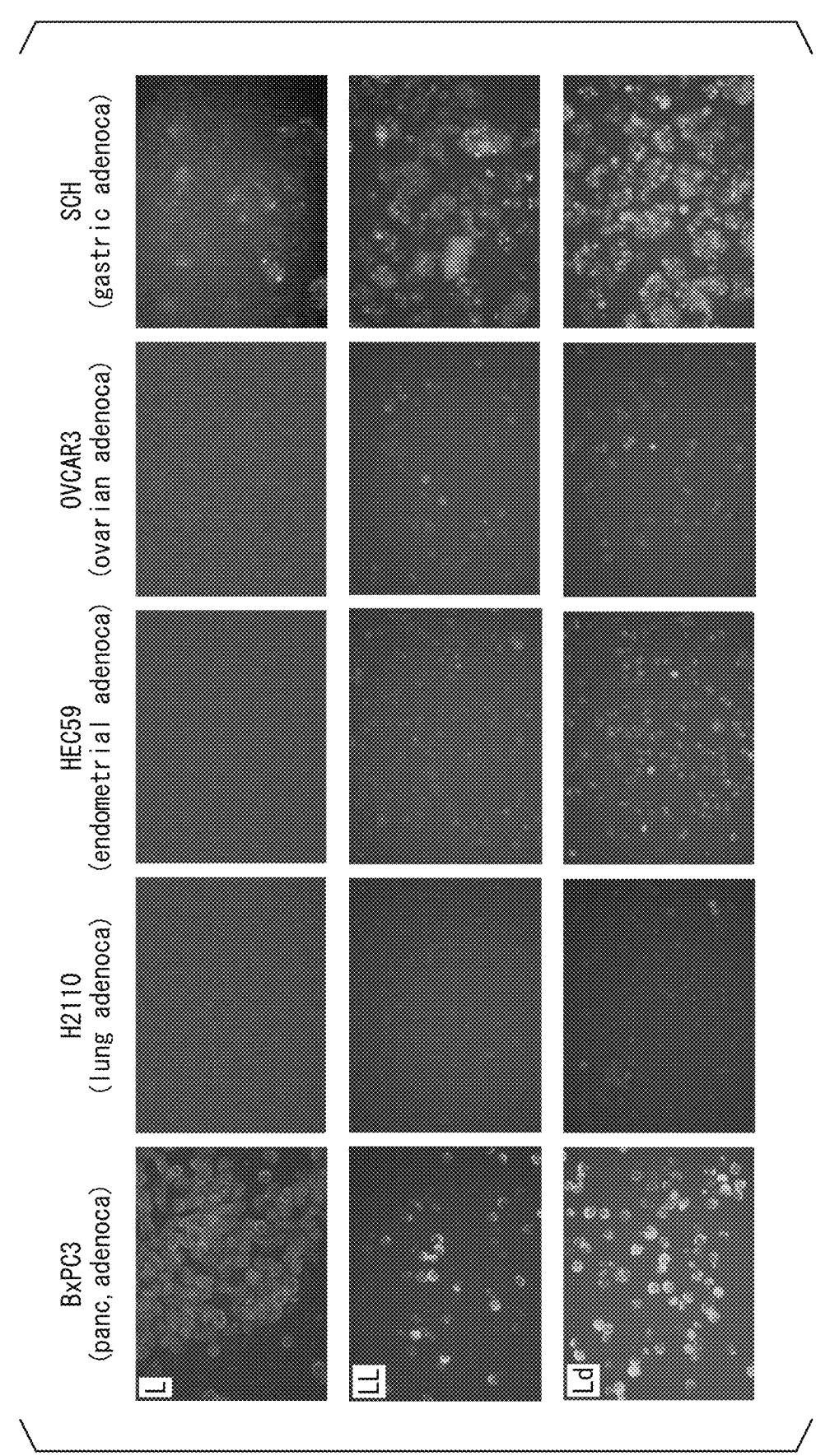
FIG. 8A is a series of fluorescence microscope images of various cells to which an FAM-PCPP11 (FAM-L peptide), an FAM-LL peptide and an FAM-Ld peptide have been added in Test Example 2.

Each of FAM-PCPP11, FAM-LL and FAM-Ld was added to each of the cells shown in Table 8 in an amount sufficient to achieve a final concentration in the medium of 2 μM, and following cultivation of the cells at 37° C. for 2 hours, the sample was washed 3 times with a medium containing no peptide to remove any peptide within the medium. Subsequently, the incorporation of each of the peptides into each of the cells was evaluated visually using an inverted fluorescence microscope. Prior to the microscopic examination, the culture supernatant to which the peptide had been added was removed, and following washing three times with 1×PBS (-), a trypsin treatment was conducted to remove the adherent cells, and the resultant was immediately transferred into a new 96-well plate and once again suspended in fresh culture solution before the microscopic examination was performed. The results are shown in FIG. 8A. In FIG. 8A, "L" indicates the cells to which FAM-PCPP11 was added, "LL" indicates the cells to which FAM-LL was added, and "Ld" indicates the cells to which FAM-Ld was added. Further, the fluorescent images in the BxPC3 cells indicate a representative example of pancreatic cancer cells.

Based on FIG. 8A, it is clear that for all of the peptides, strong fluorescence was detected in the pancreatic cancer cells and stomach cancer cells that represent cancer cells of the digestive system, whereas almost no fluorescence was detected in the other cancer cells. Among the other cancer cells, although the H2110 cells, which which are from an adenocarcinoma cell line from a human non-small-cell lung cancer system, are adenocarcinoma cells similar to those of the BxPC3 cells, the PK-8 cells and the MIA-Paca2 cells, they are lung primary cells rather than pancreatic primary cells, and are cells of an adenocarcinoma system having a different genesis. The observation that almost no fluorescence was detected in the H2110 cells, while strong fluorescence was detected in the BxPC3 cells, the PK-8 cells, the MIA-Paca2 cells and the SCH cells, confirmed that each of the peptides exhibited strong selective absorption into specific adenocarcinomas, namely cancer cells of the digestive system including pancreatic cancer cells and stomach cancer cells. Further, in the cancer cells of the digestive system including pancreatic cancer cells and stomach cancer cells, stronger fluorescence was detected in the samples containing the added FAM-LL and FAM-Ld than in the sample containing the added FAM-PCPP11.

Figure 8B:
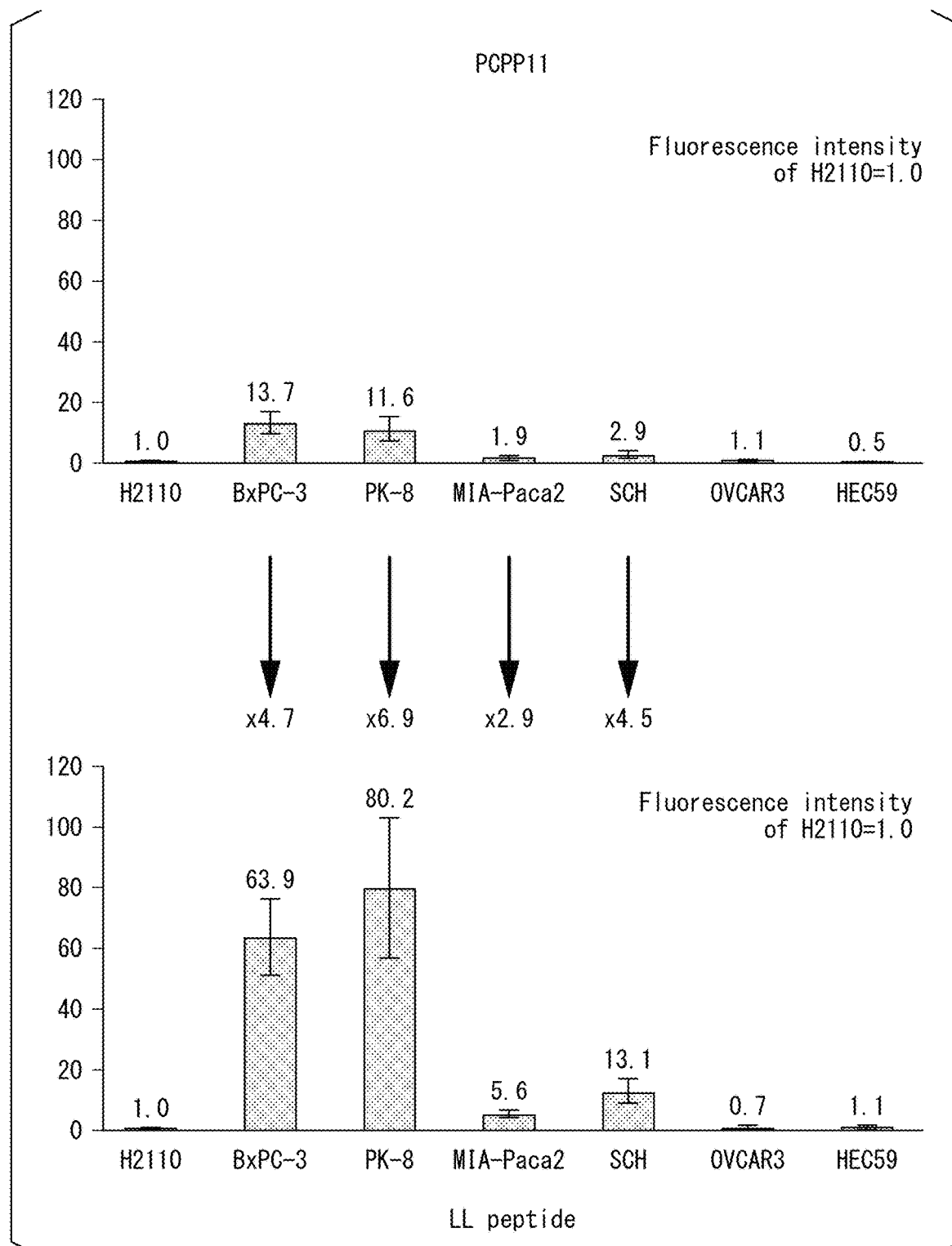
FIG. 8B is a graph quantifying the fluorescence detected in various pancreatic cancer cells and other cancer cells to which an FAM-PCPP11 (FAM-L peptide) and an FAM-LL peptide have been added in Test Example 2, with the fluorescence intensity detected in each cell shown relative to a value of 1.0 for the fluorescence detected in H2110 cells, which is a cell line derived from an adenocarcinoma in a human non-small-cell lung cancer system, to which each of the peptides has been added.

Furthermore, FIG. 8B is a graph quantifying the fluorescence detected in each of the above cells in FIG. 8A, with the fluorescence intensity detected in each cell shown relative to a value of 1.0 for the fluorescence detected in the H2110 cells, which is a cell line derived from an adenocarcinoma in a human non-small-cell lung cancer system, to which each of the FAM-PCPP11 and FAM-LL peptides had been added.

Based on FIG. 8B, it is evident that compared with the pancreatic cancer cells and stomach cancer cells to which the FAM-PCPP11 had been added, the quantitative value for the fluorescence in the pancreatic cancer cells and stomach cancer cells to which the FAM-LL had been added was markedly higher, with an increase of at least 2.9-fold.

Figure 8C:
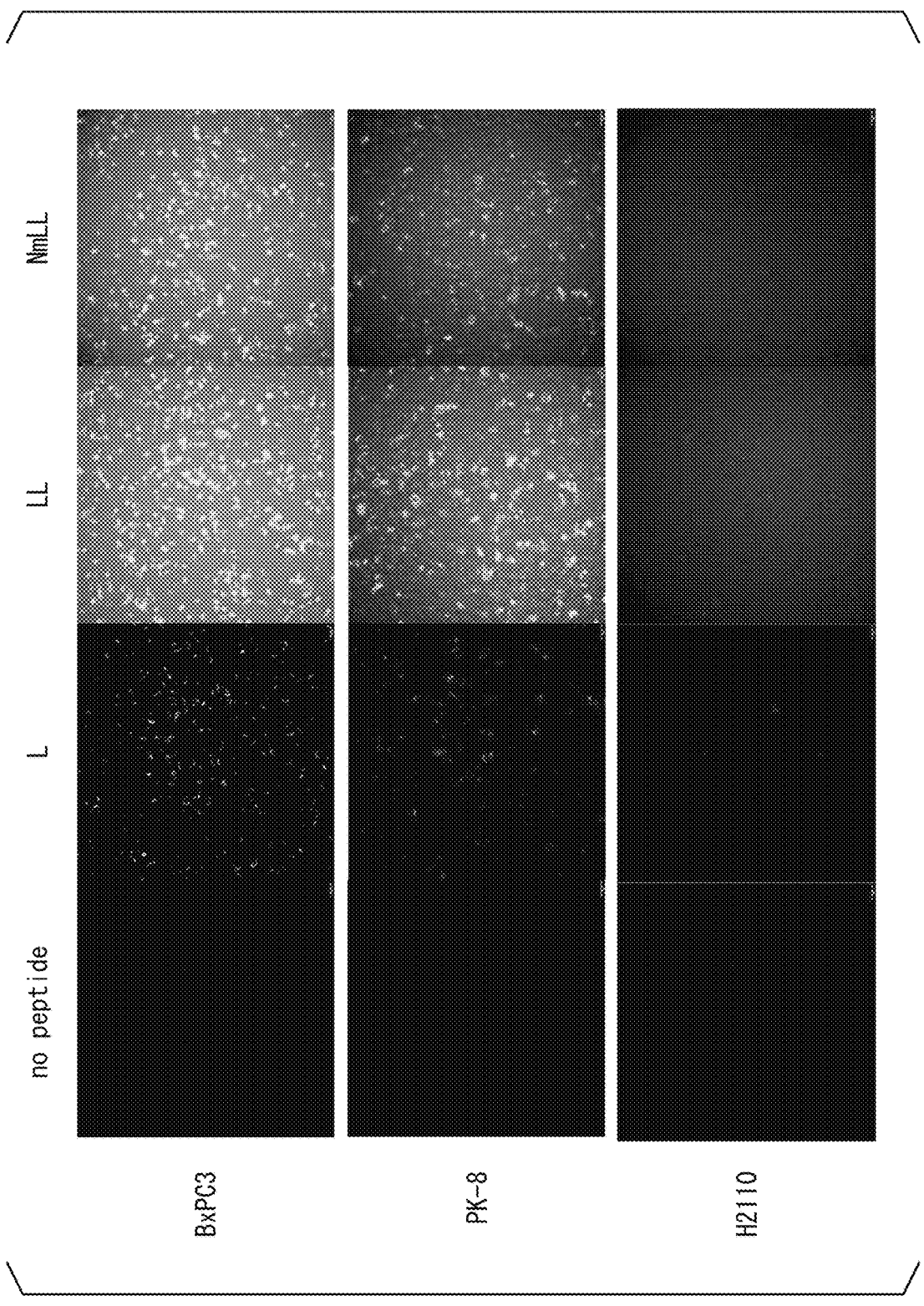
FIG. 8C is a series of fluorescence microscope images of various cells to which an FAM-PCPP11 (FAM-L peptide), an FAM-LL peptide and an FAM-NmLL peptide have been added in Test Example 2.

Further, each of FAM-PCPP11, FAM-LL and FAM-NmLL was added to each of the cells shown in Table 8 in an amount sufficient to achieve a final concentration in the medium of 2 μM, and following cultivation of the cells at 37° C. for 2 hours, the sample was washed 3 times with a medium containing no peptide to remove any peptide within the medium. Subsequently, the incorporation of each of the peptides into each of the cells was evaluated visually using an inverted fluorescence microscope. Prior to the microscopic examination, the culture supernatant to which the peptide had been added was removed, and following washing three times with 1×PBS (-), a trypsin treatment was conducted to remove the adherent cells, and the resultant was immediately transferred into a new 96-well plate and once again suspended in fresh culture solution before the microscopic examination was performed. The results are shown in FIG. 8C. In FIG. 8C, "L" indicates the cells to which FAM-PCPP11 was added, "LL" indicates the cells to which FAM-LL was added, and "NmLL" indicates the cells to which FAM-NmLL was added. Further, the fluorescent images in the BxPC3 cells and PK-8 cells indicate representative examples of pancreatic cancer cells.

Based on FIG. 8C, it is clear that for all of the peptides, strong fluorescence was detected in the pancreatic cancer cells, whereas almost no fluorescence was detected in the other cancer cells. Further, in the pancreatic cancer cells, stronger fluorescence was detected in the samples containing the added FAM-LL and FAM-NmLL than in the sample containing the added FAM-PCPP11.

Based on these results, it was clear that the peptides of embodiments of the present invention exhibited accumulation shifted to a high degree toward cancer cells of the digestive system including pancreatic cancer cells and stomach cancer cells compared with other cancer cells.

[Test Example 3] Evaluation Tests on Selective Absorption of Each Peptide into Various Tissues of Human Pancreatic Cancer Cell-Transplanted Mice 1. Preparation of Fluorescent Labeled Peptides As shown above in Table 9, the FAM-PCPP11 used in Test Example 1, the LL peptide, LLL peptide and Ld peptide that had been FAM-labeled at the N-terminus, and the NmLd peptide that had been FAM-labeled at the C-terminus with an ethylene group interposed therebetween were prepared. Further, in the following tests and figures, each of these FAM-labeled peptides may sometimes simply be referred to as "PCPP11", "LL", "LLL", "Ld" and "NmLd" respectively.

Figure 9A:
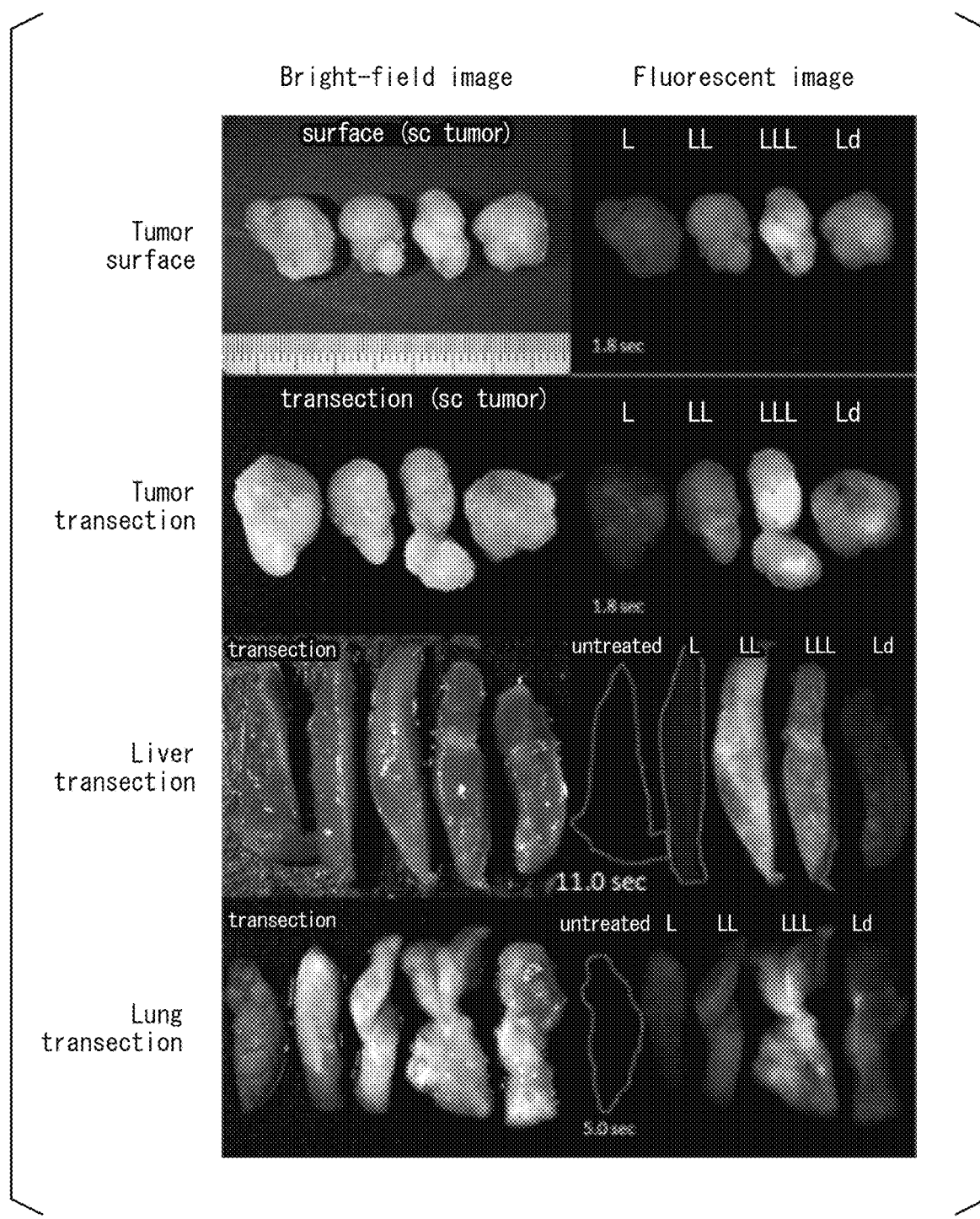
FIG. 9A is a series of bright-field images (left) and fluorescent images (right) of tumor surfaces, tumor transections, liver transections and lung transections of human pancreatic cancer growth and progression mouse models that have been administered with various fluorescent labeled peptides in Test Example 3.
Figure 9B:
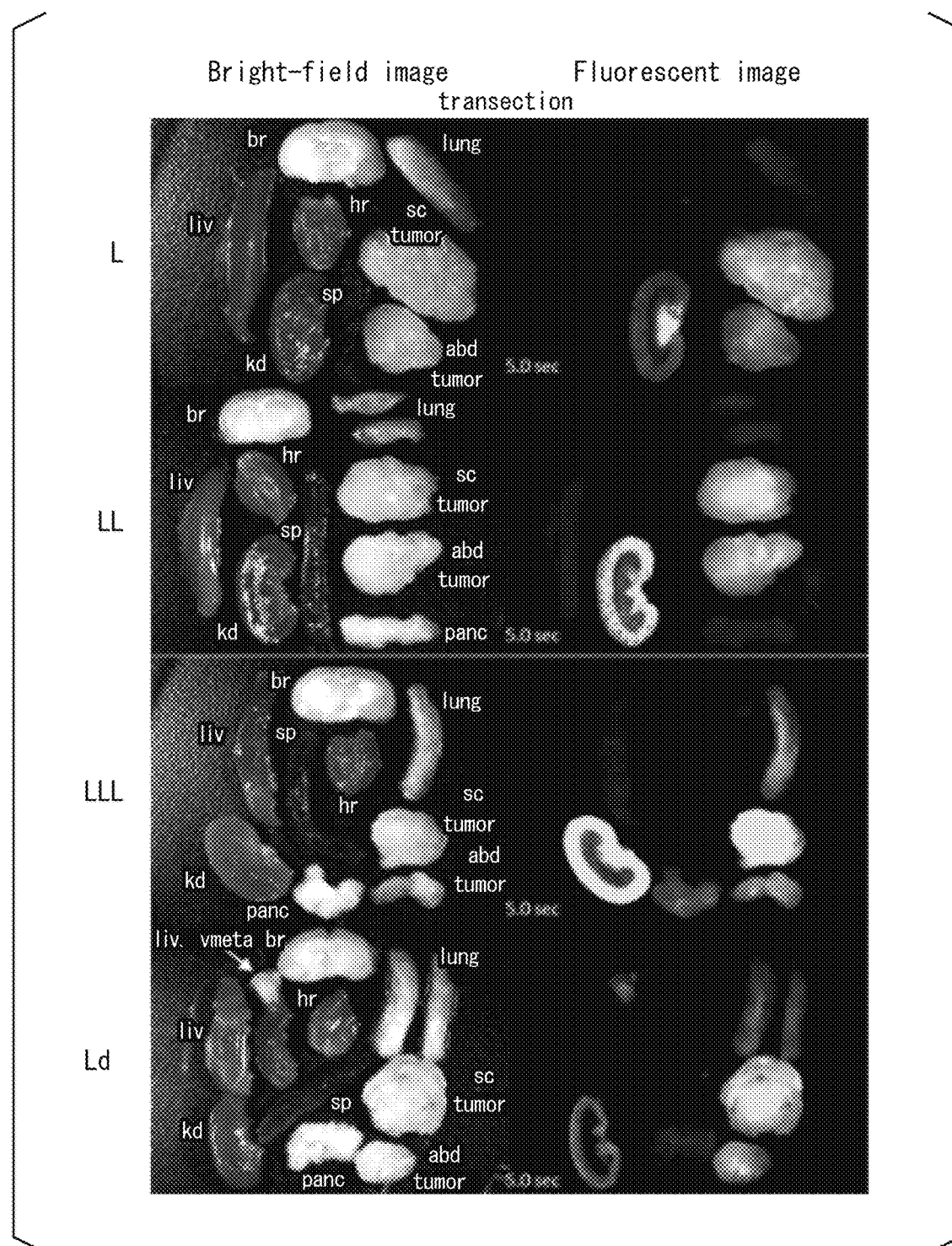
FIG. 9B is a series of bright-field images (left) and fluorescent images (right) of various tissue transections of human pancreatic cancer growth and progression mouse models that have been administered with various fluorescent labeled peptides in Test Example 3.
Figure 10A:
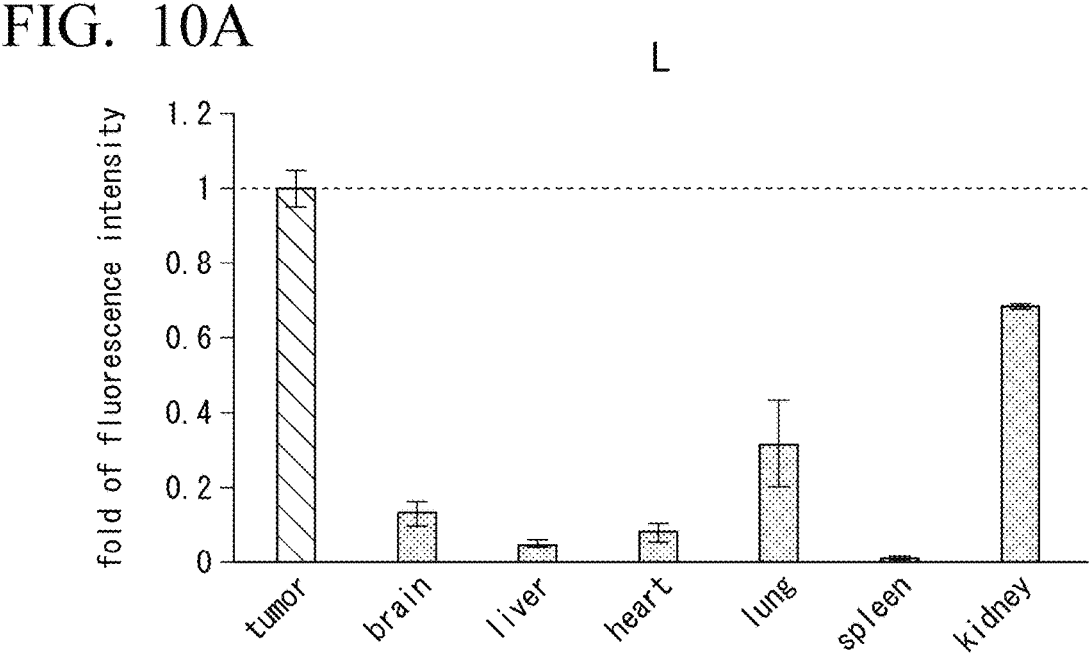
FIG. 10A is a graph comparing the fluorescence intensity in various tissues of human pancreatic cancer growth and progression mouse models that have been administered with an FAM-PCPP11 (FAM-L peptide) in Test Example 3.
Figure 10B:
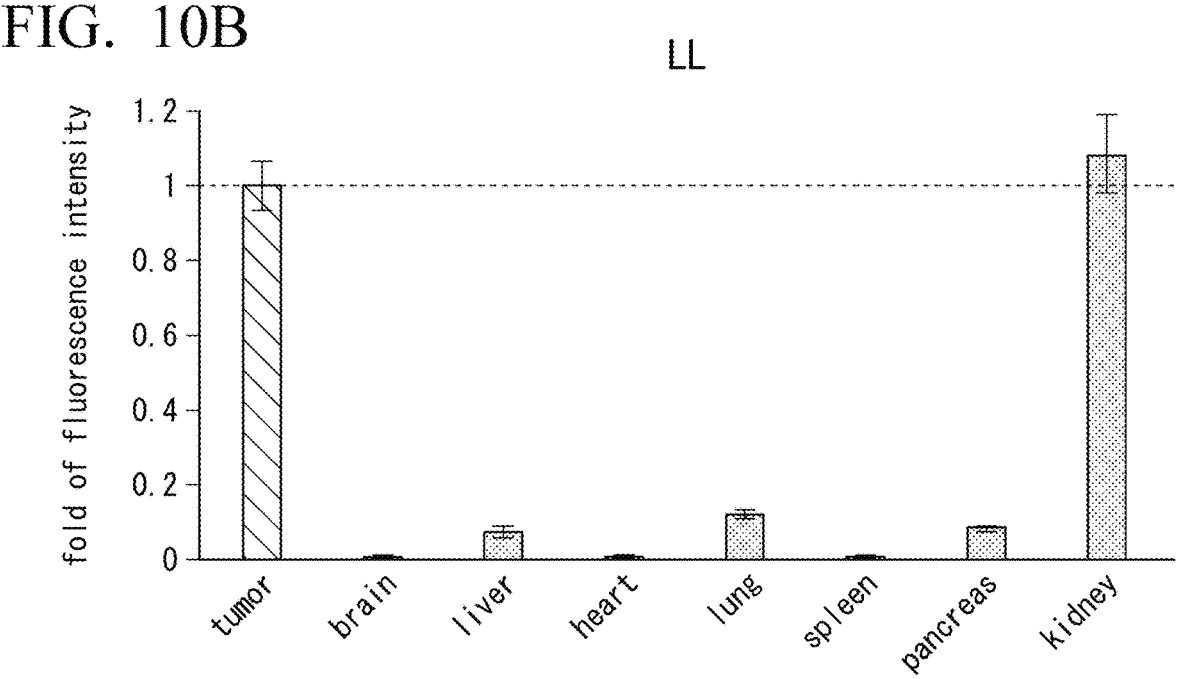
FIG. 10B is a graph comparing the fluorescence intensity in various tissues of human pancreatic cancer growth and progression mouse models that have been administered with an FAM-LL peptide in Test Example 3.
Figure 10C:
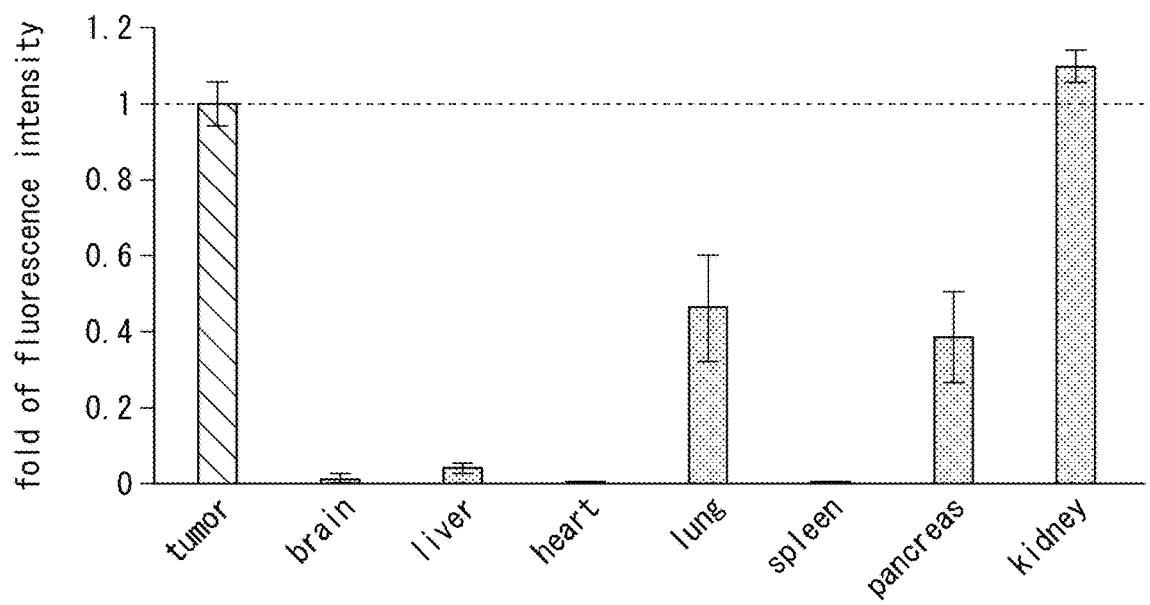
FIG. 10C is a graph comparing the fluorescence intensity in various tissues of human pancreatic cancer growth and progression mouse models that have been administered with an FAM-LLL peptide in Test Example 3.
Figure 10D:
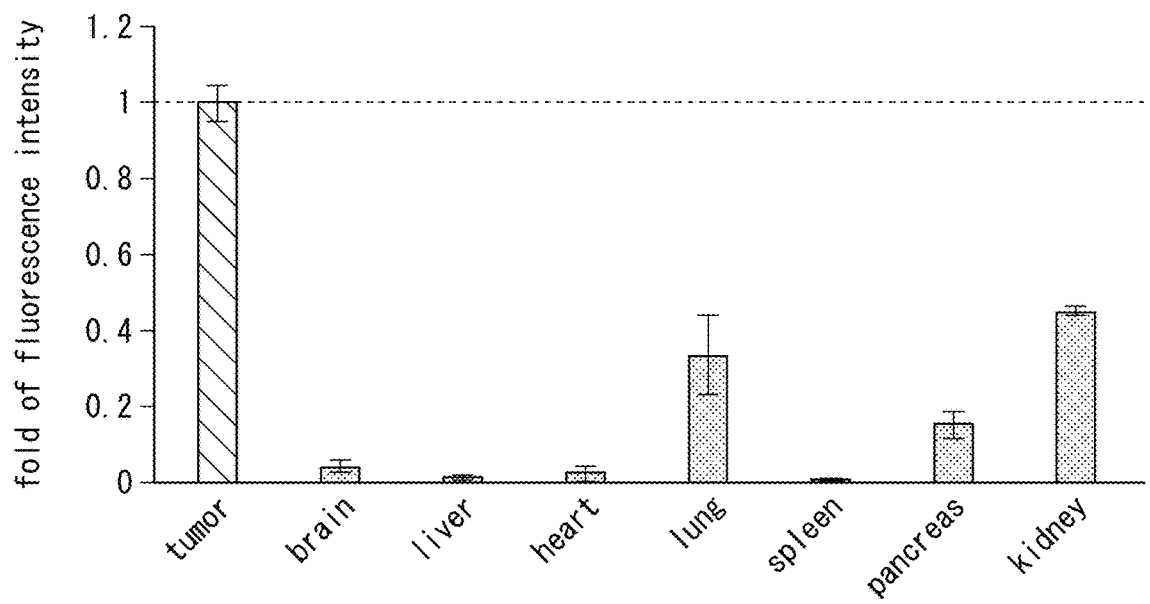
FIG. 10D is a graph comparing the fluorescence intensity in various tissues of human pancreatic cancer growth and progression mouse models that have been administered with an FAM-Ld peptide in Test Example 3.

2. Administration of Each Peptide to Human Pancreatic Cancer Growth and Progression Mouse Model Subsequently, 200 μg of each of the fluorescent labeled peptides prepared above in "1." was injected intravenously into a human pancreatic cancer growth and progression mouse model (Balb/c nu/nu mouse, subcutaneous and intraperitoneal human pancreatic cancer cell-transplanted model). The pharmacokinetics of the peptide 30 minutes after the intravenous injection were then analyzed by tissue analysis of the freshly dissected specimen of the administered mouse, with the absorption quantified by detection of the fluorescence signal. Bright-field images (left) and fluorescent images (right) of the surfaces and transections of various tissues of the human pancreatic cancer growth and progression mouse models that had been administered with each of the fluorescent labeled peptides are shown in FIG. 9A, and bright-field images (left) and fluorescent images (right) of various tissue transections for the fluorescent labeled peptides are shown in FIG. 9B. In FIG. 9A, "sc tumor" is an abbreviation for "subcutaneous tumor". In FIG. 9B, "abd tumor" is an abbreviation for "abdominal tumor", indicating a tumor formed intraperitoneally. Further, "br" indicates the brain, "hr" indicates the heart, "kd" indicates the kidney, and "liv" indicates the liver. Furthermore, "liv. meta" is an abbreviation for "liver metastatic tumor", and describes a tumor that has metastasized to the liver. Moreover, "panc" indicates the pancreas, and "sp" indicates the spleen. These same abbreviations are also used in subsequent figures. Furthermore, the term "untreated" in FIG. 9A indicates tissues resected from a mouse that was not administered with any fluorescent labeled peptide. Graphs quantifying the detection results for the fluorescent signal from each of the tissues are shown in FIG. 10A (FAM-PCPP11), FIG. 10B (FAM-LL peptide), FIG. 10C (FAM-LLL peptide) and FIG. 10D (FAM-Ld peptide). Further, a graph comparing the fluorescence intensity in the tumors of the human pancreatic cancer growth and progression mouse models that had been administered with the various fluorescent labeled peptides is shown in FIG. 11.

Figure 11:
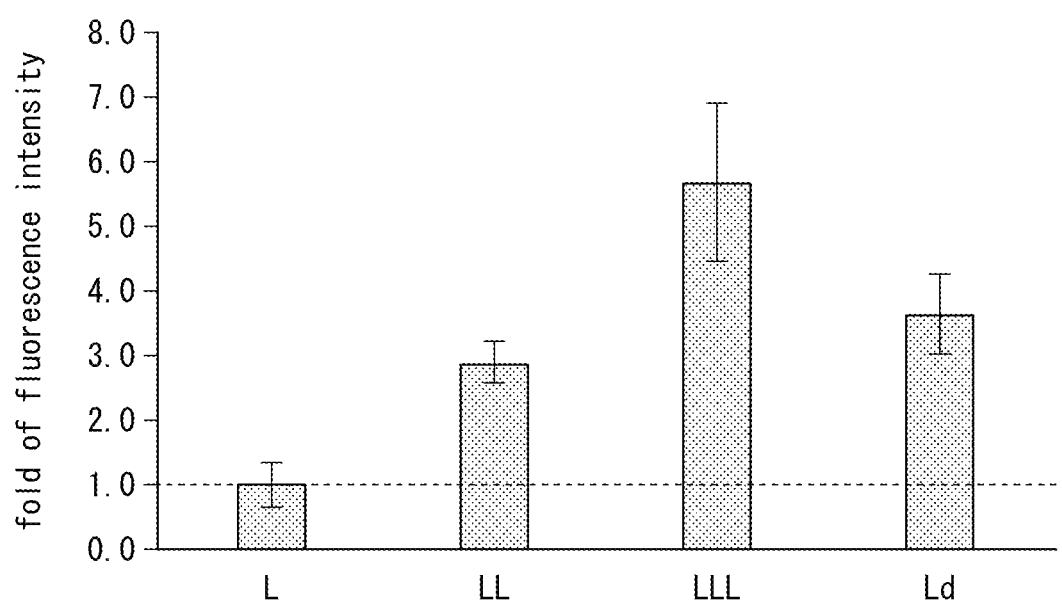
FIG. 11 is a graph comparing the fluorescence intensity in the tumors of human pancreatic cancer growth and progression mouse models that have been administered with various fluorescent labeled peptides in Test Example 3.

Based on FIG. 11, it is evident that the absorption into pancreatic malignant tumors, compared with the conventional PCPP11 composed of 9 amino acid residues, was 3-fold higher for the FAM-LL peptide, approximately 6-fold higher for the FAM-LLL peptide, and approximately 4-fold higher for the FAM-Ld peptide.

On the other hand, based on FIG. 10A to FIG. 10D, it was clear that the inhibitory performance on nonspecific absorption into untargeted normal organs which represents an advantage of the conventional PCPP11 was satisfactorily maintained in each of the FAM-LL peptide, the FAM-LLL peptide and the FAM-Ld peptide, and particularly in the case of the FAM-LL peptide and the FAM-Ld peptide, it was evident that nonspecific absorption was able to be inhibited even more effectively.

Figure 12A:
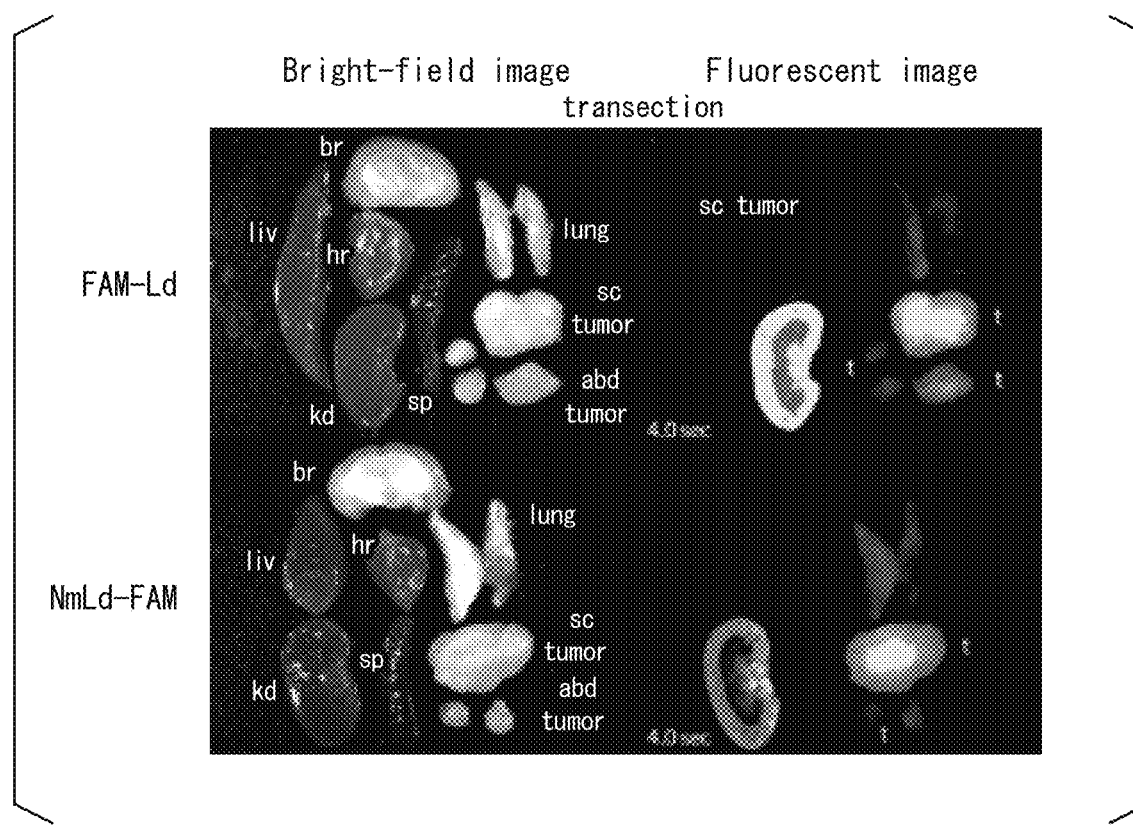
FIG. 12A is a series of bright-field images (left) and fluorescent images (right) of various tissue transections of human pancreatic cancer growth and progression mouse models that have been administered with an FAM-Ld peptide or an NmLd-FAM peptide in Test Example 3.

Further, bright-field images (left) and fluorescent images (right) of the transections of various tissues of the human pancreatic cancer growth and progression mouse models that had been administered with the NmLd peptide-FAM or the FAM-Ld peptide are shown in FIG. 12A. Furthermore, a graph comparing the fluorescence intensity in the tumors of human pancreatic cancer growth and progression mouse models that had been administered with the NmLd peptide-FAM or the FAM-Ld peptide is shown in FIG. 12B.

Figure 12B:
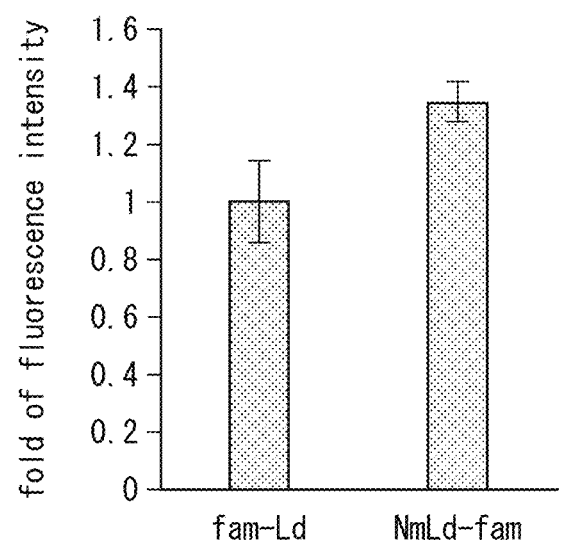
FIG. 12B is a graph comparing the fluorescence intensity in the tumors of human pancreatic cancer growth and progression mouse models that have been administered with an FAM-Ld peptide or an NmLd-FAM peptide in Test Example 3.

Based on FIG. 12B, it is evident that the absorption into pancreatic malignant tumors for the NmLd peptide was approximately 1.4-fold that of the Ld peptide. On the other hand, based on FIG. 12A, it was clear that the inhibitory performance on nonspecific absorption into untargeted normal organs was maintained satisfactorily for the NmLd peptide at a similar level to that observed for the Ld peptide.

Figure 13A:
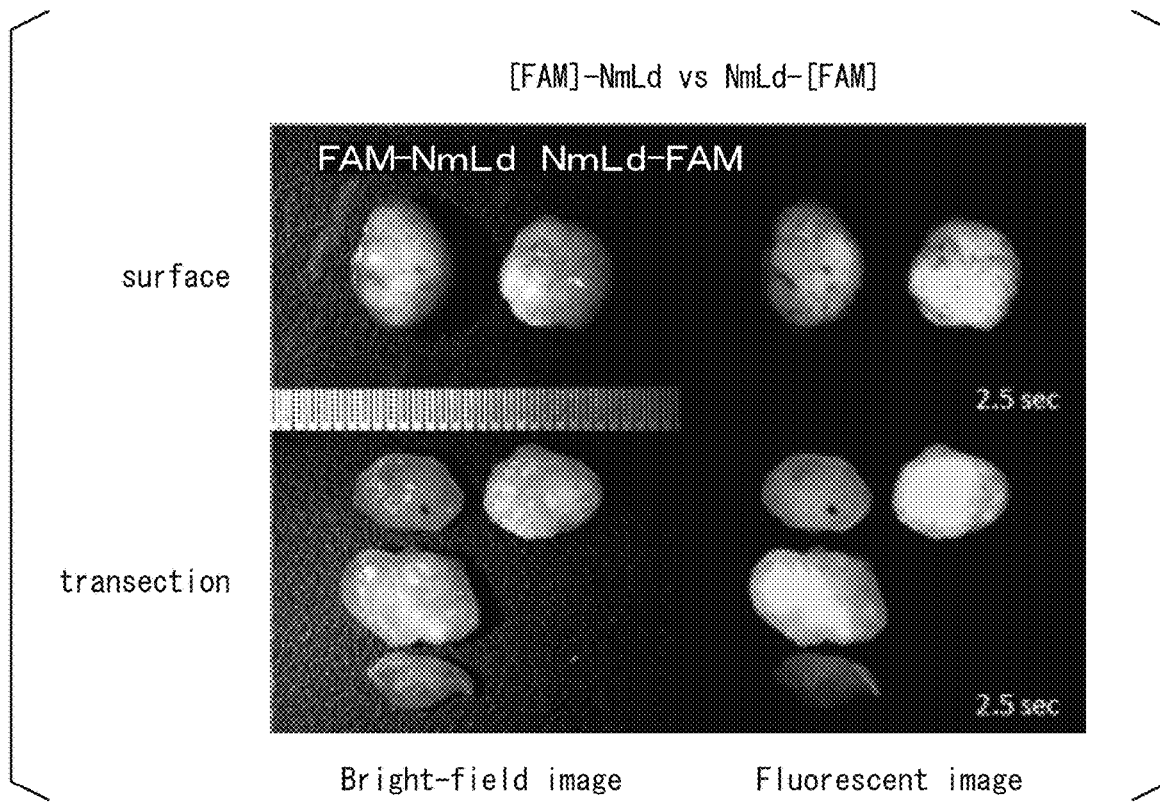
FIG. 13A is a series of bright-field images (left) and fluorescent images (right) of tumor surfaces and tumor transections of human pancreatic cancer growth and progression mouse models that have been administered with an FAM-NmLd peptide or an NmLd-FAM peptide in Test Example 3.

Further, because the labeling site for the fluorescent substance frequently affects the performance of the peptide, a comparative administration test was conducted for the NmLd peptide-FAM and the FAM-NmLd peptide. Bright-field images (left) and fluorescent images (right) of the surfaces and transections of various tissues of the human pancreatic cancer growth and progression mouse models that had been administered with the NmLd peptide-FAM or the FAM-NmLd peptide are shown in FIG. 13A. Further, a graph comparing the fluorescence intensity in the tumors of human pancreatic cancer growth and progression mouse models that had been administered with the NmLd peptide-FAM or the FAM-NmLd peptide is shown in FIG. 13B.

Figure 13B:
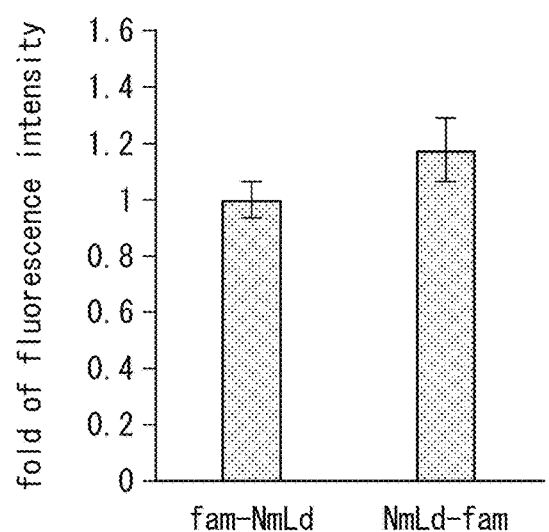
FIG. 13B is a graph comparing the fluorescence intensity in the tumors of human pancreatic cancer growth and progression mouse models that have been administered with an FAM-NmLd peptide or an NmLd-FAM peptide in Test Example 3.

FIG. 13A and FIG. 13B confirmed that the difference in the FAM labeling site had no significant impact on the performance of the peptide. These test results can act as important information when determining the bonding site for an anticancer drug on the peptide.

[Reference Example 2] Analysis Test of Biodistribution of Lone Fluorescent Substance The results in Test Example 2 are thought to demonstrate the action of the peptide itself in those cases where the peptide is bonded to the fluorescent substance (FAM). In order to confirm this hypothesis, analyses were conducted for cases where fluorescein (FLC) alone was administered to human pancreatic cancer growth and progression mouse models. FLC is a fluorescent substance accepted for human administration in medical treatment, and has substantially the same structure and characteristics as FAM.

Figure 14A:
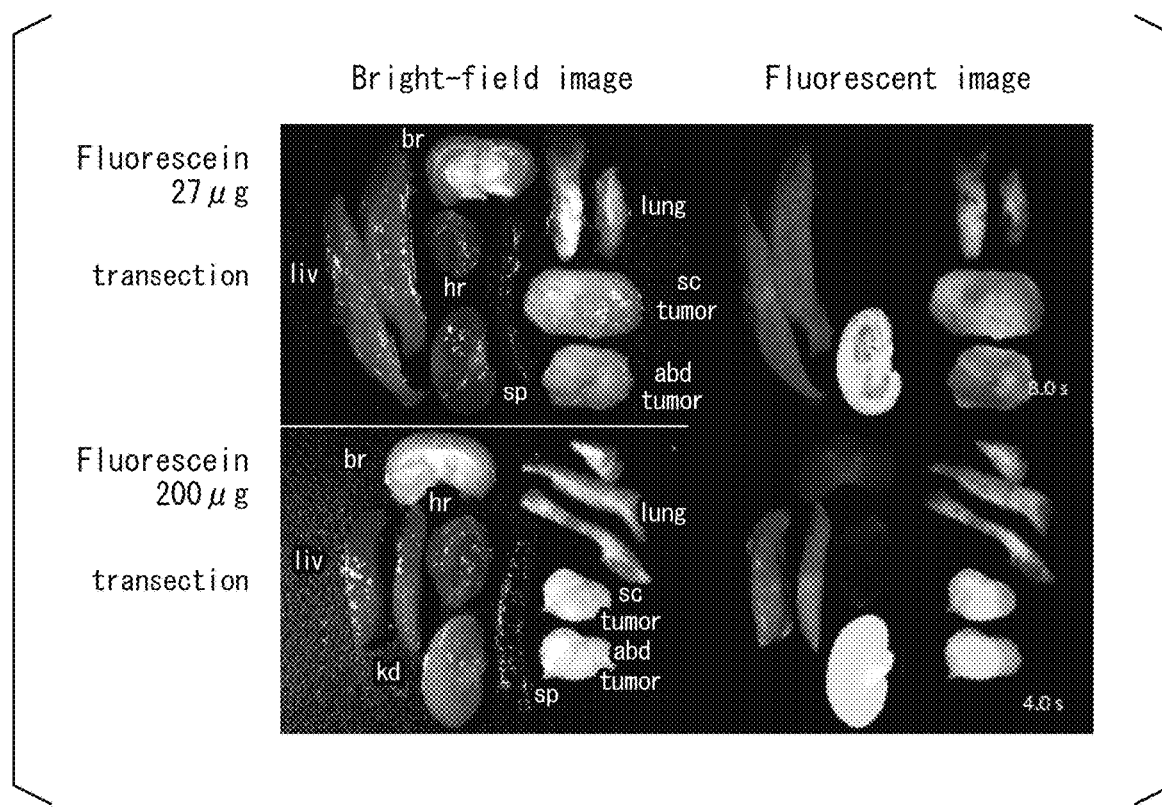
FIG. 14A is a series of bright-field images (left) and fluorescent images (right) of various tissue transections of human pancreatic cancer growth and progression mouse models that have been administered with 27 µg or 200 µg of fluorescein in Reference Example 2.

Specifically, first, either 27 μg or 200 μg of fluorescein was injected intravenously into a human pancreatic cancer growth and progression mouse model (Balb/c nu/nu mouse, subcutaneous and intraperitoneal human pancreatic cancer cell-transplanted model). The pharmacokinetics of the FLC 30 minutes after the intravenous injection were then analyzed by tissue analysis of the freshly dissected specimen of the administered mouse, with the absorption quantified by detection of the fluorescence signal. Bright-field images (left) and fluorescent images (right) of various tissue transections of the human pancreatic cancer growth and progression mouse models that had been administered with either 27 μg (top) or 200 μg (bottom) of fluorescein are shown in FIG. 14A. Furthermore, a graph quantifying the detection results for the fluorescence signal in various tissues of the human pancreatic cancer growth and progression mouse models that had been administered with either 27 μg (top) or 200 μg (bottom) of fluorescein is shown in FIG. 14B.

Figure 14B:
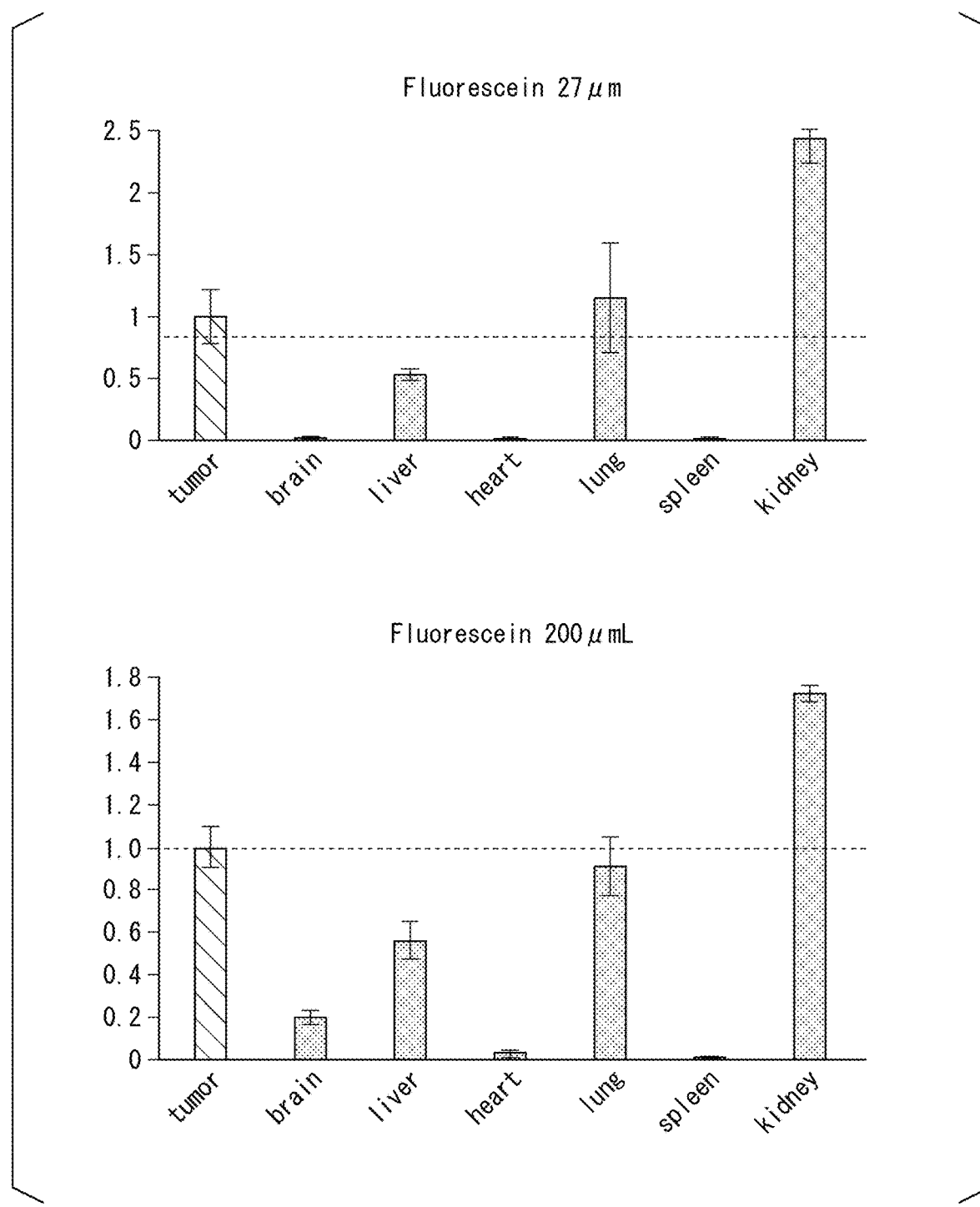
FIG. 14B is a graph comparing the fluorescence intensity in various tissues of human pancreatic cancer growth and progression mouse models that have been administered with 27 µg or 200 µg of fluorescein in Reference Example 2.

Based on FIG. 14A and FIG. 14B, it is evident that both in the case where administration is conducted at the same fluorescent molecule molar ratio as that used during the peptide administration in Test Example 2 (namely, 27 μg of fluorescein), and in the case where the FLC is administered in an amount that matches the total peptide mass (namely, 200 μg of fluorescein), a high degree of absorption was observed in the normal lungs, at a level substantially equal (90% to 120%) to the absorption into the targeted tumor tissue. In contrast, in the peptide administration of Test Example 2, the amount of absorption in the normal lungs was approximately 20% to 30% of the tumor absorption.

Further, in the case of the normal liver, the absorption was approximately 50% to 60% of the amount of absorption into the tumor. In contrast, in the peptide administration of Test Example 2, the amount of absorption in the normal liver was approximately 2% to 10% of the tumor absorption.

Furthermore, in the case of the normal kidneys, the absorption exceeded (180% to 250%) the amount of tumor absorption, indicating a high degree of nonspecific systemic absorption.

The above results demonstrated the specific tumor-selective absorption performance of each of the peptides including the LL peptide, the Ld peptide and the NmLd peptide.

[Test Example 4] Demonstration Test of Tumor Accumulation of LL Peptide as Anticancer Drug Delivery Composition Next, a peptide-drug-conjugate (PDC) was produced using the LL peptide, and an administration test was conducted in a human pancreatic cancer growth and progression mouse model.

Figure 15A:
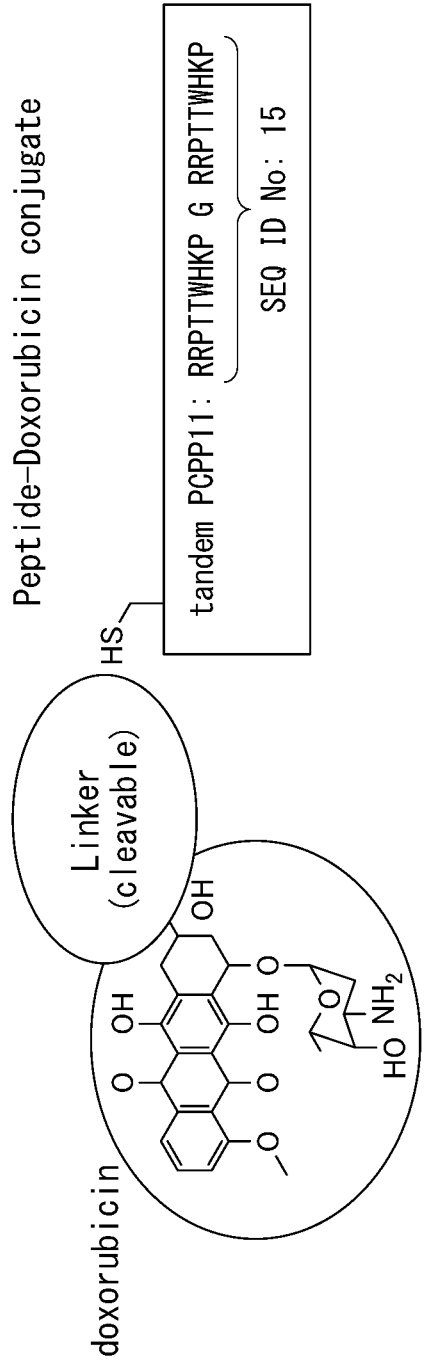
FIG. 15A is a schematic structural diagram illustrating the structure of a peptide (LL peptide)-drug (the antitumor agent doxorubicin)-conjugate (PDC) in Test Example 4.

FIG. 15A is a schematic structural diagram of the PDC used in Test Example 4. The LL peptide was bonded to the antitumor agent doxorubicin via a linker to form the PDC. A specific description of the method used for synthesizing the PDC is provided below.

First, in a 15 mL centrifuge tube, the LL peptide having a peptide linker composed of C-G-G-G (SEQ ID NO: 48) added to the N-terminus (compound B, 4 mg, 1.9 μmol, SEQ ID NO: 42) was added to a doxorubicin linker [Compound A] (2 mg, 2.8 μmol) and a dimethylsulfoxide solution (2 mL) of N,N-diisopropylethylamine (3 μL, 19 μmol), and the resulting mixture was shaken overnight at room temperature. The reaction mixture was then suspended in diethyl ether (10 mL), and following centrifugal separation, the supernatant was discarded. The sediment was dissolved in an aqueous solution of ammonium acetate (10 mM, pH 7, 1 mL), and then fractionated by size exclusion chromatography [Sephadex LH-20, ø1.5 cm×43 cm, eluent: aqueous solution of ammonium acetate (10 mM, pH 7)]. Each fraction was analyzed using a mass spectrometer (ESI-MS), and the fraction containing a compound C was collected and freeze dried. The thus obtained freeze dried powder was dissolved in deionized water and then freeze dried a second time to obtain the compound C (namely, the PDC) (2.3 mg).

Figure 15B:
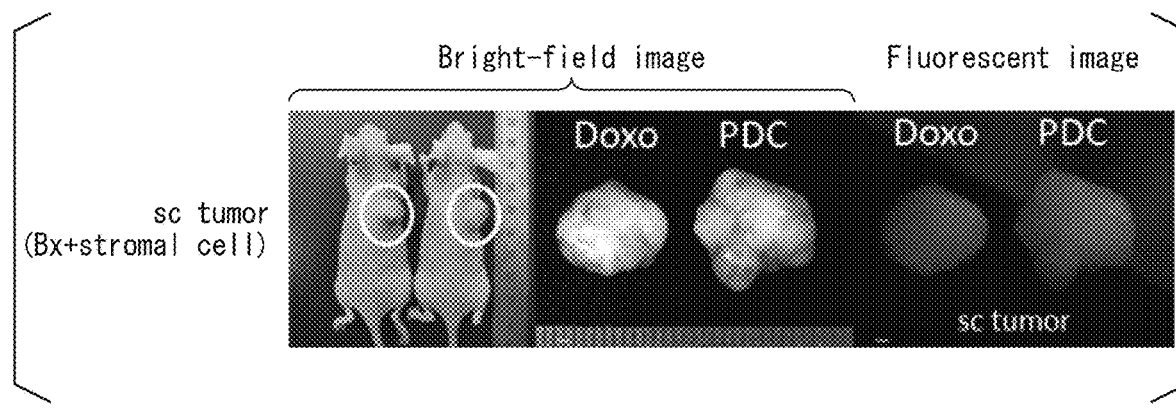
FIG. 15B shows full body images (left) of human pancreatic cancer growth and progression mouse models that have been administered with either doxorubicin alone or the PDC in Test Example 4, and bright-field images (center) and fluorescent images (right) of the tumor surfaces.
Figure 15C:
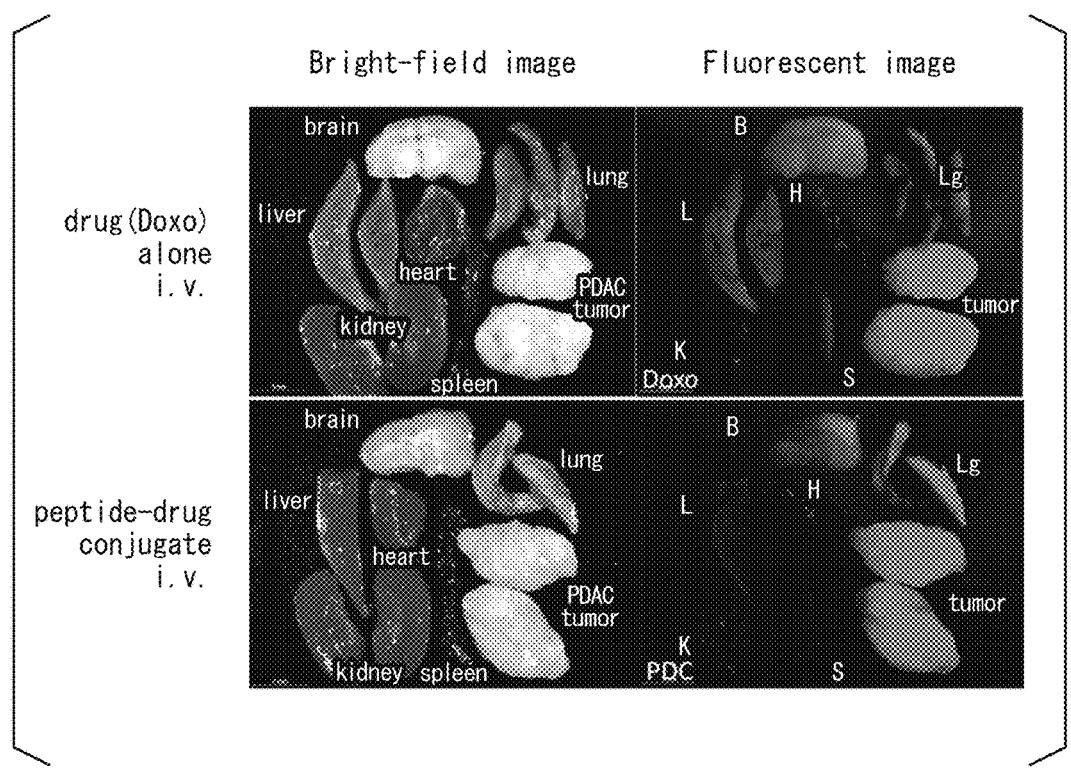
FIG. 15C is a series of bright-field images (left) and fluorescent images (right) of various tissue transections of human pancreatic cancer growth and progression mouse models that have been administered with either doxorubicin alone or the PDC in Test Example 4.

ESI-MS m/z $C_{151}H_{217}N_{47}O_{41}S$ [3378.69] calculated values: $[M+4H]^{4+}$ 845.7, $[M+5H]^{5+}$+676.8, observed values: 845.4, 676.5.

prepared as a control. In the doxorubicin alone administration, the dosage administered of the doxorubicin was matched with the molar amount of doxorubicin in the PDC. Full body images (left) of the human pancreatic cancer growth and progression mouse models that had been administered with either doxorubicin alone or the PDC, and bright-field images (center) and fluorescent images (right) of the tumor surfaces are shown in FIG. 15B. Further, bright-field images (left) and fluorescent images (right) of various tissue transections of the human pancreatic cancer growth and progression mouse models that had been administered with either doxorubicin alone or the PDC are shown in FIG. 15C.

Based on FIG. 15B, it is evident that in both the doxorubicin alone administration group (control group) and the PDC administration group, the absorption into the targeted

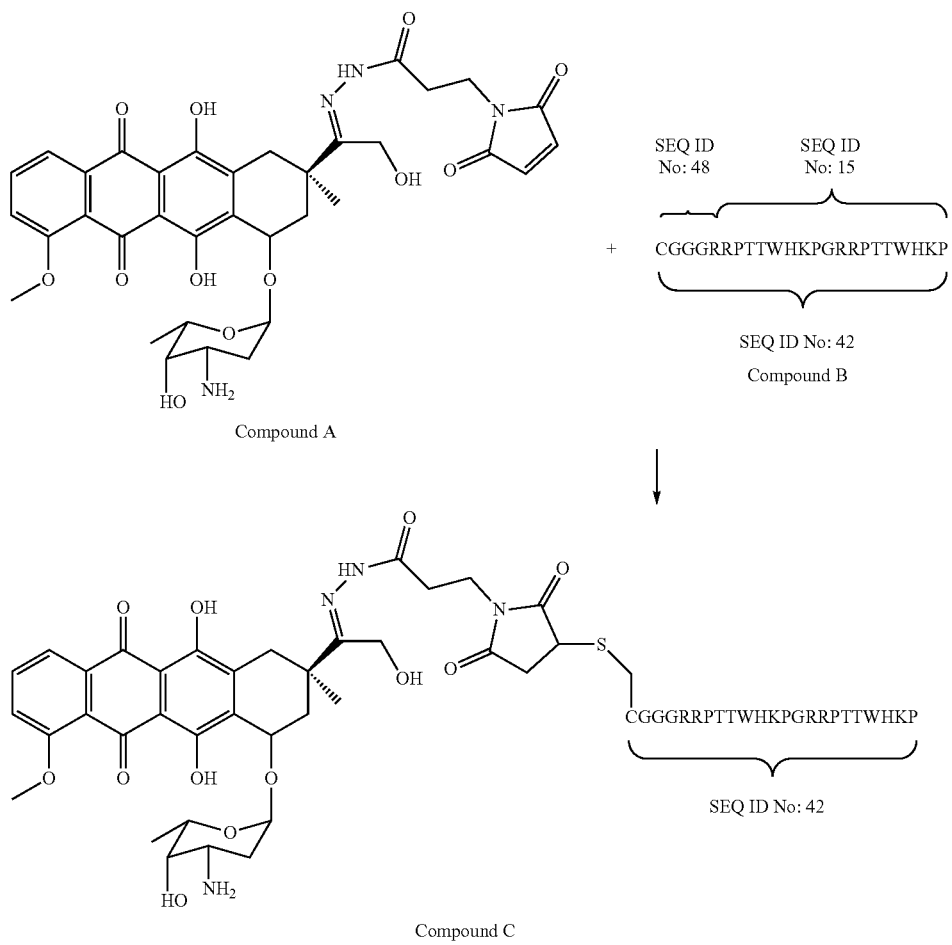

[Chemical Formula 1]

Subsequently, the PDC was injected intravenously into a human pancreatic cancer growth and progression mouse model (Balb/c nu/nu mouse, subcutaneous and intraperitoneal human pancreatic cancer cell-transplanted model) in an amount sufficient to provide a 200 μg dose of the peptide. The pharmacokinetics of the PDC 30 minutes after the intravenous injection were then analyzed by tissue analysis of the freshly dissected specimen of the administered mouse, with the absorption quantified by detection of the fluorescence signal. Further, a mouse that had been administered with doxorubicin alone, without peptide modification, was pancreatic cancer tumor tissue was substantially the same. On the other hand, based on FIG. 15C, it is clear that the nonspecific absorption into other normal organs was inhibited in the PDC administration group compared with the doxorubicin alone administration group (control group) for all of the liver, the brain, the heart, the lungs and the kidneys.

Quantitative analysis (not shown in the drawings) of the fluorescence intensity in specific other normal organs revealed that compared with the doxorubicin alone administration group (control group), the PDC administration group exhibited a 75% suppression of liver absorption, 32% suppression of brain absorption, 33% suppression of lung absorption, 94% suppression of heart absorption, and 60% suppression of kidney absorption.

The above results yielded a proof of concept (POC) of the usefulness of a PDC anticancer drug incorporating the peptide of an embodiment of the present invention as the delivery agent (namely, the generation of a drug having enhanced drug accumulation in tumors, and significantly reduced side-effects on the whole body).

[Reference Example 3] Confirmation Test of Accumulation of PCPP11 and Partially Deleted Peptides Thereof in Pancreatic Cancer Cells and Other Cancer Cells Test were conducted confirming the accumulation of PCPP11 and partially deleted peptides thereof in BxPC3 cells, PK-8 cells, AsPC1 cells and MIA-Paca2 cells (all cell lines derived from human invasive pancreatic ductal adenocarcinoma (PDAC)) and in H2110 cells (lung adenocarcinoma cells). The peptides shown below in Table 10 were used.

TABLE 10

| Type | Amino acid sequence | SEQ ID NO: |
|---|---|---|
| FAM-PCPP11 | [FAM]-RRPTTWHKP | 4 |
| FAM-trunc-ver1-PCPP11 | [FAM]-RPTTWHKP | 13 |
| FAM-trunc-ver2-PCPP11 | [FAM]-TTWHKP | 30 |
| FAM-trunc-ver3-PCPP11 | [FAM]-RRPTTWH | 14 |
| FAM-trunc-ver4-PCPP11 | [FAM]-RPTTW | 43 |
| FAM-trunc-ver5-PCPP11 | [FAM]-PTTWH | 44 |

Figure 16:
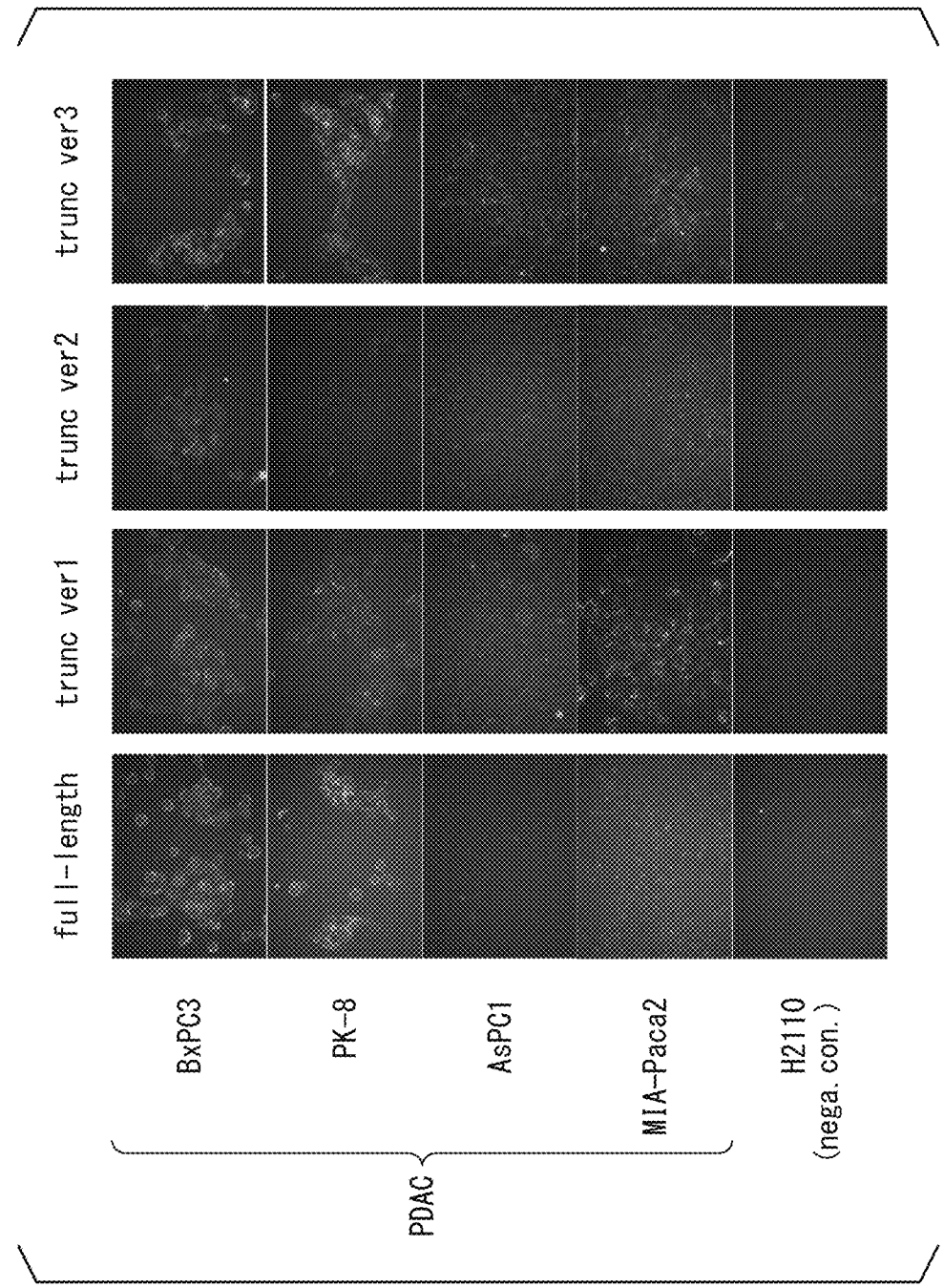
FIG. 16 is a series of fluorescence microscope images of various cells to which PCPP11 and partially truncated peptides thereof have been added in Reference Example 3.

Using the same method as Test Example 2, each peptide was added to each of the cells and then observed under a microscope. The results are shown in FIG. 16. In FIG. 16, "full length" indicates the cells to which FAM-PCPP11 was added, "trunc-ver1" indicates cells to which a trunc-ver1-PCPP11 was added, "trunc-ver2" indicates cells to which a trunc-ver2-PCPP11 was added, and "trunc-ver3" indicates cells to which a trunc-ver3-PCPP11 was added. A marked reduction in absorbed fluorescence was observed for FAM-trunc-ver2-PCPP11. Moreover, in the cells to which a FAM-trunc-ver4-PCPP11 and a FAM-trunc-ver5-PCPP11 had been added, almost no fluorescence was observed in the pancreatic cancer cells, and therefore the images were excluded.

Based on FIG. 16, it is evident that with each of the peptides, strong fluorescence was detected in the cell lines derived from PDAC. On the other hand, in the H2110 cells (lung adenocarcinoma cells), which although being a similar adenocarcinoma system to the cell lines derived from PDAC have a different genesis, almost no fluorescence was detected. Further, in the pancreatic cancer cells, the strength of fluorescence was detected in the order shown below.

full-length≥trunc-ver3>trunc-ver1>>trunc-ver2

Based on these results, it was clear that in the PCPP11 peptide which has accumulation shifted to a high degree toward pancreatic cancer cells, the amino acid residue composed of "R-P-T-T-W-H" (SEQ ID NO: 12) is essential, whereas the amino acid residue composed of "K-P" at the C-terminus is not necessarily essential.

[Test Example 5] Confirmation Tests of Accumulation of Various Peptides in Pancreatic Cancer Cells Test were conducted to confirm the accumulation of various peptides in each of the cells shown below in Table 11. Further, the peptides shown below in Table 12 were used.

TABLE 11

| Cell type | Cell name | Derivation |
|---|---|---|
| Pancreatic cancer cells | BxPC3 | Cell line derived from human PDAC |
| | PK-8 | Cell line derived from human PDAC |
| | MIA-Paca2 | Cell line derived from human PDAC |
| | AsPC1 | Cell line derived from human PDAC |
| | PL45 | Cell line derived from human PDAC |
| | Panc-1 | Cell line derived from human PDAC |

TABLE 12

| Type | Amino acid sequence | SEQ ID NO: |
|---|---|---|
| FAM-PCPP11 | [FAM]-RRPTTWHKP | 4 |
| FAM-d | [FAM]-pkhwttprr | 45 |
| FAM-LL | [FAM]-RRPTTWHKP-G-RRPTTWHKP | 15 |
| FAM-LL2 | [FAM]-RRPTTWHKP-GPG-RRPTTWHKP | 46 |
| FAM-dd | [FAM]-pkhwttprr-G-pkhwttprr | 47 |

Figure 17:
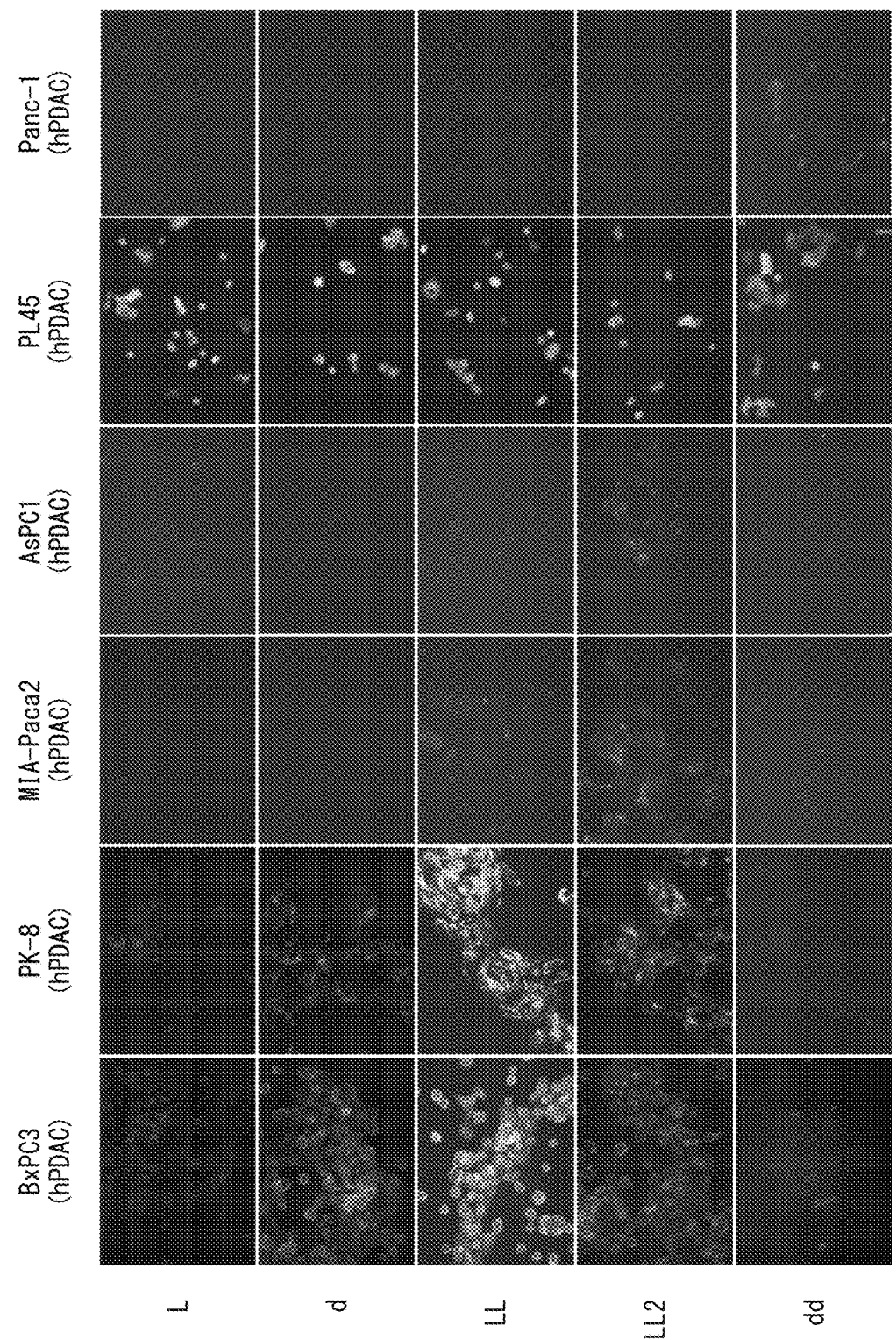
FIG. 17 is a series of fluorescence microscope images of various cells to which various peptides have been added in Test Example 5.

Each peptide was added to each of the cells shown in Table 11 in an amount sufficient to achieve a final concentration in the medium of 2 μM, and following cultivation of the cells at 37° C. for 2 hours, the sample was washed 3 times with a medium containing no peptide to remove any peptide within the medium. Subsequently, the incorporation of each of the peptides into each of the cells was evaluated visually using an inverted fluorescence microscope. Prior to the microscopic examination, the culture supernatant to which the peptide had been added was removed, and following washing three times with 1×PBS (−), a trypsin treatment was conducted to remove the adherent cells, and the resultant was immediately transferred into a new 96-well plate and once again suspended in fresh culture solution before the microscopic examination was performed. The results are shown in FIG. 17. In FIG. 17, "L" indicates the cells to which FAM-PCPP11 was added, "d" indicates the cells to which FAM-d was added, "LL" indicates the cells to which FAM-LL was added, "LL2" indicates the cells to which FAM-LL2 was added, and "dd" indicates the cells to which FAM-dd was added.

Based on FIG. 17, it is clear that with FAM-LL and FAM-LL2, stronger fluorescence was detected in each of the pancreatic cancer cells compared with the other peptides, and in the case of FAM-LL, particularly strong fluorescence was detected.

[Test Example 6] Evaluation Test of Selective Absorption of FAM-LL in Various Tissues of Scirrhous Pancreatic Cancer Model Mouse FAM-LL was administered to a pancreatic cancer model mouse having scirrhous carcinoma, and the selective absorption of the FAM-LL in various tissues of the mouse was confirmed. A scirrhous pancreatic cancer model mouse having scirrhous carcinoma that forms abundant tumor-stroma interactions was produced in accordance with the method disclosed in Reference Document 1 (Saito K et al., "Stromal mesenchymal stem cells facilitate pancreatic cancer progression by regulating specific secretory molecules through mutual cellular interaction.", Journal of Cancer, Vol. 9, No. 16, pp. 2916-2929, 2018.). Specifically, a 6-week old NOD/SCID mouse (CLEA Japan Inc., Japan) was raised under pathogen-free conditions. BxPC3 cells ($2 \times 10^5$ cells) and a cell mixture containing BxPC3 cells ($1 \times 10^5$ cells) and human mesenchymal stem cells (hMSC) ($1 \times 10^5$ cells) were each injected subcutaneously into the mouse. By raising the mouse for 6 weeks from the time of cell injection, a scirrhous pancreatic cancer model mouse was obtained that had a tumor formed from only human pancreatic cancer cells, and a tumor having abundantly developed tumor-stroma interactions that imitates the tissue in a human pancreatic cancer patient.

Figure 18A:
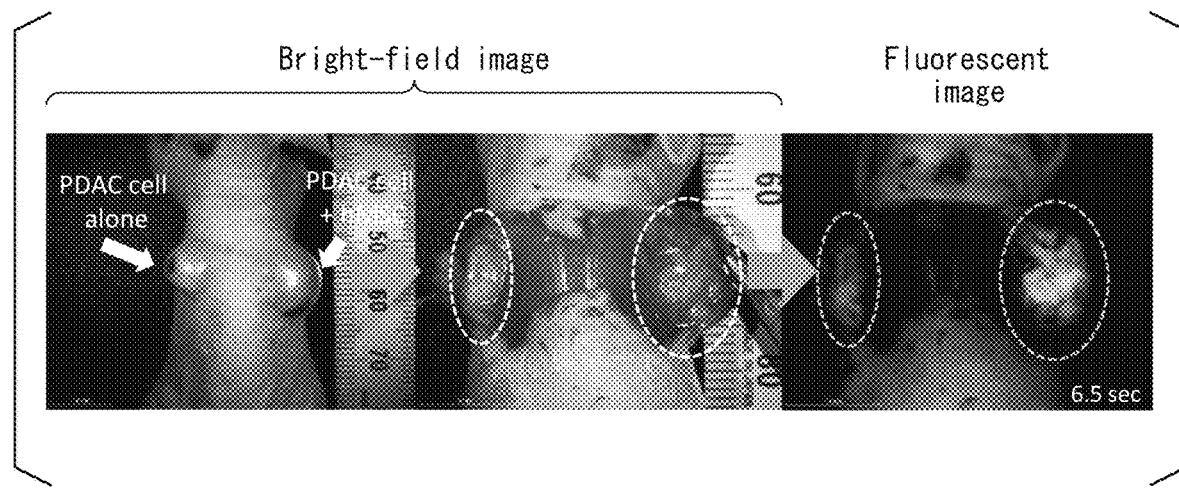
FIG. 18A is a series of bright-field images (left and center) and a fluorescent image (right) of tumors in a scirrhous pancreatic cancer model mouse that has been administered with an FAM-LL peptide in Test Example 6.
Figure 18B:
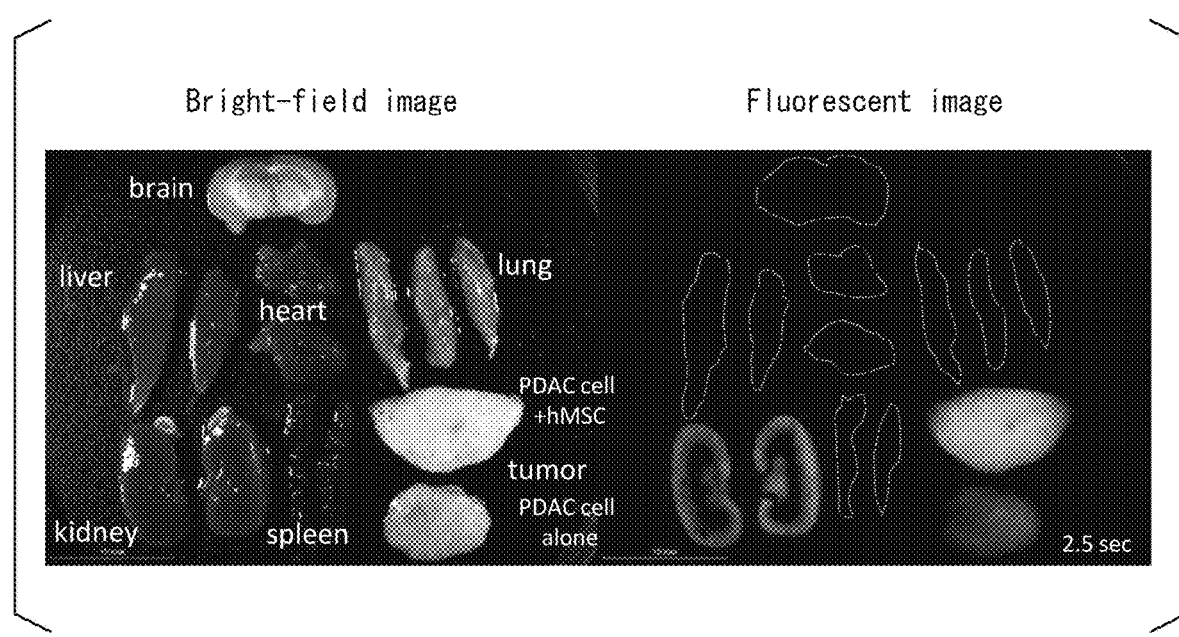
FIG. 18B is a bright-field image (left) and a fluorescent image (right) of various tissues and tumor tissues resected from a scirrhous pancreatic cancer model mouse that has been administered with an FAM-LL peptide in Test Example 6.
Figure 18C:
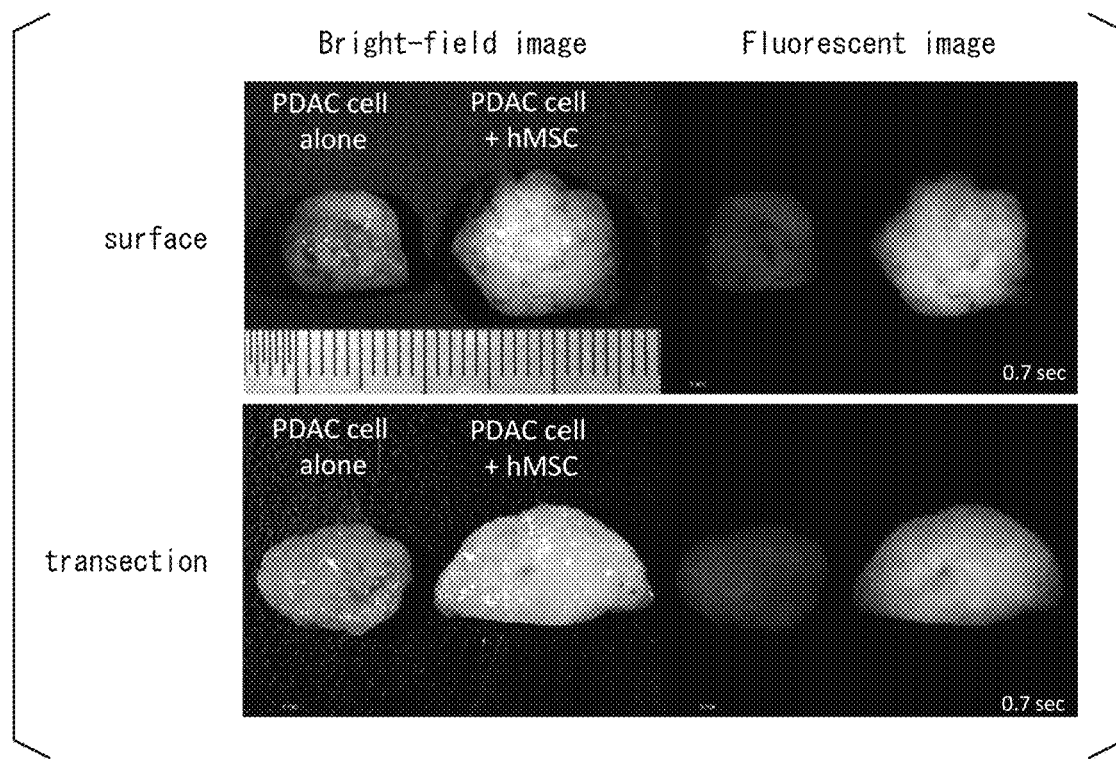
FIG. 18C is a series of bright-field images (left) and dark-field images (right) of various tumor tissues resected from a scirrhous pancreatic cancer model mouse that has been administered with an FAM-LL peptide in Test Example 6. The upper images are surface images, and the lower images are images of transections.
Figure 18D:
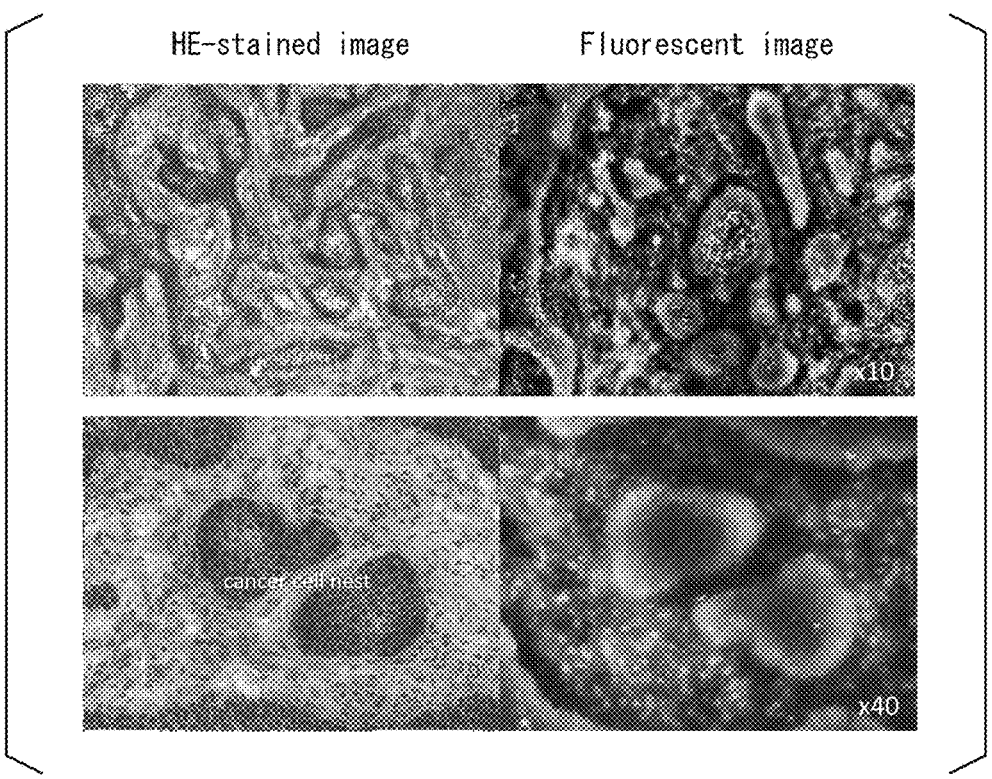
FIG. 18D is a series of hematoxylin-eosin (HE) stained images (left) and fluorescent images (right) of tumor tissue formed from human invasive pancreatic ductal adenocarcinoma (PDAC) cells and human mesenchymal stem cells (hMSC) in Test Example 6.
Figure 18E:
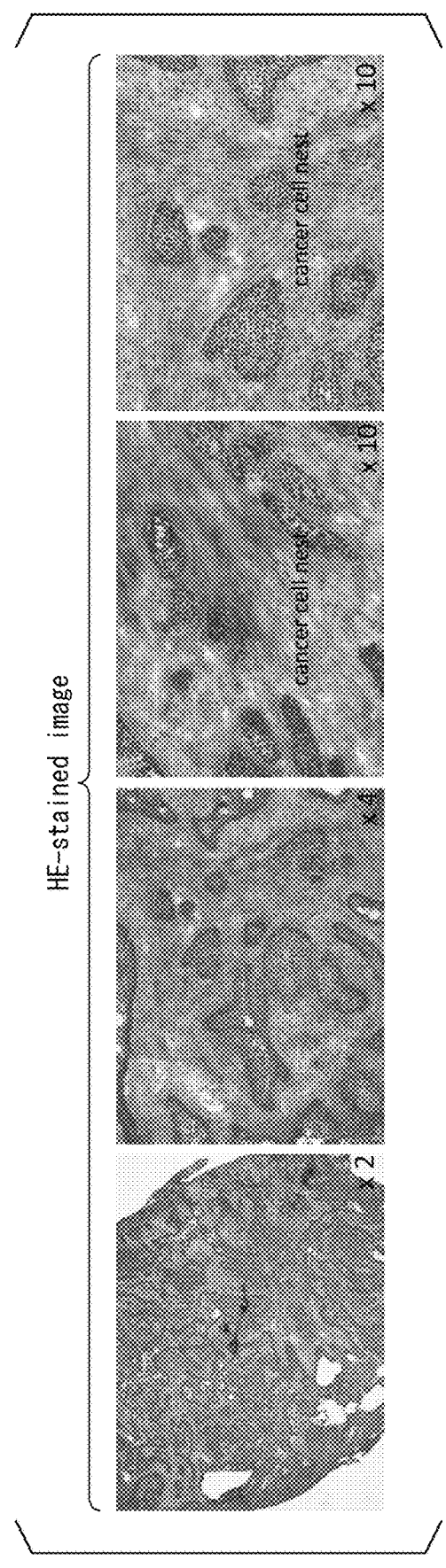
FIG. 18E is a series of HE-stained images of tumor tissue formed from human PDAC cells and hMSC in Test Example 6.
Figure 18F:
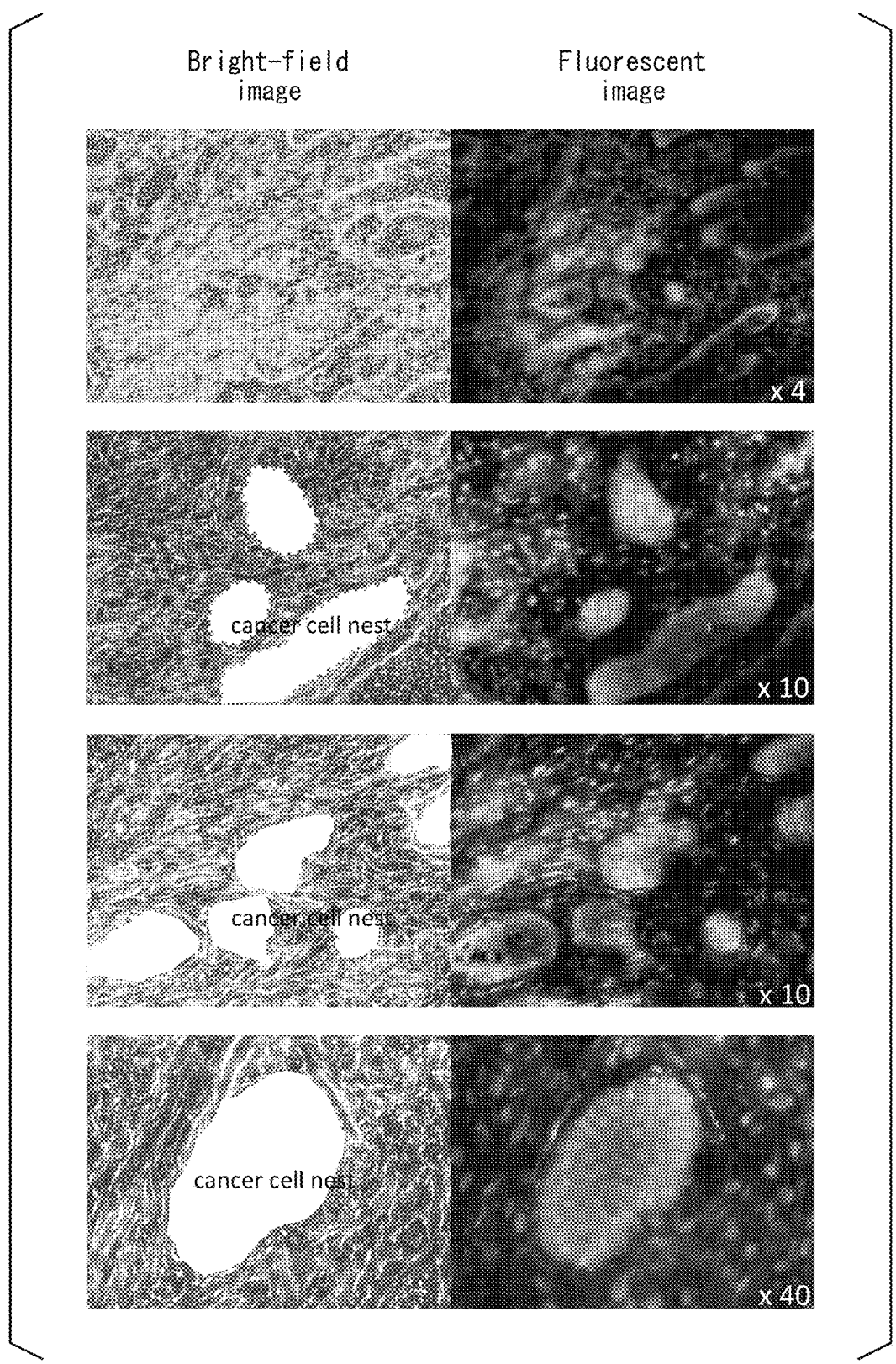
FIG. 18F is a series of bright-field images (left) and fluorescent images (right) of tumor tissue formed from human PDAC cells and hMSC in Test Example 6.

FAM-LL (200 µg) was injected into the caudal vein of the obtained scirrhous pancreatic cancer model mouse. Subsequently, the pharmacokinetics of the peptide 30 minutes after administration were analyzed by tissue analysis of the freshly dissected specimen of the peptide-administered mouse. The results are shown in FIG. 18A to FIG. 18F. FIG. 18A is a series of bright-field images (left and center) and a fluorescent image (right) of the tumors in the scirrhous pancreatic cancer model mouse. FIG. 18B is a bright-field image (left) and a fluorescent image (right) of various tissues and tumor tissues resected from the scirrhous pancreatic cancer model mouse. FIG. 18C is a series of bright-field images (left) and dark-field images (right) of various tumor tissues resected from the scirrhous pancreatic cancer model mouse. The upper images are images of the surfaces of each of the tumor tissues, and the lower images are images of transections of each of the tumor tissues. FIG. 18D is a series of hematoxylin-eosin (HE) stained images (left) and fluorescent images (right) of tumor tissue formed from human PDAC cells and hMSC. FIG. 18E is a series of HE-stained images of tumor tissue formed from human PDAC cells and hMSC. FIG. 18F is a series of bright-field images (left) and fluorescent images (right) of tumor tissue formed from human PDAC cells and hMSC.

Based on FIG. 18A to FIG. 18C, it is clear that FAM-LL exhibited strong absorption into the tumor tissue (and particularly the tumor tissue formed from human pancreatic cancer cells and hMSC). Further, FIG. 18D to FIG. 18F confirmed that in the tumor tissue formed from human PDAC cells and hMSC, tumor tissue having abundantly developed tumor-stroma interactions that imitates the tissue in a human pancreatic cancer patient, which is composed of cancer cell nests formed from cancer cells themselves in which the nuclei are accumulated in high density, and growth zones which surround the cancer cell nests and form peripheral fibroblast cell groups. Moreover, the FAM-LL exhibited strong absorption into the cancer cell nests inside the tumor tissue.

[Test Example 7] Evaluation Test of Selective Absorption of FAM-NmLL in Various Tissues of Scirrhous Pancreatic Cancer Model Mouse FAM-NmLL was administered to pancreatic cancer model mice having scirrhous carcinoma, and the selective absorption of the FAM-NmLL in various tissues of the mouse was confirmed. A scirrhous pancreatic cancer model mouse having scirrhous carcinoma that forms abundant tumor-stroma interactions was produced in accordance with the method disclosed in the above Reference Document 1. Specifically, a 6-week old NOD/SCID mouse (CLEA Japan Inc., Japan), a Pdx1-Cre/KRAS$^{G12D}$ (KC) mouse having a mutation in K-Ras, and a Pdx1-Cre/KRAS$^{G12D}$; p53$^{R172H}$ (KPC) mouse having pancreatic cancer-specific mutations in K-Ras and p53 were raised under pathogen-free conditions. A cell mixture containing BxPC3 cells ($1 \times 10^5$ cells) and hMSC ($1 \times 10^5$ cells) was injected subcutaneously into the NOD/SCID mouse, a cell mixture containing MIA-Paca2 cells ($1 \times 10^5$ cells) and hMSC ($1 \times 10^5$ cells) or a cell mixture containing AsPC1 cells ($1 \times 10^5$ cells) and hMSC ($1 \times 10^5$ cells) was injected subcutaneously into the KPC mouse, and a cell mixture containing Capan-2 cells ($1 \times 10^5$ cells) which are a cell line derived from human PDAC and hMSC ($1 \times 10^5$ cells) was injected subcutaneously into the KC mouse. By raising each mouse for 6 weeks from the time of cell injection, a scirrhous pancreatic cancer model mouse was obtained that had a tumor having abundantly developed tumor-stroma interactions that imitates the tissue in a human pancreatic cancer patient.

Figure 19A:
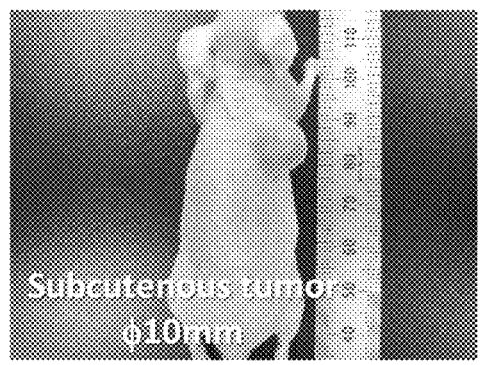
FIG. 19A is a bright-field image of a tumor in a scirrhous pancreatic cancer model mouse (using BxPC3 cells) in Test Example 7.
Figure 19B:
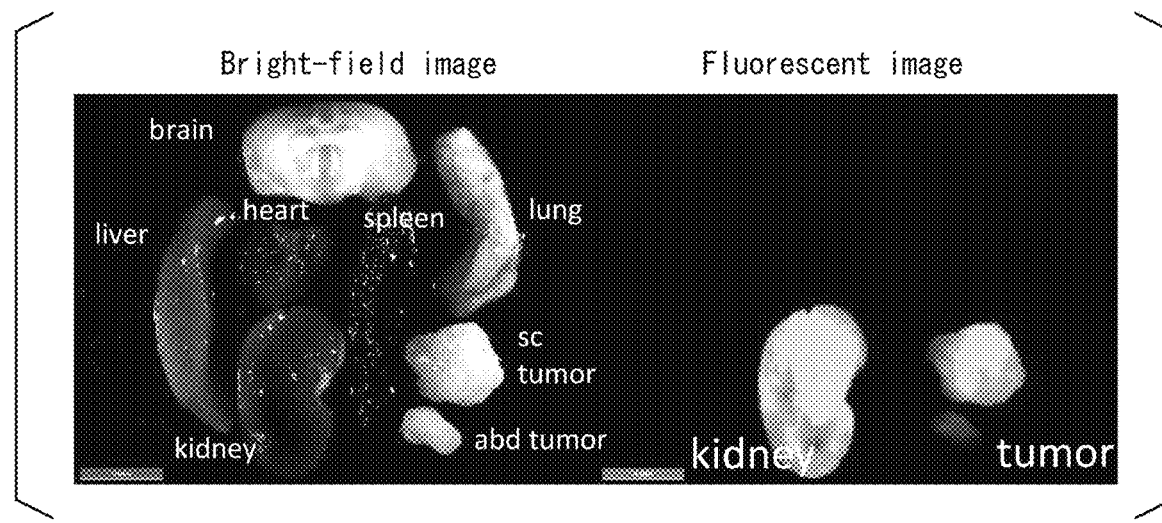
FIG. 19B is a bright-field image (left) and a fluorescent image (right) of various tissues and tumor tissues resected from a scirrhous pancreatic cancer model mouse (using BxPC3 cells) that has been administered with an FAM-NmLL peptide in Test Example 7.
Figure 19C:
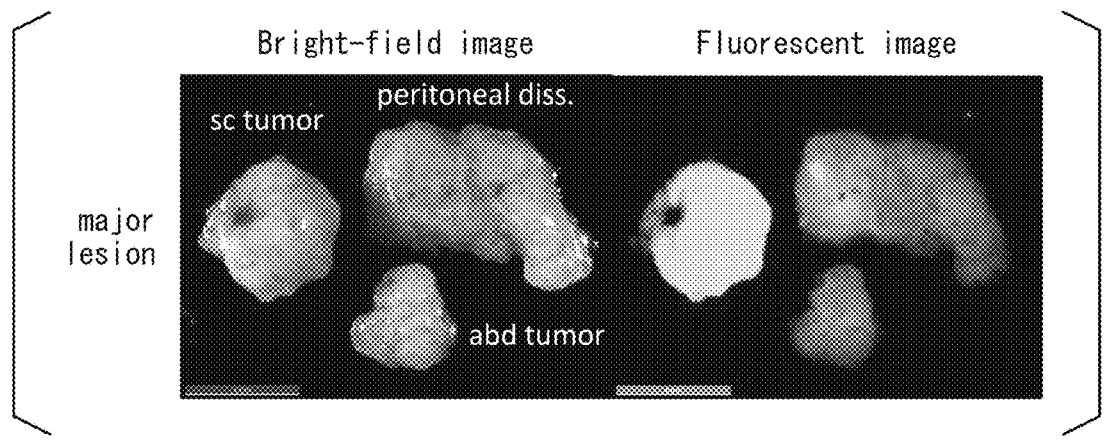
FIG. 19C is a bright-field image (left) and a fluorescent image (right) of the main lesions of a scirrhous pancreatic cancer model mouse (using BxPC3 cells) that has been administered with an FAM-NmLL peptide in Test Example 7.
Figure 19D:
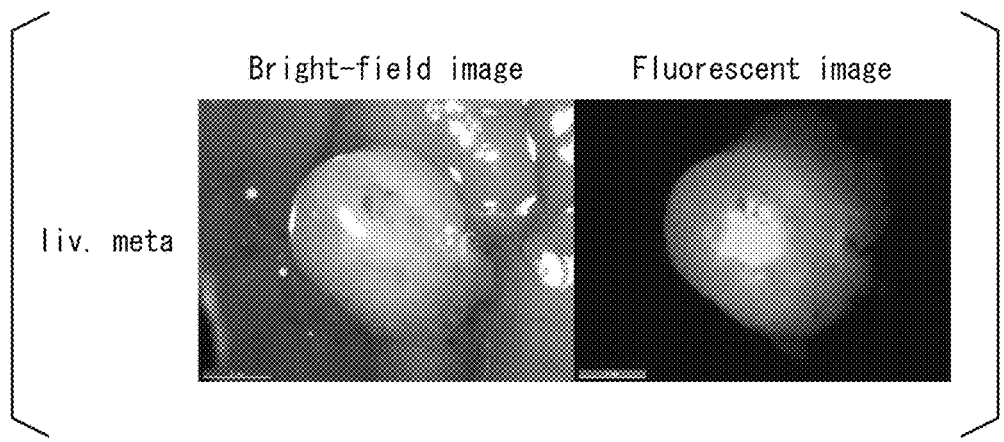
FIG. 19D is a bright-field image (left) and a fluorescent image (right) of a liver metastatic lesion in a scirrhous pancreatic cancer model mouse (using BxPC3 cells) that has been administered with an FAM-NmLL peptide in Test Example 7.
Figure 19E:
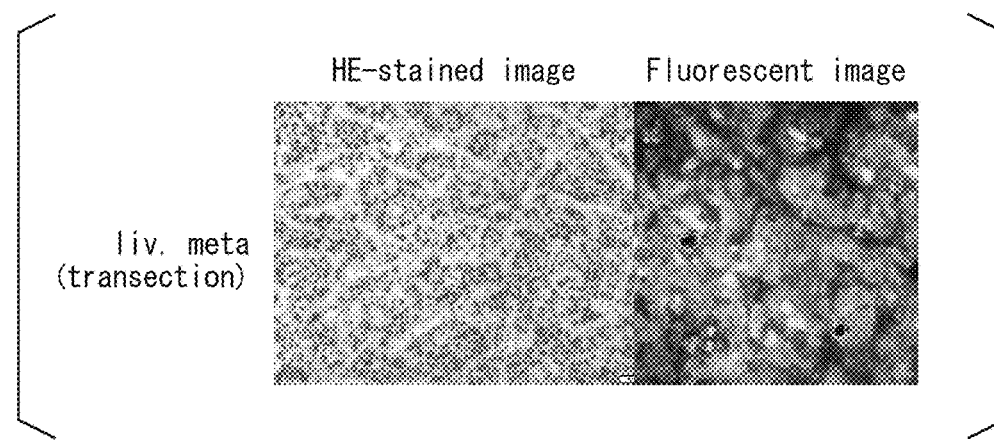
FIG. 19E is an HE-stained image (left) and a fluorescent image (right) of a transection of a liver metastatic lesion in a scirrhous pancreatic cancer model mouse (using BxPC3 cells) that has been administered with an FAM-NmLL peptide in Test Example 7.
Figure 19F:
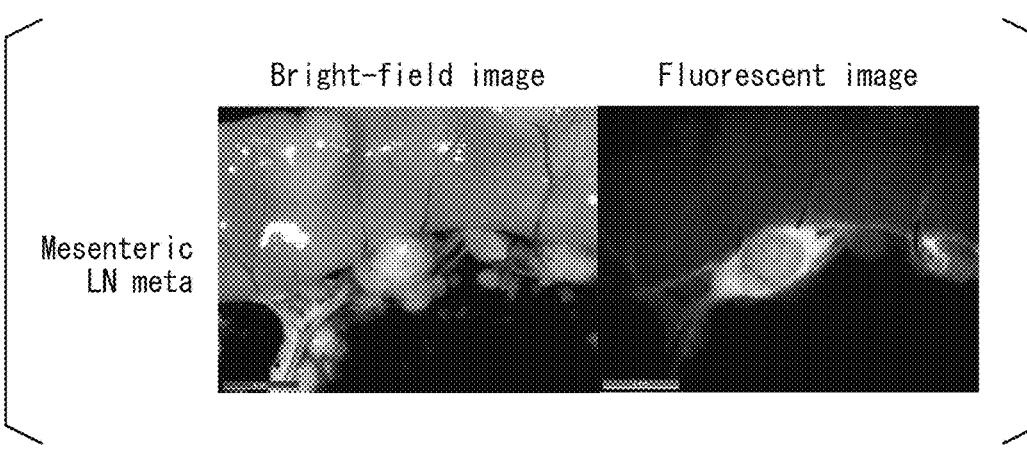
FIG. 19F is a bright-field image (left) and a fluorescent image (right) of a mesenteric lymph node metastatic lesion in a scirrhous pancreatic cancer model mouse (using BxPC3 cells) that has been administered with an FAM-NmLL peptide in Test Example 7.
Figure 20A:
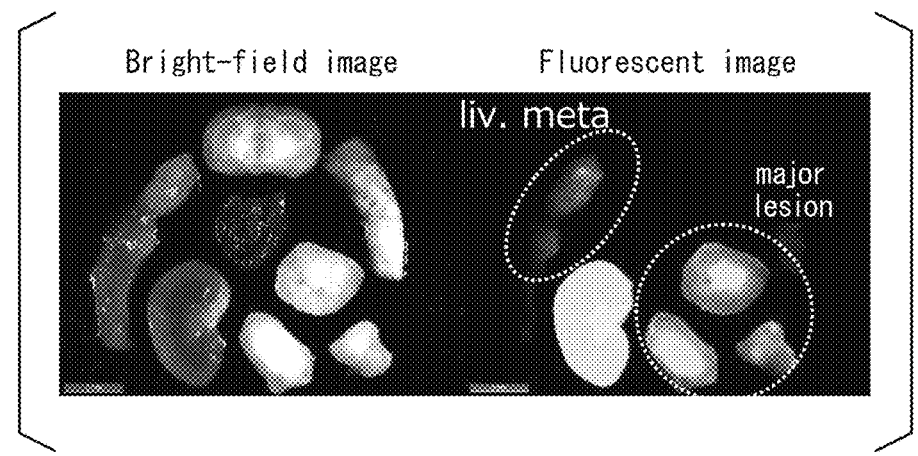
FIG. 20A is a bright-field image (left) and a fluorescent image (right) of various tissues and tumor tissues resected from a scirrhous pancreatic cancer model mouse (using MIA-Paca2 cells) that has been administered with an FAM-NmLL peptide in Test Example 7.
Figure 20B:
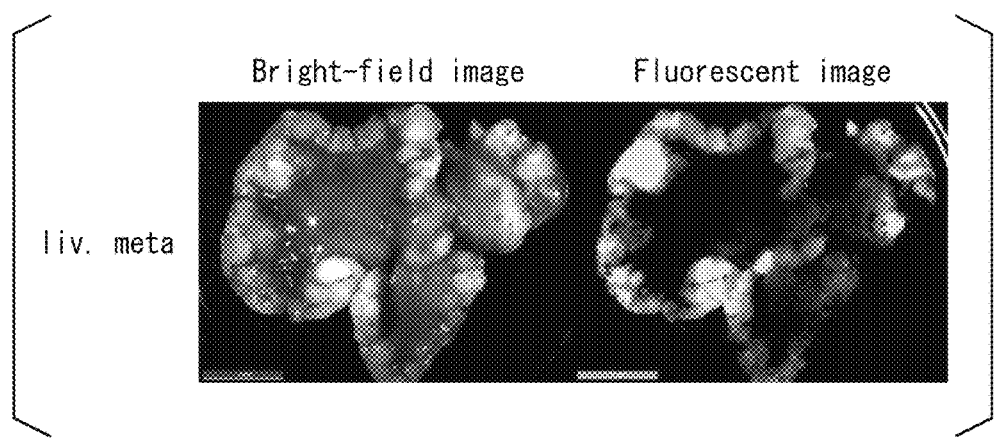
FIG. 20B is a bright-field image (left) and a fluorescent image (right) of a liver metastatic lesion in a scirrhous pancreatic cancer model mouse (using MIA-Paca2 cells) that has been administered with an FAM-NmLL peptide in Test Example 7.
Figure 20C:
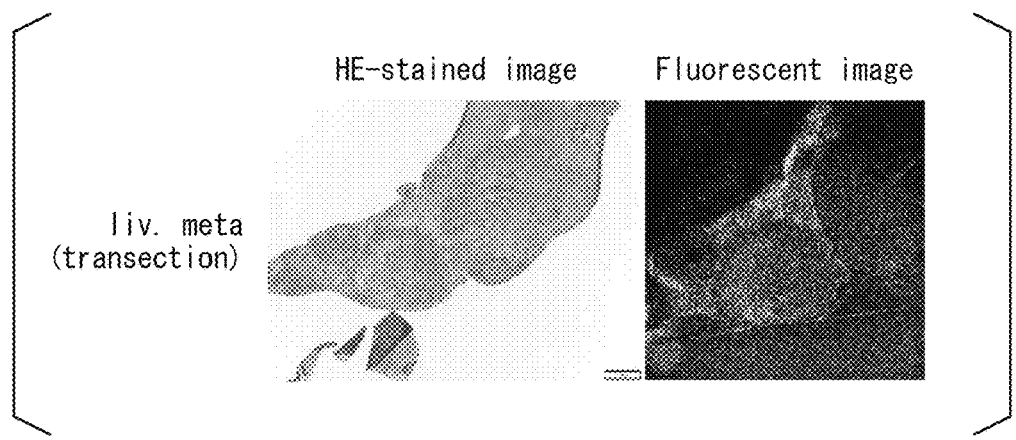
FIG. 20C is an HE-stained image (left) and a fluorescent image (right) of a transection of a liver metastatic lesion in a scirrhous pancreatic cancer model mouse (using MIA-Paca2 cells) that has been administered with an FAM-NmLL peptide in Test Example 7.
Figure 21:
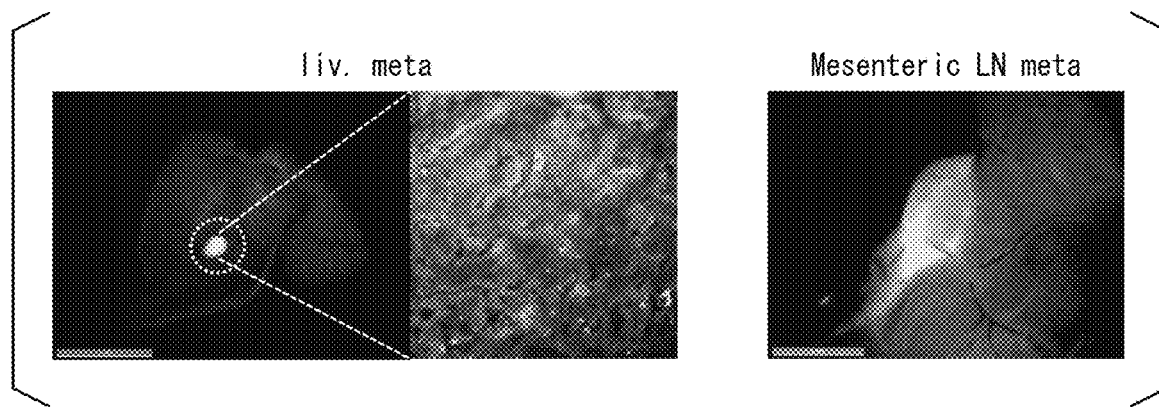
FIG. 21 is a series of fluorescent images of a liver metastatic lesion and a mesenteric lymph node metastatic lesion in a scirrhous pancreatic cancer model mouse (using AsPC1 cells) that has been administered with an FAM-NmLL peptide in Test Example 7. In the fluorescent image of the liver metastatic lesion, the image on the right side is an enlargement of the image on the left side.
Figure 22A:
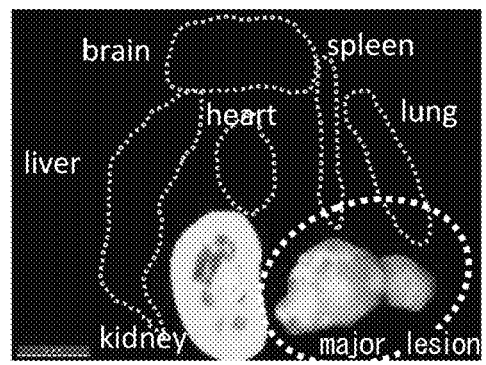
FIG. 22A is a fluorescent image of various tissues and tumor tissues resected from a scirrhous pancreatic cancer model mouse (using Capan-2 cells) that has been administered with an FAM-NmLL peptide in Test Example 7.
Figure 22B:
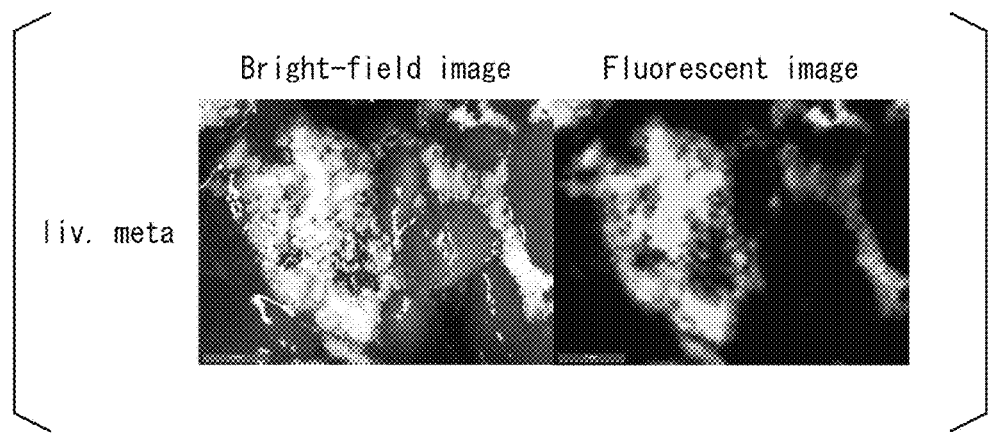
FIG. 22B is a bright-field image (left) and a fluorescent image (right) of a liver metastatic lesion in a scirrhous pancreatic cancer model mouse (using Capan-2 cells) that has been administered with an FAM-NmLL peptide in Test Example 7.

FAM-NmLL (200 µg) was injected into the caudal vein of each of the obtained scirrhous pancreatic cancer model mice. Subsequently, the pharmacokinetics of the peptide 30 minutes after administration were analyzed by tissue analysis of the freshly dissected specimen of the peptide-administered mouse. The results in the scirrhous pancreatic cancer model mouse that used the cell mixture of BxPC3 cells and hMSC are shown in FIG. 19A to FIG. 19F. In FIG. 19C, "peritoneal diss." is an abbreviation for "peritoneal disseminated tumor". In FIG. 19F, "mesenteric LN meta" is an abbreviation for "mesenteric lymph nodes metastatic tumor", and describes a tumor that has metastasized to the mesenteric lymph nodes. These same abbreviations are also used in subsequent figures. The results in the scirrhous pancreatic cancer model mouse that used the cell mixture of MIA-Paca2 cells and hMSC are shown in FIG. 20A to FIG. 20C. The results in the scirrhous pancreatic cancer model mouse that used the cell mixture of AsPC1 cells and hMSC are shown in FIG. 21. The results in the scirrhous pancreatic cancer model mouse that used the cell mixture of Capan-2 cells and hMSC are shown in FIG. 22A and FIG. 22B.

Based on FIG. 19A to FIG. 22B, it is evident that FAM-NmLL exhibited strong absorption into the tumor tissues (main lesions and metastatic lesions) in all of the mouse models. Further, the FAM-NmLL exhibited strong absorption into the cancer cell nests inside the tumor tissues in all of the mouse models.

[Test Example 8] Confirmation Test of Accumulation of Various Peptide in Pancreatic Cancer Cells and Other Cancer Cells Tests were conducted to confirm the accumulation of various peptides into each of the cells shown below in Table 13. Further, the peptides shown below in Table 14 were used.

TABLE 13

| Cell type | Cell name | Derivation |
|---|---|---|
| Pancreatic cancer cells | BxPC3 | Cell line derived from human PDAC |
| | PK-8 | Cell line derived from human PDAC |
| | AsPC1 | Cell line derived from human PDAC |
| Lung cancer cells | H2110 | Adenocarcinoma cell line from human non-small-cell lung cancer system |

TABLE 14

| Type | Amino acid sequence | SEQ ID NO: |
|---|---|---|
| FLC-PCPP11 | [FLC]-RRPTTWHKP | 4 |
| FLC-NmLL | [FLC]-R-mR-PTTWHKP-G-RRPTTWHKP | 18 |
| NmL-Cys(-FLC)-L | R-mR-PTTWHKP-C(-[FLC])-RRPTTWHKP | 27 |
| NmL-Cys(-FLC)LL | R-mR-PTTWHKP-C(-[FLC])-RRPTTWHKP-G-RRPTTWHKP | 28 |
| L(-R)L-Cys(-FLC)-L | RPTTWHKP-G-RRPTTWHKP-C(-[FLC])-RRPTTWHKP | 29 |
| L(-R)-Cys(-FLC)-L-Cys(-FLC)-L | RPTTWHKP-C(-[FLC])-RRPTTWHKP-C(-[FLC])-RRPTTWHKP | 30 |
| L(-R)L-Lys(-FLC)-L | RPTTWHKP-G-RRPTTWHKP-K(-[FLC])-RRPTTWHKP | 31 |

Figure 23:
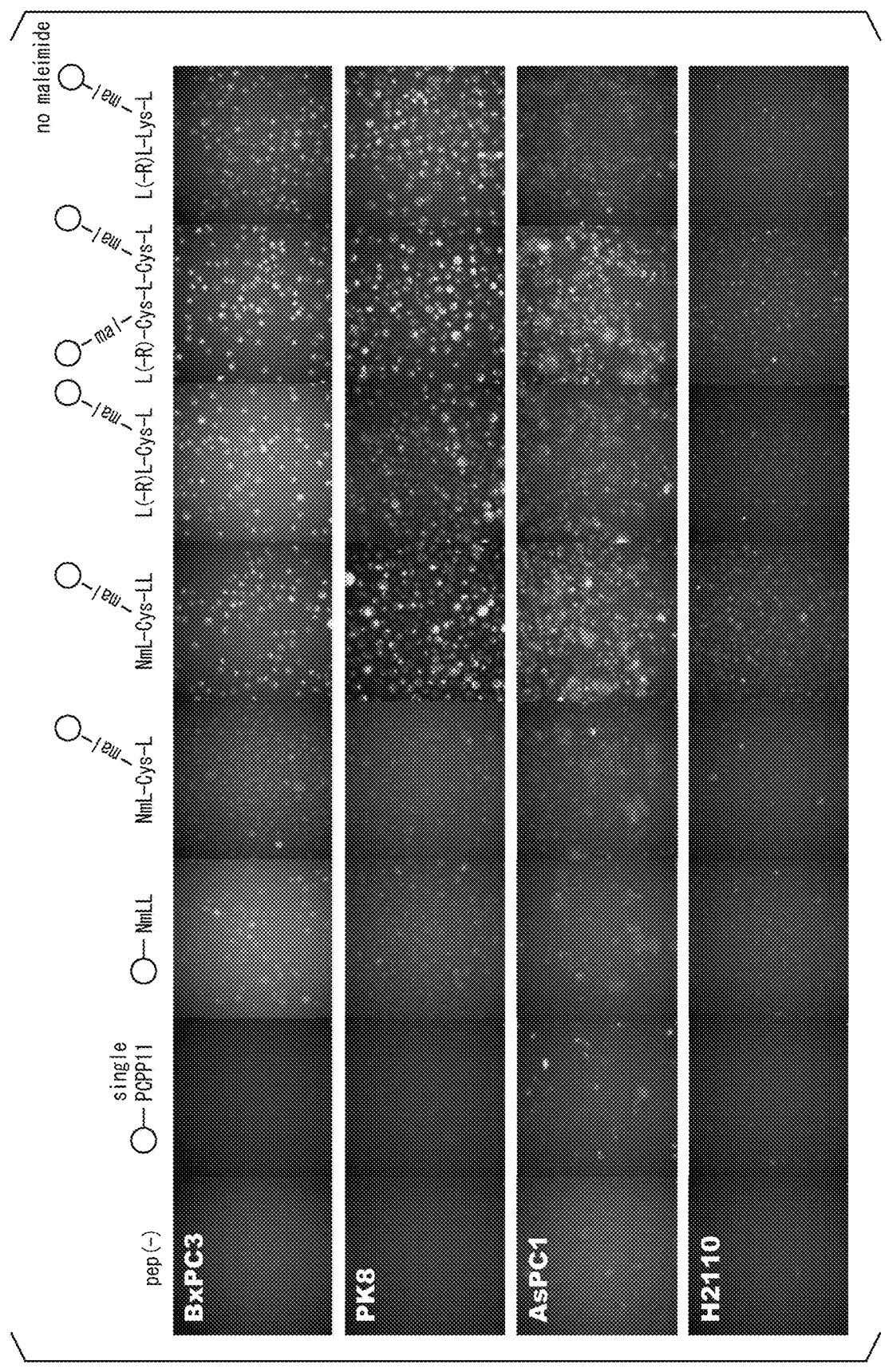
FIG. 23 is a series of fluorescence microscope images of various cells to which various peptides have been added in Test Example 8.

Each peptide was added to each of the cells shown in Table 13 in an amount sufficient to achieve a final concentration in the medium of 2 µM, and following cultivation of the cells at 37° C. for 2 hours, the sample was washed 3 times with a medium containing no peptide to remove any peptide within the medium. Subsequently, the incorporation of each of the peptides into each of the cells was evaluated visually using an inverted fluorescence microscope. Prior to the microscopic examination, the culture supernatant to which the peptide had been added was removed, and following washing three times with 1×PBS (−), a trypsin treatment was conducted to remove the adherent cells, and the resultant was immediately transferred into a new 96-well plate and once again suspended in fresh culture solution before the microscopic examination was performed. The results are shown in FIG. 23. In FIG. 23, "pep(−)" indicates the control cells to which no peptide was administered, and "single PCPP11" indicates cells to which FLC (fluorescein)-PCPP11 had been added. Further, "mal" indicates a maleimide group, with the peptide and the FLC bonded together by forming a covalent bond between the thiol group (—SH) of a cysteine residue and a maleimide group introduced into the FLC.

Based on FIG. 23, it is evident that with FLC-NmLL, NmL-Cys(-FLC)-L, NmL-Cys(-FLC)-LL, L(-R)L-Cys(-FLC)-L, L(-R)-Cys(-FLC)-L-Cys(-FLC)-L, and L(-R)L-Lys(-FLC)-L, stronger fluorescence was detected in each of the pancreatic cancer cells compared with FLC-PCPP11. On the other hand, in the H2110 cells (lung adenocarcinoma cells), which although being a similar adenocarcinoma system to the cell lines derived from PDAC have a different genesis, almost no fluorescence was detected. Further, in the case of NmL-Cys(-FLC)-LL, L(-R)L-Cys(-FLC)-L, L(-R)-Cys(-FLC)-L-Cys(-FLC)-L and L(-R)L-Lys(-FLC)-L, particularly strong fluorescence was detected in all of the pancreatic cancer cells.

INDUSTRIAL APPLICABILITY

A peptide of an embodiment of the present invention exhibits a high degree of accumulation in cancer cells or cancer tissue in the digestive system, and has excellent in vivo degradation resistance. By using the peptide of this embodiment, a target substance can be delivered simply and efficiently to cancer cells or cancer tissue in the digestive system.

The invention claimed is:

1. A peptide composed of an amino acid sequence represented by general formula (I) shown below, and having a high degree of accumulation in cancer cells or cancer tissue in a digestive system:

$$X^{11}-(Y^{11}-X^{12})_{n11} \quad \text{General formula (I):}$$

wherein in general formula (I), $X^{11}$ is a peptide residue composed of an amino acid sequence of (a) or (b) below:

(a) an amino acid sequence represented by any of SEQ ID NOs: 1 to 3,
(b) an amino acid sequence including a sequence in which one or two amino acids have been deleted, substituted or added in an amino acid sequence represented by any of SEQ ID NOs: 1 to 3;
$Y^{11}$ is a peptide linker composed of an amino acid residue of at least 1 but not more than 10 amino acids, wherein each amino acid residue is independently a glycine residue, a proline residue, a serine residue, a cysteine residue or a lysine residue;

$X^{12}$ is either a peptide residue composed of an amino acid sequence of (a) or (b) above, or a retro-inverso peptide residue thereof; and n11 represents an integer of at least 1 but not more than 9.

2. The peptide according to claim 1, wherein $Y^{11}$ is a peptide linker composed of an amino acid residue at least 1 but not more than 10 amino acids, and each amino acid residue is independently a glycine residue, a cysteine residue or a lysine residue.

3. The peptide according to claim 1, wherein n11 is an integer of at least 1 but not more than 4.

4. The peptide according to claim 1, wherein either $X^{11}$ and $X^{12}$ are peptide residues composed of the same amino acid sequence, or $X^{12}$ is a retro-inverso peptide residue of $X^{11}$.

5. The peptide according to claim 1, wherein the peptide is composed of an amino acid sequence represented by any of SEQ ID NOs: 15 to 31.

6. A peptide-drug-conjugate comprising the peptide of claim 1 and a biologically active substance.

7. A pharmaceutical composition comprising the peptide-drug-conjugate of claim 6.

8. The pharmaceutical composition according to claim 7, wherein the biologically active substance is an anticancer drug.

9. A labeled peptide comprising the peptide of claim 1 and a labeling substance.

10. The labeled peptide according to claim 9, wherein the labeling substance is a stable isotope, a radioisotope, or a fluorescent substance.

11. An imaging composition comprising the labeled peptide of claim 9.

12. A method for treatment of cancer of the digestive system, comprising administering an effective amount of the peptide-drug-conjugate of claim 6.

13. The method according to claim 12, wherein the cancer of the digestive system is pancreatic cancer.

14. A method for imaging cancer cells or cancer tissue in the digestive system, comprising:
administering an imaging composition of claim 11; and detecting the imaging composition.

15. The method according to claim 14, wherein the cancer cells or cancer tissue in the digestive system are pancreatic cancer cells or pancreatic cancer tissue.

16. A nucleic acid that encodes the peptide of claim 1.

17. A vector comprising the nucleic acid of claim 16.

18. A peptide-drug-conjugate expression vector having the nucleic acid of claim 16 and a nucleic acid that encodes a biologically active substance.

19. A labeled peptide expression vector comprising the nucleic acid of claim 16 and a nucleic acid that encodes a labeling substance.

* * * * *

SEQUENCE LISTING

```
<160> NUMBER OF SEQ ID NOS: 48

<210> SEQ ID NO 1
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (2)..(2)
<223> OTHER INFORMATION: Xaa indicates Arg or Methyl-Arg.

<400> SEQUENCE: 1

Arg Xaa Pro Thr Thr Trp His Lys Pro
1               5

<210> SEQ ID NO 2
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (2)..(2)
<223> OTHER INFORMATION: Xaa indicates Arg or Methyl-Arg.
<220> FEATURE:
<221> NAME/KEY: MISC_FEATURE
<222> LOCATION: (3)..(3)
<223> OTHER INFORMATION: Xaa indicates Arg or Methyl-Arg.

<400> SEQUENCE: 2
```

```
Ala Xaa Xaa Tyr Thr Trp Ile Arg Ala
1               5

<210> SEQ ID NO 3
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (2)..(2)
<223> OTHER INFORMATION: Xaa indicates Ala or Methyl-Ala.

<400> SEQUENCE: 3

Arg Xaa Trp Arg Gln Cys Arg Trp Arg
1               5

<210> SEQ ID NO 4
<211> LENGTH: 9
<212> TYPE: PRT
<213> ORGANISM: Artificial Sequence
<220> FEATURE:
<223> OTHER INFORMATION: Synthesized

<400> SEQUENCE: 4

Arg Arg Pro Thr Thr Trp His Lys Pro
1               5

<210> SEQ ID NO 5
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (2)..(2)
<223> OTHER INFORMATION: Xaa indicates Methyl-Arg.

<400> SEQUENCE: 5

Arg Xaa Pro Thr Thr Trp His Lys Pro
1               5

<210> SEQ ID NO 6
<211> LENGTH: 9
<212> TYPE: PRT
<213> ORGANISM: Artificial Sequence
<220> FEATURE:
<223> OTHER INFORMATION: Synthesized

<400> SEQUENCE: 6

Ala Arg Arg Tyr Thr Trp Ile Arg Ala
1               5

<210> SEQ ID NO 7
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (2)..(2)
<223> OTHER INFORMATION: Xaa indicates Methyl-Arg.

<400> SEQUENCE: 7

Ala Xaa Arg Tyr Thr Trp Ile Arg Ala
```

```
<210> SEQ ID NO 8
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (3)..(3)
<223> OTHER INFORMATION: Xaa indicates Methyl-Arg.

<400> SEQUENCE: 8

Ala Arg Xaa Tyr Thr Trp Ile Arg Ala
1               5

<210> SEQ ID NO 9
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (2)..(2)
<223> OTHER INFORMATION: Xaa indicates Methyl-Arg.
<220> FEATURE:
<221> NAME/KEY: MISC_FEATURE
<222> LOCATION: (3)..(3)
<223> OTHER INFORMATION: Xaa indicates Methyl-Arg.

<400> SEQUENCE: 9

Ala Xaa Xaa Tyr Thr Trp Ile Arg Ala
1               5

<210> SEQ ID NO 10
<211> LENGTH: 9
<212> TYPE: PRT
<213> ORGANISM: Artificial Sequence
<220> FEATURE:
<223> OTHER INFORMATION: Synthesized

<400> SEQUENCE: 10

Arg Ala Trp Arg Gln Cys Arg Trp Arg
1               5

<210> SEQ ID NO 11
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (2)..(2)
<223> OTHER INFORMATION: Xaa indicates Methyl-Ala.

<400> SEQUENCE: 11

Arg Xaa Trp Arg Gln Cys Arg Trp Arg
1               5

<210> SEQ ID NO 12
<211> LENGTH: 6
<212> TYPE: PRT
<213> ORGANISM: Artificial Sequence
<220> FEATURE:
<223> OTHER INFORMATION: Synthesized

<400> SEQUENCE: 12
```

```
Arg Pro Thr Thr Trp His
1               5

<210> SEQ ID NO 13
<211> LENGTH: 8
<212> TYPE: PRT
<213> ORGANISM: Artificial Sequence
<220> FEATURE:
<223> OTHER INFORMATION: Synthesized

<400> SEQUENCE: 13

Arg Pro Thr Thr Trp His Lys Pro
1               5

<210> SEQ ID NO 14
<211> LENGTH: 7
<212> TYPE: PRT
<213> ORGANISM: Artificial Sequence
<220> FEATURE:
<223> OTHER INFORMATION: Synthesized

<400> SEQUENCE: 14

Arg Arg Pro Thr Thr Trp His
1               5

<210> SEQ ID NO 15
<211> LENGTH: 19
<212> TYPE: PRT
<213> ORGANISM: Artificial Sequence
<220> FEATURE:
<223> OTHER INFORMATION: Synthesized

<400> SEQUENCE: 15

Arg Arg Pro Thr Thr Trp His Lys Pro Gly Arg Arg Pro Thr Thr Trp
1               5                   10                  15

His Lys Pro

<210> SEQ ID NO 16
<211> LENGTH: 29
<212> TYPE: PRT
<213> ORGANISM: Artificial Sequence
<220> FEATURE:
<223> OTHER INFORMATION: Synthesized

<400> SEQUENCE: 16

Arg Arg Pro Thr Thr Trp His Lys Pro Gly Arg Arg Pro Thr Thr Trp
1               5                   10                  15

His Lys Pro Gly Arg Arg Pro Thr Thr Trp His Lys Pro
            20                  25

<210> SEQ ID NO 17
<211> LENGTH: 19
<212> TYPE: PRT
<213> ORGANISM: Artificial Sequence
<220> FEATURE:
<223> OTHER INFORMATION: Synthesized

<400> SEQUENCE: 17

Arg Arg Pro Thr Thr Trp His Lys Pro Gly Pro Lys His Trp Thr Thr
1               5                   10                  15

Pro Arg Arg

<210> SEQ ID NO 18
<211> LENGTH: 19
```

```
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (2)..(2)
<223> OTHER INFORMATION: Xaa indicates Methyl-Arg.

<400> SEQUENCE: 18

Arg Xaa Pro Thr Thr Trp His Lys Pro Gly Arg Arg Pro Thr Thr Trp
1               5                   10                  15

His Lys Pro

<210> SEQ ID NO 19
<211> LENGTH: 19
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (2)..(2)
<223> OTHER INFORMATION: Xaa indicates Methyl-Arg.

<400> SEQUENCE: 19

Arg Xaa Pro Thr Thr Trp His Lys Pro Gly Pro Lys His Trp Thr Thr
1               5                   10                  15

Pro Arg Arg

<210> SEQ ID NO 20
<211> LENGTH: 17
<212> TYPE: PRT
<213> ORGANISM: Artificial Sequence
<220> FEATURE:
<223> OTHER INFORMATION: Synthesized

<400> SEQUENCE: 20

Arg Pro Thr Thr Trp His Lys Pro Gly Arg Pro Thr Thr Trp His Lys
1               5                   10                  15

Pro

<210> SEQ ID NO 21
<211> LENGTH: 18
<212> TYPE: PRT
<213> ORGANISM: Artificial Sequence
<220> FEATURE:
<223> OTHER INFORMATION: Synthesized

<400> SEQUENCE: 21

Arg Pro Thr Thr Trp His Lys Pro Gly Arg Arg Pro Thr Thr Trp His
1               5                   10                  15

Lys Pro

<210> SEQ ID NO 22
<211> LENGTH: 15
<212> TYPE: PRT
<213> ORGANISM: Artificial Sequence
<220> FEATURE:
<223> OTHER INFORMATION: Synthesized

<400> SEQUENCE: 22

Arg Arg Pro Thr Thr Trp His Gly Arg Arg Pro Thr Thr Trp His
1               5                   10                  15
```

```
<210> SEQ ID NO 23
<211> LENGTH: 17
<212> TYPE: PRT
<213> ORGANISM: Artificial Sequence
<220> FEATURE:
<223> OTHER INFORMATION: Synthesized

<400> SEQUENCE: 23

Arg Arg Pro Thr Thr Trp His Gly Arg Arg Pro Thr Thr Trp His Lys
1               5                   10                  15
Pro

<210> SEQ ID NO 24
<211> LENGTH: 17
<212> TYPE: PRT
<213> ORGANISM: Artificial Sequence
<220> FEATURE:
<223> OTHER INFORMATION: Synthesized

<400> SEQUENCE: 24

Arg Arg Pro Thr Thr Trp His Lys Pro Gly Arg Arg Pro Thr Thr Trp
1               5                   10                  15
His

<210> SEQ ID NO 25
<211> LENGTH: 17
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (2)..(2)
<223> OTHER INFORMATION: Xaa indicates Methyl-Arg.

<400> SEQUENCE: 25

Arg Xaa Pro Thr Thr Trp His Lys Pro Gly Arg Arg Pro Thr Thr Trp
1               5                   10                  15
His

<210> SEQ ID NO 26
<211> LENGTH: 17
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (2)..(2)
<223> OTHER INFORMATION: Xaa indicates Methyl-Arg.

<400> SEQUENCE: 26

Arg Xaa Pro Thr Thr Trp His Gly Arg Arg Pro Thr Thr Trp His Lys
1               5                   10                  15
Pro

<210> SEQ ID NO 27
<211> LENGTH: 19
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (2)..(2)
<223> OTHER INFORMATION: Xaa indicates Methyl-Arg.
```

-continued

```
<400> SEQUENCE: 27

Arg Xaa Pro Thr Thr Trp His Lys Pro Cys Arg Arg Pro Thr Thr Trp
1               5                   10                  15

His Lys Pro

<210> SEQ ID NO 28
<211> LENGTH: 29
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (2)..(2)
<223> OTHER INFORMATION: Xaa indicates Methyl-Arg.

<400> SEQUENCE: 28

Arg Xaa Pro Thr Thr Trp His Lys Pro Cys Arg Arg Pro Thr Thr Trp
1               5                   10                  15

His Lys Pro Gly Arg Arg Pro Thr Thr Trp His Lys Pro
            20                  25

<210> SEQ ID NO 29
<211> LENGTH: 28
<212> TYPE: PRT
<213> ORGANISM: Artificial Sequence
<220> FEATURE:
<223> OTHER INFORMATION: Synthesized

<400> SEQUENCE: 29

Arg Pro Thr Thr Trp His Lys Pro Gly Arg Arg Pro Thr Thr Trp His
1               5                   10                  15

Lys Pro Cys Arg Arg Pro Thr Thr Trp His Lys Pro
            20                  25

<210> SEQ ID NO 30
<211> LENGTH: 28
<212> TYPE: PRT
<213> ORGANISM: Artificial Sequence
<220> FEATURE:
<223> OTHER INFORMATION: Synthesized

<400> SEQUENCE: 30

Arg Pro Thr Thr Trp His Lys Pro Cys Arg Arg Pro Thr Thr Trp His
1               5                   10                  15

Lys Pro Cys Arg Arg Pro Thr Thr Trp His Lys Pro
            20                  25

<210> SEQ ID NO 31
<211> LENGTH: 28
<212> TYPE: PRT
<213> ORGANISM: Artificial Sequence
<220> FEATURE:
<223> OTHER INFORMATION: Synthesized

<400> SEQUENCE: 31

Arg Pro Thr Thr Trp His Lys Pro Gly Arg Arg Pro Thr Thr Trp His
1               5                   10                  15

Lys Pro Lys Arg Arg Pro Thr Thr Trp His Lys Pro
            20                  25

<210> SEQ ID NO 32
<211> LENGTH: 57
<212> TYPE: DNA
```

```
<213> ORGANISM: Artificial Sequence
<220> FEATURE:
<223> OTHER INFORMATION: Synthesized

<400> SEQUENCE: 32
cggcggccga ctacgtggca taagcctggg cggcggccga ctacgtggca taagcct        57

<210> SEQ ID NO 33
<211> LENGTH: 87
<212> TYPE: DNA
<213> ORGANISM: Artificial Sequence
<220> FEATURE:
<223> OTHER INFORMATION: Synthesized

<400> SEQUENCE: 33
cggcggccga ctacgtggca taagcctggg cggcggccga ctacgtggca taagcctggg    60
cggcggccga ctacgtggca taagcct                                        87

<210> SEQ ID NO 34
<211> LENGTH: 57
<212> TYPE: DNA
<213> ORGANISM: Artificial Sequence
<220> FEATURE:
<223> OTHER INFORMATION: Synthesized

<400> SEQUENCE: 34
cggcggccga ctacgtggca taagcctggg cctaagcatt ggacgactcc gcggcgg        57

<210> SEQ ID NO 35
<211> LENGTH: 6
<212> TYPE: PRT
<213> ORGANISM: Artificial Sequence
<220> FEATURE:
<223> OTHER INFORMATION: Synthesized

<400> SEQUENCE: 35

Thr Thr Trp His Lys Pro
1               5

<210> SEQ ID NO 36
<211> LENGTH: 4
<212> TYPE: PRT
<213> ORGANISM: Artificial Sequence
<220> FEATURE:
<223> OTHER INFORMATION: Synthesized

<400> SEQUENCE: 36

Thr Thr Trp His
1

<210> SEQ ID NO 37
<211> LENGTH: 3
<212> TYPE: PRT
<213> ORGANISM: Artificial Sequence
<220> FEATURE:
<223> OTHER INFORMATION: Synthesized

<400> SEQUENCE: 37

Thr Trp His
1

<210> SEQ ID NO 38
<211> LENGTH: 2
<212> TYPE: PRT
<213> ORGANISM: Artificial Sequence
<220> FEATURE:
```

<223> OTHER INFORMATION: Synthesized

<400> SEQUENCE: 38

Trp His
1

<210> SEQ ID NO 39
<211> LENGTH: 16
<212> TYPE: PRT
<213> ORGANISM: Artificial Sequence
<220> FEATURE:
<223> OTHER INFORMATION: Synthesized

<400> SEQUENCE: 39

Thr Thr Trp His Lys Pro Gly Arg Arg Pro Thr Thr Trp His Lys Pro
1               5                   10                  15

<210> SEQ ID NO 40
<211> LENGTH: 18
<212> TYPE: PRT
<213> ORGANISM: Artificial Sequence
<220> FEATURE:
<223> OTHER INFORMATION: Synthesized

<400> SEQUENCE: 40

Arg Pro Thr Thr Trp His Lys Pro Gly Pro Lys His Trp Thr Thr Pro
1               5                   10                  15

Arg Arg

<210> SEQ ID NO 41
<211> LENGTH: 16
<212> TYPE: PRT
<213> ORGANISM: Artificial Sequence
<220> FEATURE:
<223> OTHER INFORMATION: Synthesized

<400> SEQUENCE: 41

Thr Thr Trp His Lys Pro Gly Pro Lys His Trp Thr Thr Pro Arg Arg
1               5                   10                  15

<210> SEQ ID NO 42
<211> LENGTH: 23
<212> TYPE: PRT
<213> ORGANISM: Artificial Sequence
<220> FEATURE:
<223> OTHER INFORMATION: Synthesized

<400> SEQUENCE: 42

Cys Gly Gly Gly Arg Arg Pro Thr Thr Trp His Lys Pro Gly Arg Arg
1               5                   10                  15

Pro Thr Thr Trp His Lys Pro
            20

<210> SEQ ID NO 43
<211> LENGTH: 5
<212> TYPE: PRT
<213> ORGANISM: Artificial Sequence
<220> FEATURE:
<223> OTHER INFORMATION: Synthesized

<400> SEQUENCE: 43

Arg Pro Thr Thr Trp
1               5

<210> SEQ ID NO 44

```
<211> LENGTH: 5
<212> TYPE: PRT
<213> ORGANISM: Artificial Sequence
<220> FEATURE:
<223> OTHER INFORMATION: Synthesized

<400> SEQUENCE: 44

Pro Thr Thr Trp His
1               5

<210> SEQ ID NO 45
<211> LENGTH: 9
<212> TYPE: PRT
<213> ORGANISM: Artificial Sequence
<220> FEATURE:
<223> OTHER INFORMATION: Synthesized

<400> SEQUENCE: 45

Pro Lys His Trp Thr Thr Pro Arg Arg
1               5

<210> SEQ ID NO 46
<211> LENGTH: 21
<212> TYPE: PRT
<213> ORGANISM: Artificial Sequence
<220> FEATURE:
<223> OTHER INFORMATION: Synthesized

<400> SEQUENCE: 46

Arg Arg Pro Thr Thr Trp His Lys Pro Gly Pro Gly Arg Arg Pro Thr
1               5                   10                  15

Thr Trp His Lys Pro
            20

<210> SEQ ID NO 47
<211> LENGTH: 19
<212> TYPE: PRT
<213> ORGANISM: Artificial Sequence
<220> FEATURE:
<223> OTHER INFORMATION: Synthesized

<400> SEQUENCE: 47

Pro Lys His Trp Thr Thr Pro Arg Arg Gly Pro Lys His Trp Thr Thr
1               5                   10                  15

Pro Arg Arg

<210> SEQ ID NO 48
<211> LENGTH: 4
<212> TYPE: PRT
<213> ORGANISM: Artificial Sequence
<220> FEATURE:
<223> OTHER INFORMATION: Synthesized

<400> SEQUENCE: 48

Cys Gly Gly Gly
1
```